US012344862B2

(12) United States Patent
Son et al.

(10) Patent No.: US 12,344,862 B2
(45) Date of Patent: Jul. 1, 2025

(54) HUMAN INTESTINAL EPITHELIUM MODEL AND METHOD FOR PREPARING SAME

(71) Applicant: KOREA RESEARCH INSTITUTE OF BIOSCIENCE AND BIOTECHNOLOGY, Daejeon (KR)

(72) Inventors: Mi Young Son, Daejeon (KR); Ohman Kwon, Daejeon (KR); Kwang Bo Jung, Daejeon (KR); Kyeong-Ryoon Lee, Daejeon (KR); Cho Rok Jung, Daejeon (KR); Janghwan Kim, Daejeon (KR)

(73) Assignee: KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 431 days.

(21) Appl. No.: 17/087,893

(22) Filed: Nov. 3, 2020

(65) Prior Publication Data
US 2022/0135949 A1  May 5, 2022

(51) Int. Cl.
*C12N 5/071* (2010.01)
*A61K 35/38* (2015.01)
*G01N 33/50* (2006.01)

(52) U.S. Cl.
CPC ............ *C12N 5/0679* (2013.01); *A61K 35/38* (2013.01); *G01N 33/5044* (2013.01); *C12N 2501/11* (2013.01); *C12N 2501/16* (2013.01); *C12N 2501/33* (2013.01); *C12N 2501/415* (2013.01); *C12N 2501/42* (2013.01); *C12N 2506/23* (2013.01); *C12N 2506/45* (2013.01)

(58) Field of Classification Search
CPC .............. C12N 5/0679; C12N 2501/11; C12N 2501/16; C12N 2501/33; C12N 2501/415; C12N 2501/42; C12N 2506/23; C12N 2506/45; A61K 35/38; G01N 33/5044
See application file for complete search history.

(56) References Cited

U.S. PATENT DOCUMENTS

2017/0029780 A1* 2/2017 Zhang ................. C12N 5/0688
2017/0349884 A1 12/2017 Karp et al.

FOREIGN PATENT DOCUMENTS

WO  2018/052953 A1  3/2018
WO  2019/021990 A1  1/2019

OTHER PUBLICATIONS

Negoro et al., Efficient Generation of Small Intestinal Epithelial-like Cells from Human iPSCs for Drug Absorption and Metabolism Studies, Stem Cell Reports, 11: 1539-1550. (Year: 2018).*
Zhou et al., Insulin/IGF-1 enhances intestinal epithelial crypt proliferation through PI3K/Akt, and not ERK signaling in obese humans, Experimental Biology and Medicine, 243: 911-916. (Year: 2018).*
Abud et al., Source and Impact of the EGF Family of Ligands on Intestinal Stem Cells, Frontiers in Cell and Developmental Biology, 9: 1-9. (Year: 2021).*
Koo et al., Stem Cells Marked by the R-Spondin Receptor LGR5, Gastroenterology, 147: 289-302. (Year: 2014).*
Suzuki et al., Glucagon-like peptide 1 (1-37) converts intestinal epithelial cells into insulin-producing cells, PNAS: 100(9)L 5034-5039. (Year: 2003).*
Levin et al., R-Spondin 1 (RSPO1) Increases Mouse Intestinal Organoid Unit Size and Survival in vitro and Improves Tissue-Engineered Small Intestine (Frontiers in Bioengineering and Biotechnology, 8(476): 1-13, (Year: 2020).*
Spnce et al., Vertebrate Intestinal Endoderm Development, Developmental Dynamics, 240: 501-520. (Year: 2011).*
Kwang Bo Jung et al., "Interleukin-2 induces the in vitro maturation of human pluripotent stem cell-derived intestinal organoids", Nature Communications, vol. 9, Article 3039. 2018.
Tatsuya Ozawa et al., "Generation of enterocyte-like cells from human induced pluripotent stem cells for drug absorption and metabolism studies in human small intestine", Scientific Reports, vol. 5, Article 16479. 2015.
Gregory P. Donaldson et al., "Gut biogeography of the bacterial microbiota", Nature Reviews Microbiology, vol. 14(1): 20-32, Jan. 2016.
The partial supplementary European search report dated Sep. 11, 2024 for corresponding European Patent Application No. 21889517.5, (16 pages).
Xiaolei Yin et al., "Niche-independent high-purity cultures of Lgr5+ intestinal stem cells and their progeny", Nature Methods, vol. 11, No. 1, Dec. 1, 2013, pp. 106-112, Cited in NPL No. 1.
Daichi Onozato et al., "Generation of Intestinal Organoids Suitable for Pharmacokinetic Studies from Human Induces Pluripotent Stem Cells", Drug Metabolism and Disposition, vol. 46, No. 11, Apr. 3, 2018, pp. 1572-1580, Cited in NPL No. 1.
Ohman Kwon et al., "The development of a functional human small intestinal epithelium model for drug absorption", Science Advances, vol. 7, No. 23, Jun. 2, 2021, 18 pages, Cited in NPL No. 1.

* cited by examiner

Primary Examiner — Arthur S Leonard
Assistant Examiner — Joseph Paul Miano
(74) Attorney, Agent, or Firm — Hauptman Ham, LLP

(57) ABSTRACT

The present invention relates to a method for preparing a human intestinal epithelial model. The human intestinal epithelial model, prepared by the method according to the present invention, has all characteristics of goblet cells, enteroendocrine cells, and Paneth cells, and thus can highly mimic the function of actual human intestinal cells, so that the human intestinal epithelial model can be effectively used for development of new drugs, evaluation of drug absorption and toxicity, or evaluation of engraftment of intestinal microorganisms, or as a composition for in vivo transplantation.

5 Claims, 42 Drawing Sheets
Specification includes a Sequence Listing.

FIG. 25

| Transplanted cell type | Immature hIECs | Functional hIECs |
|---|---|---|
| Cell injected (x10$^7$) | 0.5-1 | 0.5-1 |
| Mice bearing mass /total mice | 10/10 | 9/10 |
| Mice bearing mass consisting of residual cells/total mice | 2/10 | 0/10 |

FIG. 33

| Locus/Clone | H9 hESC | | Patient #1-Fibroblasts | | Patient #1-iPSCs | | Patient #2-Fibroblasts | | Patient #2-iPSCs | |
|---|---|---|---|---|---|---|---|---|---|---|
| D8S1179 | 8 | 14 | 11 | 12 | 11 | 12 | 13 | 14 | 13 | 14 |
| D21S11 | 30 | 30 | 30 | 30 | 30 | 30 | 30 | 30 | 30 | 30 |
| D7S820 | 9 | 11 | 10 | 13 | 10 | 13 | 10 | 11 | 10 | 11 |
| CSF1PO | 11 | 11 | 11 | 11 | 11 | 11 | 10 | 11 | 10 | 11 |
| D3S1358 | 13 | 16 | 15 | 15 | 15 | 15 | 16 | 16 | 16 | 16 |
| TH01 | 9.3 | 9.3 | 9 | 9 | 9 | 9 | 6 | 6 | 6 | 6 |
| D13S317 | 9 | 9 | 9 | 12 | 9 | 12 | 8 | 11 | 8 | 11 |
| D16S539 | 12 | 13 | 9 | 11 | 9 | 11 | 10 | 12 | 10 | 12 |
| D2S1338 | 18 | 24 | 19 | 20 | 19 | 20 | 19 | 23 | 19 | 23 |
| D19S433 | 12 | 15 | 15.2 | 16.2 | 15.2 | 16.2 | 13 | 14 | 13 | 14 |
| vWA | 17 | 17 | 18 | 19 | 18 | 19 | 14 | 16 | 14 | 16 |
| TPOX | 10 | 10 | 8 | 8 | 8 | 8 | 8 | 11 | 8 | 11 |
| D18S51 | 12.3 | 13 | 13 | 13 | 13 | 13 | 14 | 16 | 14 | 16 |
| D5S818 | 11 | 12 | 10 | 11 | 10 | 11 | 12 | 13 | 12 | 13 |
| FGA | 26 | 28 | 23 | 26 | 23 | 26 | 23 | 23 | 23 | 23 |
| Gender | XX | | XX | | XX | | XY | | XY | |

| Test drugs | In vitro model Papp A→B ($10^{-6}$ cm/sec) | | Human data reported in the literature | | |
|---|---|---|---|---|---|
| | hIEC | Caco-2 | Fraction absorbed ($F_a$) | Intestinal availability related to the metabolism ($F_g$) | Fraction absorbed in human intestine ($F_{intestine}$) |
| Metoprolol | 11.10±1.15 | 36.54±1.09 | 0.98 | 0.84 | 0.82 |
| Ranitidine | 6.98±0.66 | 0.98±0.02 | 0.65 | 1.02 | 0.66 |
| Propranolol | 11.02±1.28 | 32.29±2.61 | 0.99 | 0.50 | 0.49 |
| Diclofenac | 9.82±0.04 | 36.23±1.49 | 1.00 | 0.64 | 0.64 |

HUMAN INTESTINAL EPITHELIUM MODEL AND METHOD FOR PREPARING SAME

TECHNICAL FIELD

The present invention relates to a human intestinal epithelial model and a method for preparing the same.

BACKGROUND ART

Human intestinal epithelial cells are the first place for drug absorption and metabolism and are known to express various enzymes related to drug absorption and metabolism. Specifically, in the intestinal epithelial cells, many transporters and enzymes are expressed, such as PEPT1 related to drug absorption, P-gp and MDR1 which are related to drug efflux, and CYP3A4 related to drug metabolism. In addition, it is known that expression of the transporters and enzymes in the small intestine is important for pharmacokinetic and pharmacodynamic prediction. In particular, the essential information required to evaluate bioavailability and variability of an oral drug is an efflux amount of absorbed drug by P-gp and CYP3A4-mediated first-pass metabolism thereof.

Existing human pluripotent stem cell-derived 2D intestinal epithelial models do not have epithelial cells of other cell types, such as goblet cells, enteroendocrine cells, and Paneth cells, other than enterocytes, and thus have limitations to mimic the actual human intestine. In addition, the 2D intestinal epithelial models have also limitations in large-scale culture and their functionality has not been clearly verified, which makes it difficult to apply such models as an intestinal epithelial model for actually evaluating drug efficacy.

Currently, the Caco-2 cell line, which is a human colon adenocarcinoma cell line, is widely used as a standard enterocyte model for evaluating drug absorption and metabolism. The Caco-2 cell line is polarized in the same way as enterocytes, forms physical and biochemical barriers, and expresses characteristic transporters for drug absorption. However, the Caco-2 cell line has different characteristics from common intestinal epithelial cells, and thus has limitations for use as an intestinal epithelial model. Specifically, the Caco-2 cell line is problematic in that it exhibits very low absorption of a hydrophilic drug through an intercellular route because the expression level of tight junction molecules is higher than that in human intestinal epithelial cells. In addition, the Caco-2 cell line is different from human intestinal epithelial cells in terms of expression levels of drug transporters and metabolic enzymes, which makes it difficult to accurately evaluate bioavailability of a drug (Ozawa T et al., Scientific reports. 2015; 5: 16479). Therefore, there is a need to develop a new intestinal epithelial model that can more accurately mimic human intestinal epithelial cells to evaluate bioavailability of a drug.

In addition, the large intestine has the largest number of various types of intestinal microorganisms, while the small intestine also has a large number of various types of intestinal microorganisms. The small intestine has a low pH and high concentrations of oxygen and antimicrobials as compared with the large intestine. Thus, Lactobaccilacea and Enterobacteriacea, which are rapidly growing facultative anaerobic bacteria that effectively consume simple carbohydrates while being resistant to bile acids and antimicrobials, dominate in the small intestine (Donaldson et al., Nature Reviews Microbiology. 2016; 14(1): 20-32). Likewise, the Caco-2 cell line is mainly used even in research on intestinal microorganisms; however, this cell line does not reflect diversity of intestinal cells, and in particular, is problematic in that it does not have goblet cells which secrete mucus that is important for engraftment of intestinal microorganisms. Accordingly, there is a need to develop a new intestinal epithelial model for research on intestinal microorganisms which can reflect an environment in the small intestine.

DISCLOSURE OF INVENTION

Technical Problem

As a result of making efforts to develop a human intestinal epithelial model that can more accurately mimic human intestinal cells, the present inventors have found that adjustment of composition of a differentiation medium causes human intestinal epithelial cell progenitors to differentiate into all of goblet cells, enteroendocrine cells, and Paneth cells. Based on this finding, the present inventors have identified a human intestinal epithelial model having all characteristics of these cells, and thus have completed the present invention.

Solution to Problem

To solve the problem, in an aspect of the present invention, there is provided a method for preparing a human intestinal epithelial cell population, comprising a step of culturing human intestinal epithelial cell progenitors (hIEC progenitors) in a medium containing EGF, a Wnt inhibitor, and a Notch activator.

In another aspect of the present invention, there is provided a human intestinal epithelial cell population, prepared by the above-described method.

In yet another aspect of the present invention, there is provided a human intestinal epithelial model, comprising the human intestinal epithelial cell population.

In still yet another aspect of the present invention, there is provided a method for preparing human intestinal epithelial cell progenitors, comprising a step of culturing endoderm cells in a medium containing EGF, R-spondin 1, and insulin.

In still yet another aspect of the present invention, there is provided a human intestinal epithelial cell progenitor, prepared by the above-described preparation method.

In still yet another aspect of the present invention, there is provided a medium composition for differentiation of human intestinal epithelial cells, comprising EGF, a Wnt inhibitor, and a Notch activator.

In still yet another aspect of the present invention, there is provided a medium composition for differentiation of human intestinal epithelial cell progenitors, comprising EGF, R-spondin 1, and insulin.

In still yet another aspect of the present invention, there is provided a kit for preparing a human intestinal epithelial cell population, comprising a first composition that includes EGF, R-spondin 1, and insulin; and a second composition that includes EGF, a Wnt inhibitor, and a Notch activator.

In still yet another aspect of the present invention, there is provided a method for evaluating a drug, comprising steps of: subjecting the human intestinal epithelial model to treatment with the drug; and evaluating absorption or bioavailability of the drug in the human intestinal epithelial model.

In still yet another aspect of the present invention, there is provided a method for evaluating an intestinal microorganism, comprising steps of: subjecting the human intestinal epithelial model to treatment with the intestinal microorganism; and evaluating engraftment capacity and clustering of the intestinal microorganism in the intestinal epithelial model.

In still yet another aspect of the present invention, there is provided a composition for in vivo transplantation, comprising the human intestinal epithelial cell population.

Advantageous Effects of Invention

The human intestinal epithelial cell population or the human intestinal epithelial model, prepared by the method according to the present invention, has all characteristics of goblet cells, enteroendocrine cells, and Paneth cells, and thus can highly mimic the function of actual human intestinal cells, so that the human intestinal epithelial cell population or the human intestinal epithelial model can be effectively used for development of new drugs, evaluation of drug absorption and bioavailability, and research on intestinal microorganisms.

BRIEF DESCRIPTION OF DRAWINGS

FIG. 25 illustrates a diagram, summarizing experimental conditions used to identify cell maintenance capacity in vivo of functional hIECs using a mouse model.

FIG. 33 illustrates short tandem repeat (STR) profiles of fibroblast-derived iPSCs.

BEST MODE FOR CARRYING OUT THE INVENTION

Figure 1:
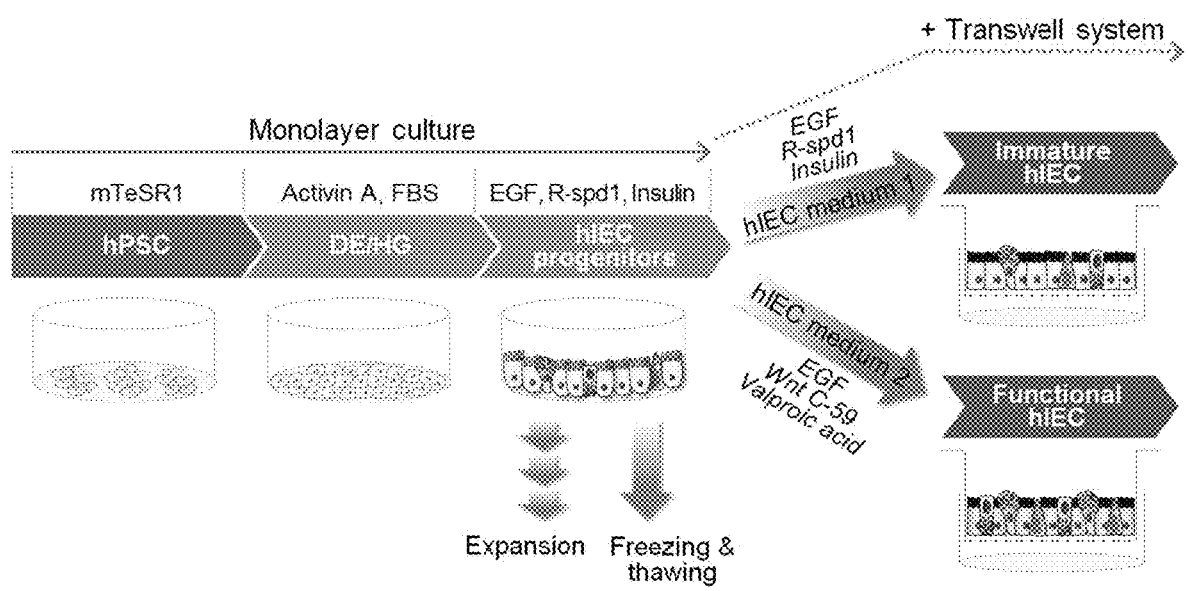
FIG. 1 illustrates a schematic diagram, showing a process of differentiation of human pluripotent stem cells (hPSCs) into human intestinal epithelial cells (hIECs).

Hereinafter, the present invention will be described in more detail.

In an aspect of the present invention, there is provided a method for preparing a human intestinal epithelial cell population, comprising a step of culturing human intestinal epithelial cell progenitors (hIEC progenitors) in a medium containing EGF, a Wnt inhibitor and a Notch activator. Here, the culture may be monolayer culture.

The human intestinal epithelial cell population may have all characteristics of enterocytes, goblet cells, enteroendocrine cells, and Paneth cells in a case where the human intestinal epithelial cell progenitors differentiate into all of enterocytes, goblet cells, enteroendocrine cells, and Paneth cells. In an embodiment of the present invention, the above-mentioned human intestinal epithelial cell population was named functional human intestinal epithelial cells (functional hIECs).

The goblet cells are also called mucus-secreting cells. In a state of storing mucus to be secreted or substances in their stage before becoming mucus, the goblet cells exist in a form in which the base with the nucleus is thin and the reservoir containing secretion is swollen, like a wine glass. The goblet cells can serve to actively accept glucose and amino acids, make them mucoproteins, collect the mucoproteins in their goblet portion, and release the mucoproteins into the lumen.

The enteroendocrine cells are also called hormone secretory cells. The enteroendocrine cells produce hormones or peptides in response to various stimuli, and secrete them throughout the body via blood or transmit them to the intestinal nervous system, so that neural responses can be activated.

The enteroendocrine cells may consist of one or more cells selected from the group consisting of K-cells, L-cells, I-cells, G-cells, enterochromaffin cells, N-cells, S-cells, D-cells, and M-cells.

The "K-cells" are cells that secrete incretin, which is a gastrointestinal inhibitory peptide, and promote storage of triglycerides. The "L-cells" are cells that secrete glucagon-like peptide-1, glucagon-like peptide-2, incretin, oxyntomodulin, and the like. The "I-cells" are cells that secrete cholecystokinin (CCK). The "G-cells" are cells that secrete gastrin. The "enterochromaffin cells" are a type of neuroendocrine cells and secrete serotonin. The "N-cells" are cells that secrete neurotensin, and regulate contraction of smooth muscle. The "S-cells" are cells that secrete secretin. The "D-cells" are called Delta cells and secrete somatostatin. The "M-cells" are also called Mo cells and secrete motilin.

The Paneth cells are one of the cell types in the small intestine mucosa, and are secretory epithelial cells containing a large number of granules, located in the crypts of Lieberkühn which are a type of small intestine glands. In secretory granules of the Paneth cells, proteins with many disulfide bonds, and mucopolysaccharides are present in large numbers. The Paneth cells exist below the stem cells that regenerate intestinal epithelial cells, and appear to migrate downward from the stem cells during differentiation. The Paneth cells have lysozyme that degrades peptidoglycan in the bacterial cell wall, and thus can have a function of eliminating microorganisms through phagocytosis.

The epidermal growth factor (EGF) refers to a growth factor that can bind to epidermal growth factor receptor (EGFR), which is a receptor thereof, and promote cell proliferation, growth, and differentiation. The EGF has activity of promoting proliferation of various epithelial cells and can also proliferate mouse T cells or human fibroblasts.

The EGF may be included in a medium at a concentration of 0.1 ng/ml to 100 μg/ml. Specifically, the EGF may be included in a medium at a concentration of 0.1 ng/ml to 100 μg/ml, 1 ng/ml to 50 μg/ml, 2 ng/ml to 10 μg/ml, 5 ng/ml to 1 μg/ml, or 10 ng/ml to 500 ng/ml. In an embodiment of the present invention, the EGF was included in a medium at a concentration of 100 ng/ml.

The Wnt inhibitor may be any one or more selected from the group consisting of Wnt C-59, IWP-2, LGK974, ETC-1922159, RXC004, CGX1321, XAV-939, IWR, G007-LK, HQBA, PKF115-584, iCRT, PRI-724, ICG001, DKK1, SFRP1, and WIF1. Specifically, the Wnt inhibitor may be, but is not limited to, Wnt C-59 represented by Formula 1.

[Formula 1]

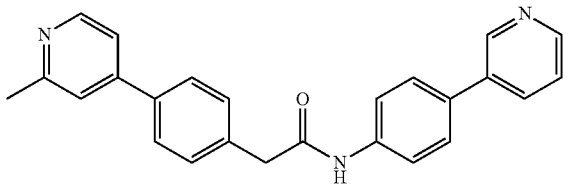 [SMILES: Cc1cc(-c2ccc(CC(=O)Nc3ccc(-c4cccnc4)cc3)cc2)ccn1]

The Wnt inhibitor may be included in a medium at a concentration of 0.1 μM to 100 μM. Specifically, the EGF may be included in a medium at a concentration of 0.1 μM to 100 μM, 0.5 μM to 50 μM, 1 μM to 10 μM, or 1.5 μM to 5 μM. In an embodiment of the present invention, the Wnt inhibitor was included in a medium at a concentration of 2 μM.

The Notch activator may be any one or more selected from the group consisting of valproic acid, oxaliplatin, nuclear factor, erythroid derived 2 (Nrf2), Delta-like 1 (DLL1), Delta-like 3 (DLL3), Delta-like 4 (DLL4), Jagged1 (JAG1), and Jagged2 (JAG2). Specifically, the Notch activator may be, but is not limited to, valproic acid represented by Formula 2.

[Formula 2]

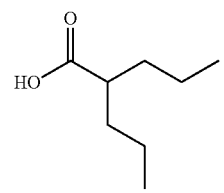

The Notch activator may be included in a medium at a concentration of 100 μM to 100 mM. Specifically, the Notch activator may be included in a medium at a concentration of 100 μM to 100 mM, 500 μM to 50 mM, or 1 mM to 5 mM. In an embodiment of the present invention, the Notch activator was included in a medium at a concentration of 1 mM.

The human intestinal epithelial cell progenitors may consist of intestinal stem cells, intestinal progenitor cells, undifferentiated enterocytes, goblet cells, enteroendocrine cells, or Paneth cells.

The intestinal stem cells (LGR5, ASCL2), intestinal progenitor cells (SOX9), undifferentiated enterocytes (VIL, ANPEP, SI), goblet cells (MUC2), enteroendocrine cells (CHGA), and Paneth cells (LYZ), which constitute the human intestinal epithelial cell progenitors, can be identified through expression of their respective related markers. In an embodiment of the present invention, the human intestinal epithelial cell progenitors may be obtained by culturing endoderm (DE) or hindgut (HG) cells in a medium containing EGF, R-spondin 1, and insulin.

The EGF is as described above, and the EGF may be included in the medium at a concentration of 0.1 ng/ml to 100 μg/ml. Specifically, the EGF may be included in the medium at a concentration of 0.1 ng/ml to 100 μg/ml, 1 ng/ml to 50 μg/ml, 2 ng/ml to 10 μg/ml, 5 ng/ml to 1 μg/ml, or 10 ng/ml to 500 ng/ml. In an embodiment of the present invention, the EGF was included in the medium at a concentration of 100 ng/ml.

The R-spondin 1 is a secreted protein encoded by Rspo1 gene, and can promote Wnt/β catenin signals. The R-spondin 1 may be included in the medium at a concentration of 0.1 ng/ml to 100 μg/ml. Specifically, the R-spondin 1 may be included in the medium at a concentration of 0.1 ng/ml to 100 μg/ml, 1 ng/ml to 50 μg/ml, 2 ng/ml to 10 μg/ml, 5 ng/ml to 1 μg/ml, or 10 ng/ml to 500 ng/ml. In an embodiment of the present invention, the R-spondin 1 was included in the medium at a concentration of 100 ng/ml.

The insulin is secreted from beta cells of the islet of Langerhans, and serves to keep a blood sugar level, which is a glucose level in the blood, constant. When the blood sugar level increases above a certain level, insulin is secreted to promote an action by which glucose in the blood is caused to enter cells, where the glucose is stored again in the form of polysaccharide (glycogen).

The insulin may be included in the medium at a concentration of 0.1 μg/ml to 100 μg/ml. Specifically, the insulin may be included in the medium at a concentration of 0.1

μg/ml to 100 μg/ml, 1 μg/ml to 50 μg/ml, or 2 μg/ml to 10 μg/ml. In an embodiment of the present invention, the insulin was included in the medium at a concentration of 5 μg/ml.

The endoderm cells may be differentiated from human pluripotent stem cells (hPSCs). Specifically, the endoderm cells may be, but are not limited to, foregut endoderm cells, midgut endoderm cells, or hindgut endoderm cells, with hindgut endoderm cells being specifically mentioned. In an embodiment of the present invention, the endoderm cells or hindgut endoderm cells may be obtained by culturing human pluripotent stem cells (hPSCs) in a medium containing Activin A and FBS.

The human pluripotent stem cells may be human embryonic stem cells (hESCs) or induced pluripotent stem cells (iPSCs). The induced pluripotent stem cells may be derived from fibroblasts isolated from small intestine tissue. In an embodiment of the present invention, functional human intestinal epithelial cells were obtained using the induced pluripotent stem cells derived from fibroblasts isolated from small intestine tissue.

In an embodiment of the present invention, the human pluripotent stem cells were cultured in a medium containing Activin A, FBS, FGF4, and Wnt3A, to differentiate into endoderm (DE) cells, and then the endoderm cells were transferred to and cultured in intestinal epithelial cell differentiation medium 1 (IEC differentiation medium 1 or hIEC differentiation medium 1) containing EGF, R-spondin 1 (R-spd1), and insulin, to induce differentiation into human intestinal epithelial cell progenitors.

There have been many reports on cases where a Wnt activator is used as a component in a medium composition for differentiation of stem cells into enterocytes; however, there have been no reports on cases where a Wnt inhibitor is used in composition of a differentiation medium.

In another aspect of the present invention, there is provided a human intestinal epithelial cell population, prepared by the above-described preparation method. The human intestinal epithelial cell population is as described above in the method for preparing a human intestinal epithelial cell population. Specifically, the human intestinal epithelial cell population may include enterocytes, goblet cells, enteroendocrine cells, and Paneth cells. The human epithelial model can be used for research on drugs (for example, absorption and bioavailability) or intestinal microorganisms (for example, engraftment capacity and clustering).

The human intestinal epithelial cell population may be a human intestinal epithelial cell population that has one or more of the following characteristics (i) to (v):

(i) characteristic of showing positivity for any one or more selected from the group consisting of CDX2, VIL1, ANPEP, SI, LGR5, LYZ, MUC2, MUC13, CHGA, and combinations thereof;

(ii) characteristic of showing positivity for any one or more selected from the group consisting of OCLN, CLDN1, CLDN3, CLDN4, CLDN5, CLDN7, CLDN15, ZO-1, and combinations thereof;

(iii) characteristic of showing negativity for any one or more selected from the group consisting of ATOH1, AXIN2, CTNNB1, and combinations thereof;

(iv) characteristic of showing positivity for HES1; and (v) characteristic of showing positivity for any one or more selected from the group consisting of CDX2, ANPEP, CYP3A4, GLUT2, GLUT5, and combinations thereof.

Figure 7:
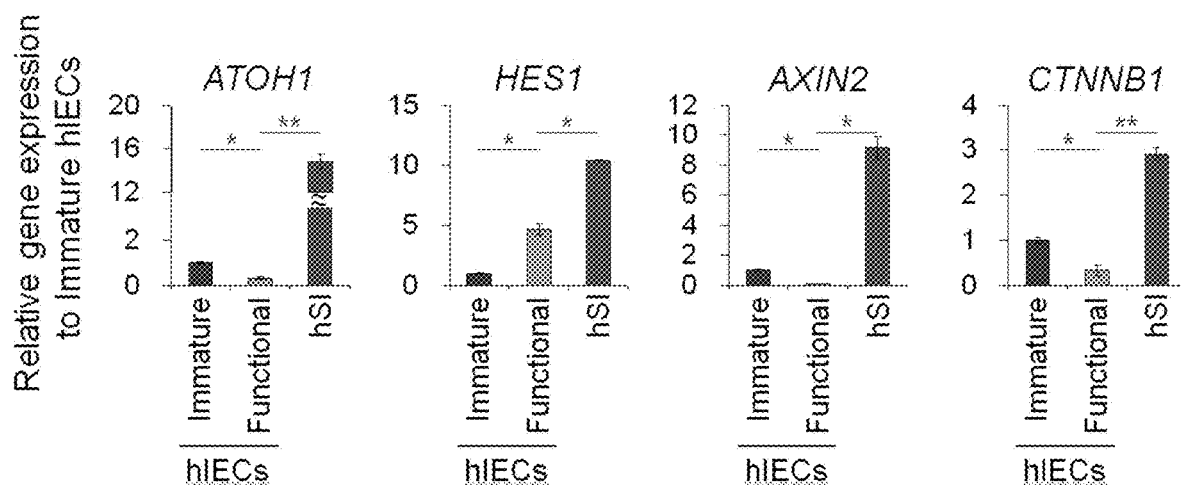
FIG. 7 illustrates graphs, showing expression levels of ATOH1, HES1, AXIN2, and CTNNB1 genes in immature hIECs and functional hIECs.
Figure 8:
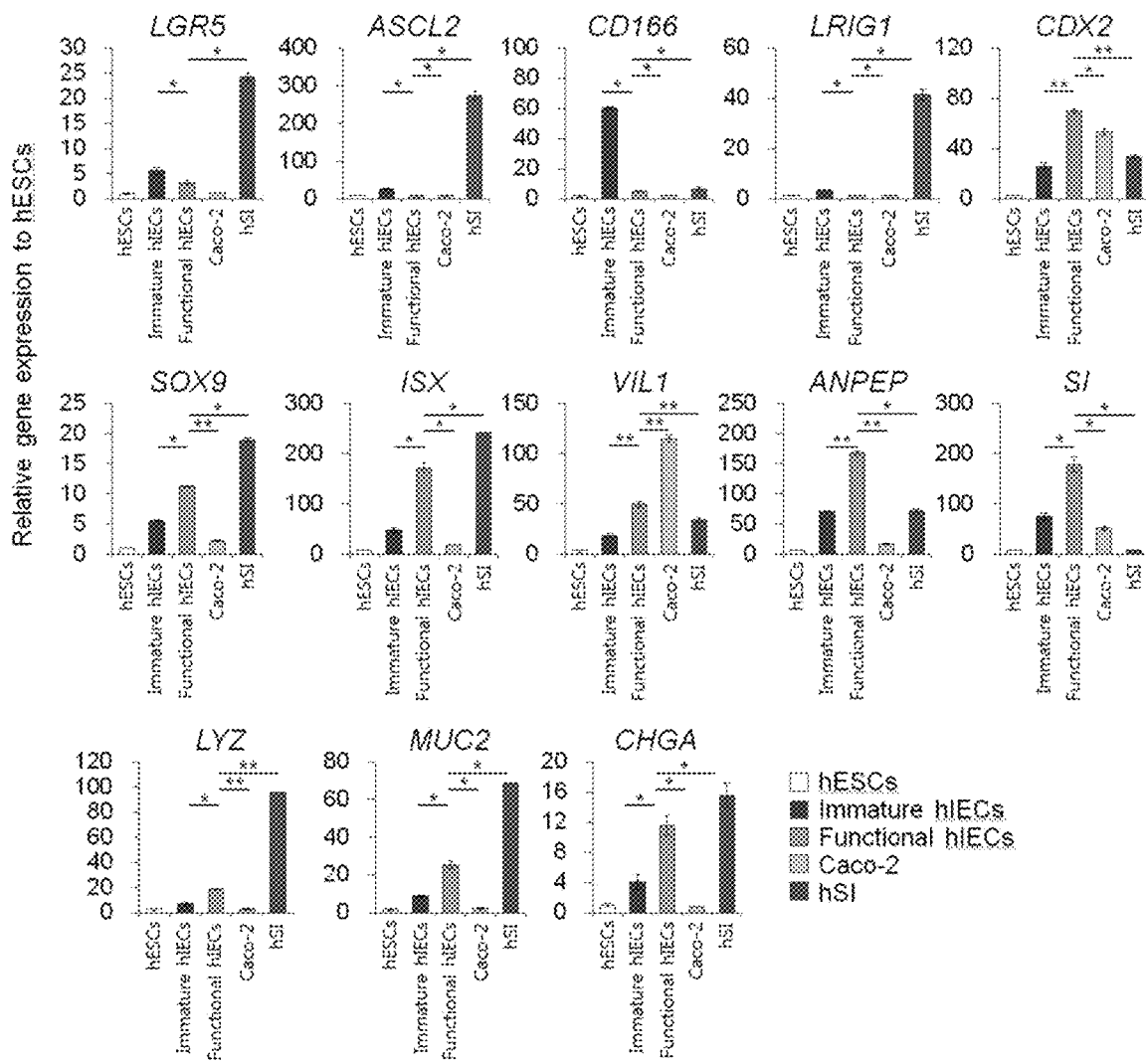
FIG. 8 illustrates graphs, showing expression levels of LGR5, ASCL2, CD166, LRIG1, CDX2, SOX9, ISX, VIL1, ANPEP, SI, LYZ, MUC2, MUC13, and CHGA genes in immature hIECs and functional hIECs.
Figure 10:
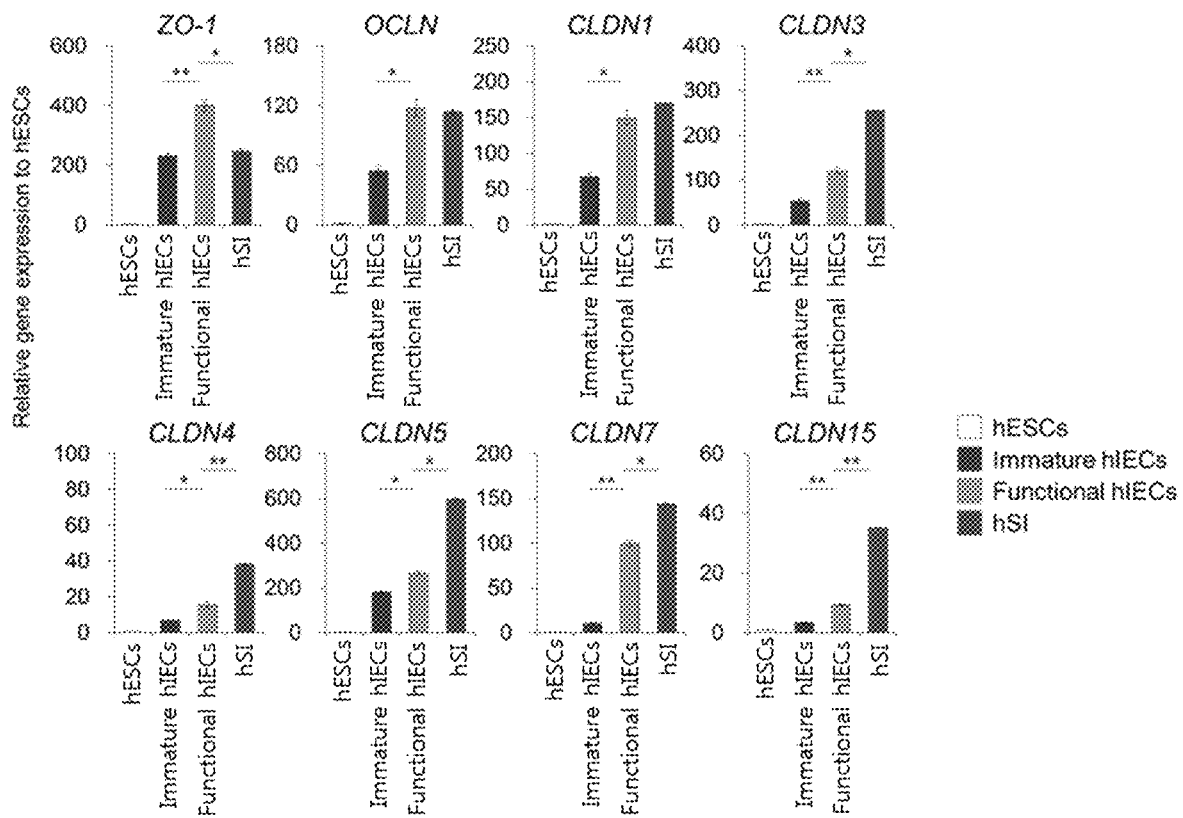
FIG. 10 illustrates graphs, showing expression levels of OCLN, CLDN1, CLDN3, CLDN4, CLDN5, CLDN7, CLDN15, and ZO-1 genes in immature hIECs and functional hIECs.
Figure 22:
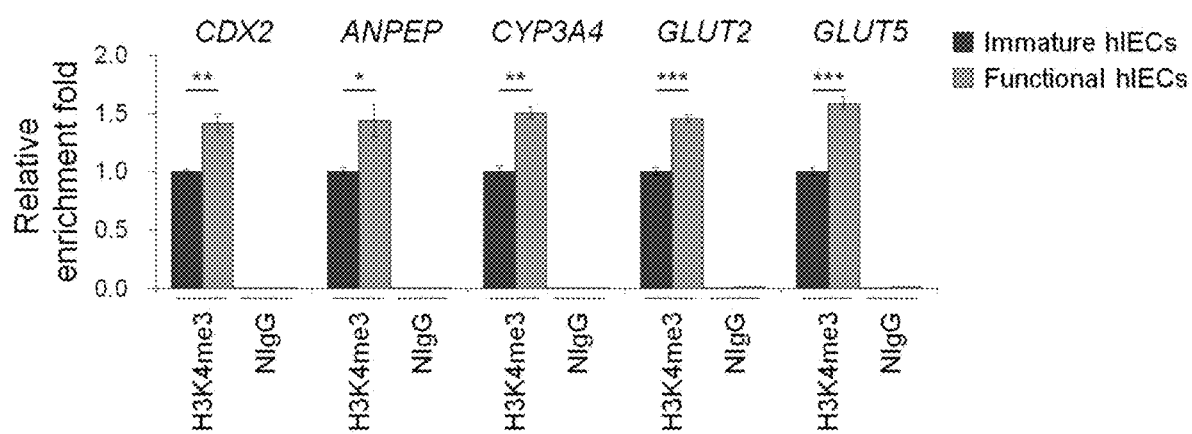
FIG. 22 illustrates a graph, showing enrichment amounts of H3K4me3, which is an active histone mark, in the promoter/enhancer region of CDX2, ANPEP, CYP3A4, GLUT2, and GLUT5 genes in immature hIECs and functional hIECs.

In an embodiment of the present invention, it was identified that the human intestinal epithelial cell population of the present invention showed excellent activity of the following marker genes: CDX2 and VIL1 for enterocytes, LYZ for Paneth cells, MUC2 for goblet cells, and CHGA for enteroendocrine cells; and it was identified that the human intestinal epithelial cell population showed excellent expression of CDX2, VIL1, ANPEP, SI, LGR5, LYZ, MUC2, MUC13, and CHGA, which are marker genes for intestinal and secretory cells (FIG. 8). In addition, it was identified that the human intestinal epithelial cell population of the present invention showed excellent expression of OCLN, CLDN1, CLDN3, CLDN4, CLDN5, CLDN7, CLDN15, and ZO-1, which are marker genes for tight junction molecules (FIG. 10). In addition, it was identified that the human intestinal epithelial cell population of the present invention showed decreased expression of ATOH1, AXIN2, and CTNNB1, and excellent expression of HES1 (FIG. 7). In addition, the human intestinal epithelial cell population of the present invention showed excellent expression of CDX2, ANPEP, CYP3A4, GLUT2, and GLUT5 (FIG. 22).

In yet another aspect of the present invention, there is provided a human intestinal epithelial model, comprising the human intestinal epithelial cell population. The human intestinal epithelial cell population is as described above.

In still yet another aspect of the present invention, there is provided a method for preparing human intestinal epithelial cell progenitors, comprising a step of culturing endoderm cells in a medium containing EGF, R-spondin 1, and insulin. The method of culturing the endoderm cells in the medium containing EGF, R-spondin 1, and insulin is as described above in the method for preparing a human intestinal epithelial cell population.

In still yet another aspect of the present invention, there is provided a human intestinal epithelial cell progenitor, prepared by the above-described preparation method.

Figure 5:
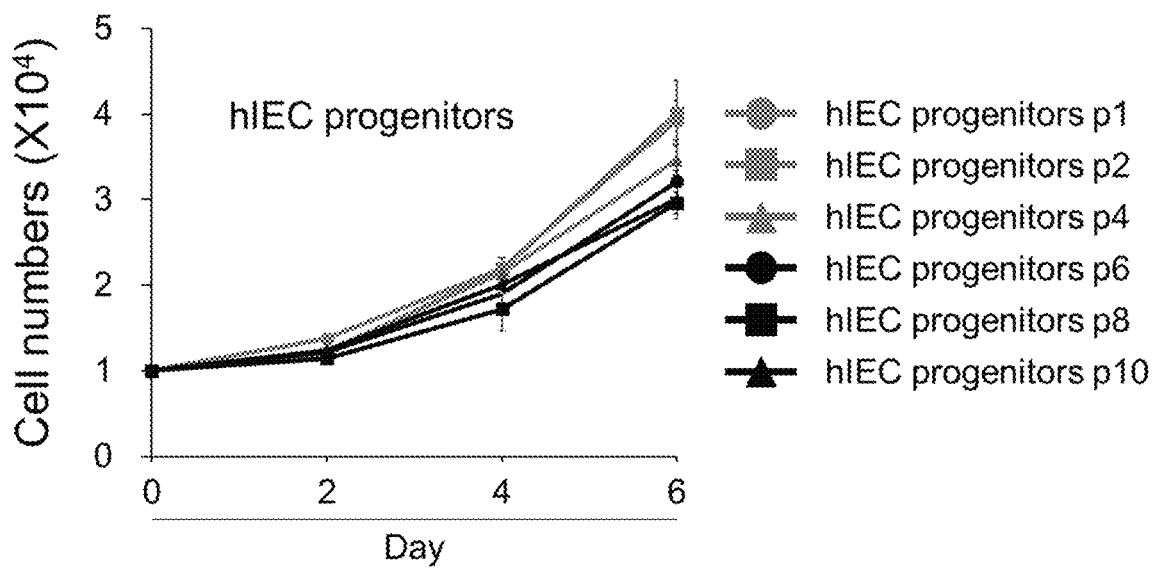
FIG. 5 illustrates a graph, showing viable cell numbers, depending on the number of passages, in hIEC progenitors.

The human intestinal epithelial cell progenitors may be passageable. Specifically, the human intestinal epithelial cell progenitors may be passageable 1, 2, 3, 4, 5, 6, 7, 8, 9, 10, or more times. In an embodiment of the present invention, the human intestinal epithelial cell progenitors were passaged 2, 4, 6, 8, and 10 times, and the expression levels of marker genes related to intestinal epithelial cells and the number of viable cells were measured. As a result, it was identified that in the human intestinal epithelial cell progenitors, the expression of marker genes for enterocytes and tight junction molecules was stably maintained, and the number of viable cells increased as the number of passages and the culture period increased (FIG. 5).

Figure 3:
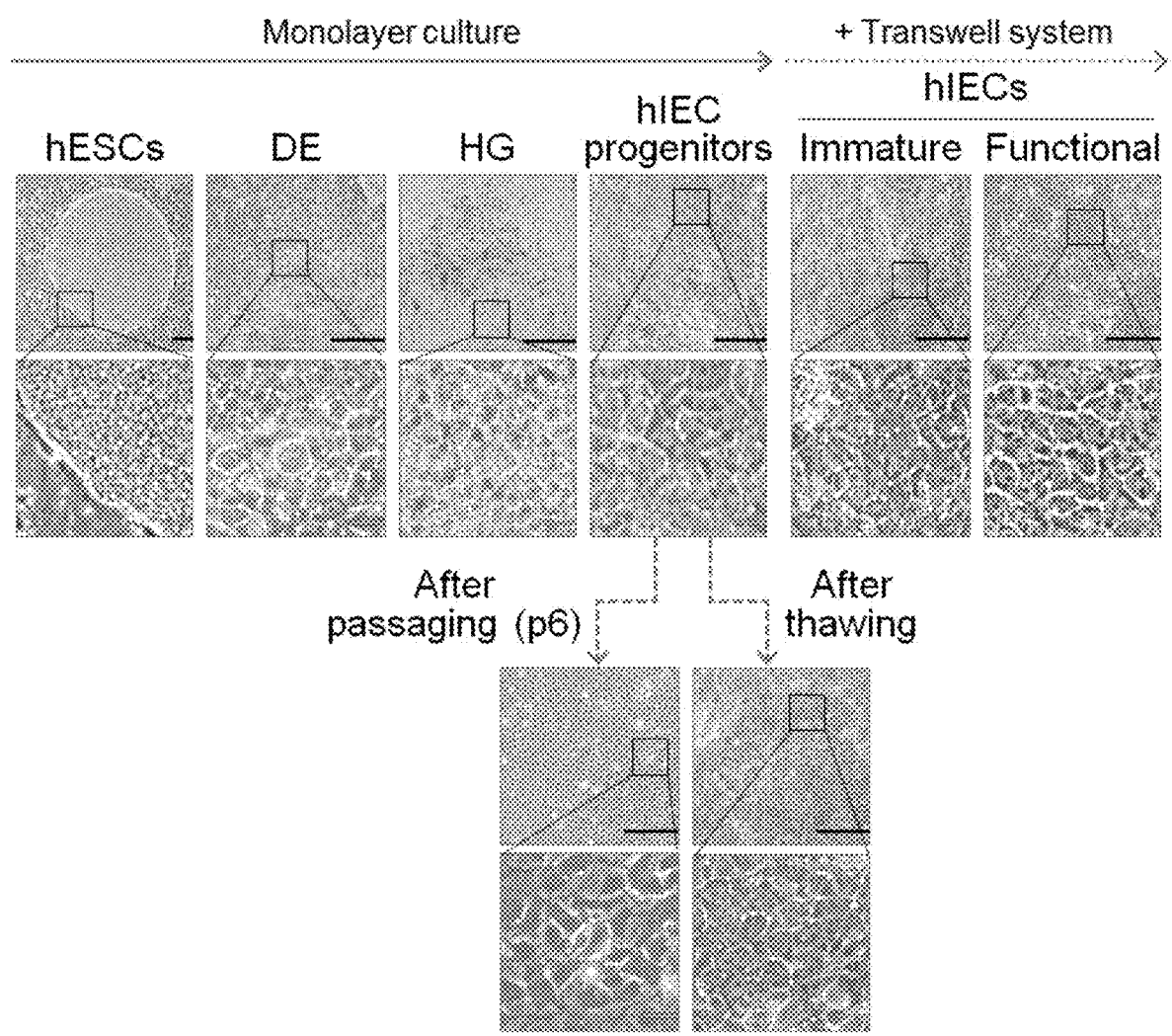
FIG. 3 illustrates diagrams, identifying morphological differences between hESCs, endoderm (DE), hindgut (HG), hIEC progenitors (freezing and thawing), immature hIECs, and functional hIECs.

The human intestinal epithelial cell progenitors may be capable of freezing and thawing. Specifically, in an embodiment of the present invention, the human intestinal epithelial cell progenitors, which had been passaged 6 times, were subjected to freezing and thawing, and observed. As a result, no significant morphological difference was observed between the human intestinal epithelial cell progenitors after thawing and the human intestinal epithelial cell progenitors before freezing (FIG. 3). As such, the human epithelial cell progenitors may be stored frozen, for example, with any cryoprotectant known in the art.

In still yet another aspect of the present invention, there is provided a medium composition for differentiation of human intestinal epithelial cells, comprising EGF, a Wnt inhibitor, and a Notch activator. The EGF, the Wnt inhibitor, and the Notch activator are as described above in the method for preparing a human intestinal epithelial cell population.

The medium composition for differentiation of human intestinal epithelial cells may additionally comprise any one selected from the group consisting of DMEM/F12, FBS, B27 supplement, Na supplement, L-glutamine, NEAA, HEPES buffer, and combinations thereof.

Specifically, in an embodiment of the present invention, the medium composition (hIEC differentiation medium 2) for differentiation of human intestinal epithelial cells may comprise DMEM/F12, 100 ng/ml of epithelial growth factor (EGF), 2 µM Wnt-059 (Selleckchem, Huston, TX, USA), 1 mM valproic acid (Stemgent, Huston, TX, USA), 2% FBS, 2% B27 supplement (Thermo Fisher Scientific Inc.), 1% Na supplement (Thermo Fisher Scientific Inc.), 2 mM L-glutamine (Thermo Fisher Scientific Inc.), 1% NEAA, and 15 mM HEPES buffer (Thermo Fisher Scientific Inc.).

In still yet another aspect of the present invention, there is provided a medium composition for differentiation of human intestinal epithelial cell progenitors, comprising EGF, R-spondin 1, and insulin. The EGF, the R-spondin 1, and the insulin are as described above in the method for preparing a human intestinal epithelial cell population.

The medium composition for differentiation of human intestinal epithelial cell progenitors may additionally comprise any one selected from the group consisting of DMEM/F12, FBS, B27 supplement, Na supplement, L-glutamine, NEAA, HEPES buffer, and combinations thereof.

Specifically, in an embodiment of the present invention, the medium composition (hIEC differentiation medium 1) for differentiation of human intestinal epithelial cell progenitors may comprise DMEM/F12, 100 ng/ml of epithelial growth factor (EGF), 100 ng/ml of R-spondin 1 (Peprotech), 5 µg/ml of insulin (Thermo Fisher Scientific Inc.), 2% FBS, 2% B27 supplement (Thermo Fisher Scientific Inc.), 1% N2 supplement (Thermo Fisher Scientific Inc.), 2 mM L-glutamine (Thermo Fisher Scientific Inc.), 1% NEAA, and 15 mM HEPES buffer (Thermo Fisher Scientific Inc.).

In still yet another aspect of the present invention, there is provided a kit for preparing a human intestinal epithelial cell population, comprising a first composition that includes EGF, R-spondin 1, and insulin; and a second composition that includes EGF, a Wnt inhibitor, and a Notch activator. The first composition that includes EGF, R-spondin 1, and insulin is the same as the medium composition for differentiation of human intestinal epithelial cell progenitors, and the second composition that includes EGF, a Wnt inhibitor, and a Notch activator is the same as the medium composition for differentiation of human intestinal epithelial cells.

In still yet another aspect of the invention, there is provided a method for evaluating a drug, comprising steps of: subjecting the human intestinal epithelial model to treatment with the drug; and evaluating absorption or bioavailability of the drug in the human intestinal epithelial model.

In still yet another aspect of the present invention, there is provided a composition for in vivo transplantation, comprising the human intestinal epithelial cell population.

Figure 28:
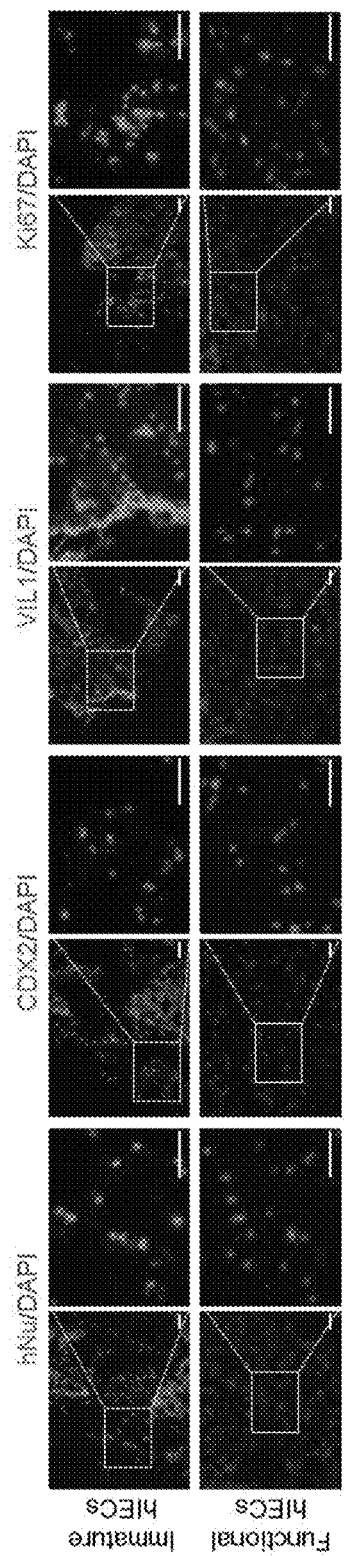
FIG. 28 illustrates results obtained by identifying, through immunofluorescence staining, expression of nuclear antigen (hNu), intestinal transcription factor (CDX2), intestinal protein (VIL1), and proliferation marker (Ki) in a mouse after subcutaneous transplantation of immature hIECs and functional hIECs on the right and left flanks of the mouse, respectively.

In an embodiment of the present invention, subcutaneous cell transplantation was performed using a mouse model, and then presence of residual cells and further differentiation thereof were checked. As a result, it was identified that functional hIEC-Matrigel plugs for the mice transplanted with functional hIECs did not contain human cells even after long-term in vivo culture, and the functional hIECs were finally differentiated into mature intestinal epithelium (FIG. 28). Therefore, the human intestinal epithelial cell population of the present invention has a small proportion of undifferentiated cells, and thus has little risk of forming teratoma, which allows it to be used for in vivo transplantation.

MODE FOR THE INVENTION

Hereinafter, the present invention will be described in more detail by way of the following examples. However, the following examples are for illustrative purposes only, and the scope of the present invention is not limited thereto.

I. Preparation of Functional Human Intestinal Epithelial Cells (Functional hIECs) Using Human Pluripotent Stem Cells (hPSCs)

To prepare a human intestinal epithelial cell (hIEC) model differentiated from human pluripotent stem cells (hPSCs), a new differentiation method that mimics development of the small intestine in vivo was established. The human intestinal epithelial cell model prepared by the above-mentioned method is referred to as functional human intestinal epithelial cells (functional hIECs). A schematic diagram of a method, in which hPSCs are differentiated, via hIEC progenitors, into hIECs, is illustrated in FIG. 1.

Example 1. Preparation of Human Intestinal Epithelial Cell Progenitors (hIEC Progenitors) from hPSCs For hPSCs, human embryonic stem cells (hESCs; H9 hESCs, WiCell Research Institute, Madison, WI, USA) were used. The hPSCs were cultured in a medium containing Activin A, FBS, FGF4, and Wnt3A, to differentiate into endoderm (DE) and hindgut (HG). Then, the endoderm and the hindgut were transferred to and cultured in intestinal epithelial cell differentiation medium 1 (IEC differentiation medium 1) containing EGF, R-spondin 1 (R-spd1), and insulin, to induce differentiation into hIEC progenitors.

Specifically, first, to induce formation of endoderm (DE), the hPSCs were treated with 100 ng/ml of Activin A (R&D Systems, Minneapolis, MN, USA), and then cultured for 3 days in RPMI (Roswell Park Memorial Institute)-1640 medium (Thermo Fisher Scientific Inc.) supplemented with 0%, 0.2%, or 2% FBS. Thereafter, the cells were cultured in DMEM/F12 medium (Thermo Fisher Scientific Inc.), supplemented with 250 ng/ml of fibroblast growth factor 4 (FGF4; Peprotech, Rocky Hill, N.J., USA), 1.2 µM CHIR99021 (Tocris Bioscience, Minneapolis, Minn., USA), and 2% FBS, to further differentiate into hindgut (HG).

To differentiate the HG into human intestinal epithelial cell progenitors (hIEC progenitors), the HG was dispensed into a plate coated with 1% Matrigel and cultured in human intestinal epithelial cell differentiation medium 1 (hIEC differentiation medium 1). The hIEC differentiation medium 1 contained DMEM/F12, 100 ng/ml of epithelial growth factor (EGF), 100 ng/ml of R-spondin 1 (Peprotech), 5 µg/ml of insulin (Thermo Fisher Scientific Inc.), 2% FBS, 2% B27 supplement (Thermo Fisher Scientific Inc.), 1% Na supplement (Thermo Fisher Scientific Inc.), 2 mM L-glutamine (Thermo Fisher Scientific Inc.), 1% NEAA, and 15 mM HEPES buffer (Thermo Fisher Scientific Inc.). Replacement of the hIEC differentiation medium 1 was performed every other day, and the hIEC progenitors were passaged every 7 days.

Morphological differences between the hPSCs, the DE, the HG, and the hIEC progenitors were identified through a microscope. As a result, it was identified that the hPSCs were differentiated, via the DE and the HG, into the hIEC progenitors, through sequential treatment using growth factors such as Activin A, FGF4, and CHIR99021 that is a GSK3β inhibitor (FIG. 3).

In addition, it was identified whether in a case where hIEC progenitors (which had been passaged 6 times, p6) were subjected to freezing and thawing, such freezing and thawing affected morphological properties of the hIEC progenitors. As a result, no significant morphological difference was observed between the hIEC progenitors after thawing and the hIEC progenitors before freezing.

Experimental Example 1. Identification of Effects of Components (R-Spondin 1 and Insulin) in hIEC Differentiation Medium 1

In Example 1, to identify effects, on differentiation of the hPSCs into the hIEC progenitors, of R-spondin 1, which is an agonist of Wnt signaling, and insulin in composition of the hIEC differentiation medium 1, expression levels of marker genes related to intestinal epithelial cells were checked through qPCR analysis.

Specifically, total RNA and cDNA were prepared using RNeasy kit (Qiagen) and Superscript IV cDNA synthesis kit (Thermo Fisher Scientific Inc.), respectively. qPCR was performed using a 7500 Fast real-time PCR system (Applied Biosystems, Foster City, CA, USA). The primers used are shown in Table 1 below.

Figure 2:
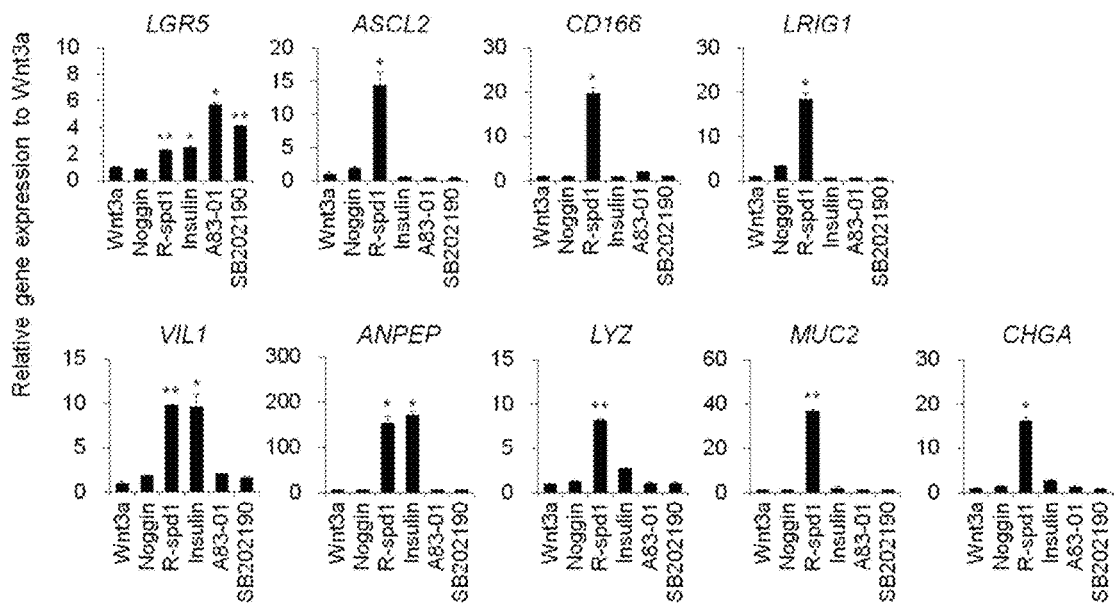
FIG. 2 illustrates graphs, showing expression levels of LGR5, ASCL2, CD166, LRIG1, VIL1, ANPEP, LYZ, MUC2, and CHGA genes upon treatment with R-spondin 1 (R-spd1) or insulin during differentiation of hPSCs.

ANPEP), secretory lineage cells (Paneth cells (LYZ), goblet cells (MUC2), enteroendocrine cells (CHGA)). In addition, it was identified that insulin increased expression of VIL1 and ANPEP (FIG. 2).

From these results, it was identified that R-spondin 1 increased differentiation of the pluripotent stem cells, thereby enhancing their differentiation into cell types of all lineages which make up the intestinal epithelium, and that insulin increases differentiation of pluripotent stem cells into absorptive cells. That is, it was identified that the hIEC differentiation medium 1 containing R-spondin 1 and insulin caused production of intestinal cell types found in vivo and at the same time, resulted in increased differentiation of the pluripotent stem cells into hIEC progenitors.

Experimental Example 2. Identification of Changes in Characteristics of hIEC Progenitors, Depending on Passage and Culture in Transwell The hIEC progenitors differentiated in Example 1 and the hIEC progenitors re-dispensed in Transwell, were passaged 2, 4, 6, 8, and 10 times. Then, the expression levels of marker genes related to intestinal epithelial cells and the number of viable cells were measured. As controls, hPSCs, Caco-2 cell line (ATCC), which is a human intestinal

TABLE 1

| Target gene | Primer (Forward) | SEQ ID NO | Primer (Reverse) | SEQ ID NO |
|---|---|---|---|---|
| LGR5 | TGCTCTTCACCAACTGCATC | 1 | CTCAGGCTCACCAGATCCTC | 2 |
| ASCL2 | CGTGAAGCTGGTGAACTTGG | 3 | GGATGTACTCCACGGCTGAG | 4 |
| CD166 | TCAAGGTGTTCAAGCAACCA | 5 | CTGAAATGCAGTCACCCAAC | 6 |
| LRIG1 | GACCCTTTCTGACCGACAA | 7 | CGCTTTCCACGGCTCTTT | 8 |
| CDX2 | CTGGAGCTGGAGAAGGAGTTTC | 9 | ATTTTAACCTGCCTCTCAGAGAGC | 10 |
| VIL1 | AGCCAGATCACTGCTGAGGT | 11 | TGGACAGGTGTTCCTCCTTC | 12 |
| ANPEP | AAGCCTGTTTCCTCGTTGTC | 13 | AACCTCATCCAGGCAGTGAC | 14 |
| SI | GGTAAGGAGAAACCGGGAAG | 15 | GCACGTCGACCTATGGAAAT | 16 |
| LYZ | AAAACCCCAGGAGCAGTTAAT | 17 | CAACCCTCTTTGCACAAGCT | 18 |
| MUC2 | TGTAGGCATCGCTCTTCTCA | 19 | GACACCATCTACCTCACCCG | 20 |
| CHGA | TGACCTCAACGATGCATTTC | 21 | CTGTCCTGGCTCTTCTGCTC | 22 |

As a result, it was identified that R-spondin 1 increased expression of markers of major cell types in the intestinal epithelium, including intestinal stem cells (ISCs) (LGR5, ASCL2, CD166, and LRIG1), enterocytes (VIL1 and epithelial cell model, and RNA from human small intestine (hSI) tissue (Clonetech) were used. qPCR was performed in the same manner as in Experimental Example 1, and the primers used are shown in Table 2 below.

TABLE 2

| Target gene | Primer (Forward) | SEQ ID NO | Primer (Reverse) | SEQ ID NO |
|---|---|---|---|---|
| CDX2 | CTGGAGCTGGAGAAGGAGTTTC | 9 | ATTTTAACCTGCCTCTCAGAGAGC | 10 |
| VIL1 | AGCCAGATCACTGCTGAGGT | 11 | TGGACAGGTGTTCCTCCTTC | 12 |
| SI | GGTAAGGAGAAACCGGGAAG | 15 | GCACGTCGACCTATGGAAAT | 16 |
| ZO-1 | CCCGACCATTTGAACGCAAG | 23 | ATGCCCATGAACTCAGCACG | 24 |

TABLE 2-continued

| Target gene | Primer (Forward) | SEQ ID NO | Primer (Reverse) | SEQ ID NO |
|---|---|---|---|---|
| OCLN | CATTGCCATCTTTGCCTGTG | 25 | AGCCATAACCATAGCCATAGC | 26 |
| CLDN1 | CCCAGTCAATGCCAGGTACG | 27 | GGGCCTTGGTGTTGGGTAAG | 28 |
| CLDN3 | CAGGCTACGACCGCAAGGAC | 29 | GGTGGTGGTGGTGGTGTTGG | 30 |
| CLDN5 | GCAGCCCTGTGAAGATTGA | 31 | GTCTCTGGCAAAAAGCGGTG | 32 |

Figure 4:
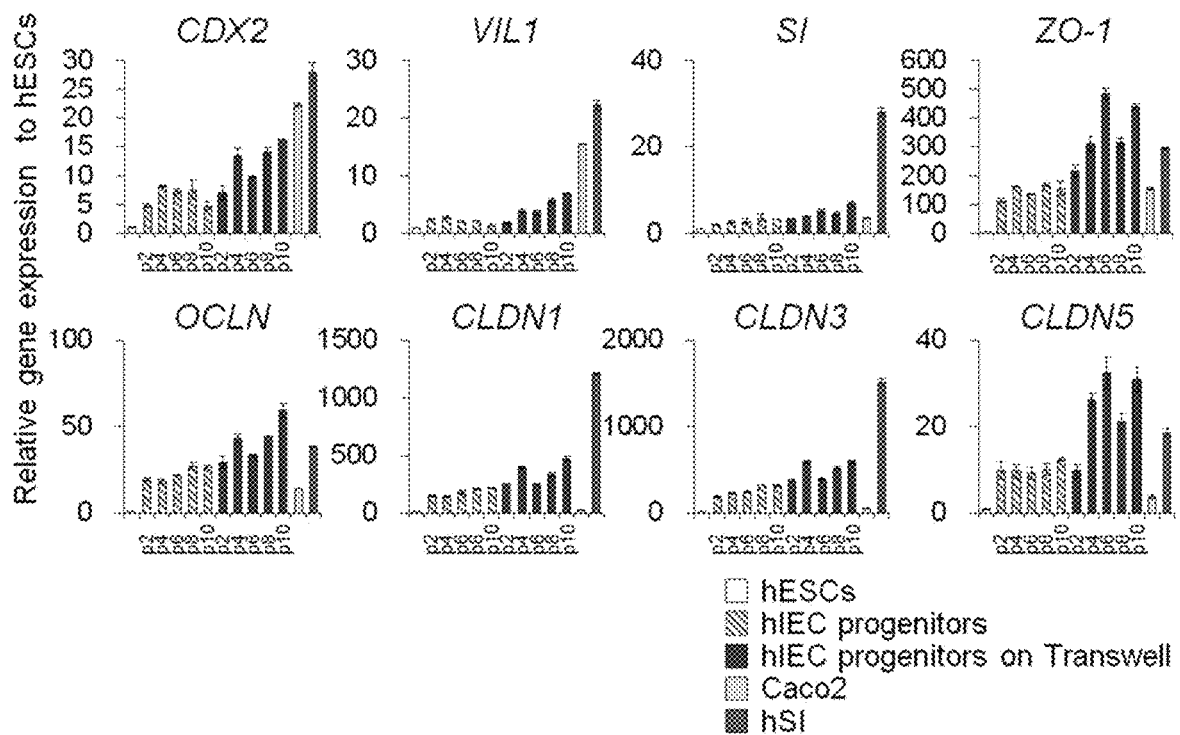
FIG. 4 illustrates graphs, showing expression levels of intestinal epithelial cell marker genes (CDX2, VIL1, SI, ZO-1, OCLN, CLDN1, CLDN3, CLDN5), depending on the number of passages, in hIEC progenitors.

As a result, it was identified that in the hIEC progenitors, expression of the marker genes for intestinal cells and tight junction molecules was stably maintained without significant changes (passages: >10, culture period: >5 months). In the hIEC progenitors passaged in Transwell, among the marker genes for intestinal cells and tight junction molecules, the ZO-1, OCLN, and CLDN5 genes exhibited significantly increased expression (FIG. 4). In addition, in the passaged hIEC progenitors, the number of viable cells was measured. As a result, the number of viable cells increased as the number of passages and the culture period increased (FIG. 5).

Furthermore, to identify the barrier function of the hIEC progenitors passaged in Transwell, the transepithelial electric resistance (TEER) values were continuously measured during the passage period. Here, the measurement of TEER was performed using an epithelial tissue volt-ohm-meter (EVOM2, WPI, Sarasota, FL, USA) according to the manufacturer's manual.

Figure 6:
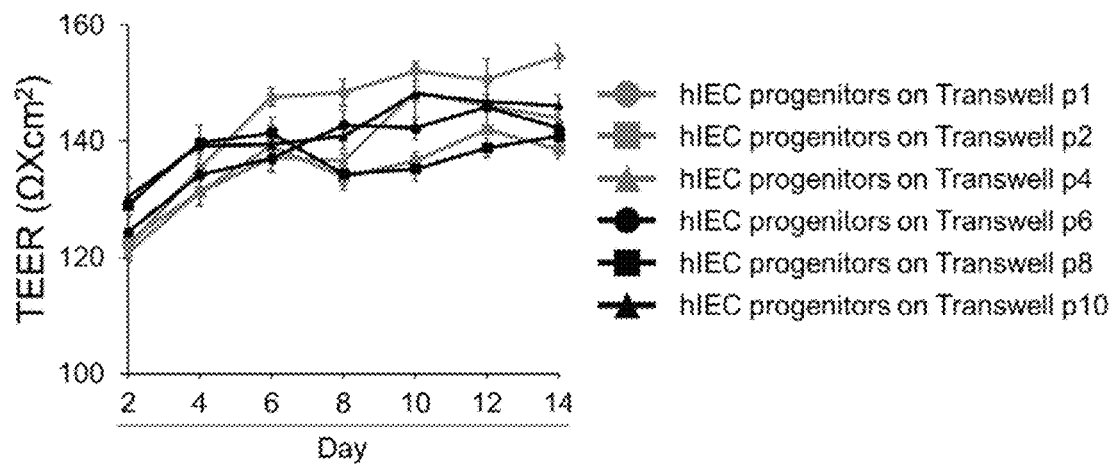
FIG. 6 illustrates a graph, showing transepithelial electric resistance (TEER) values of hIEC progenitors, obtained in a case where the hIEC progenitors are passaged in Transwell.

As a result, for the hIEC progenitors passaged in Transwell, their TEER value was about 144.39±0.81 Ω*cm$^2$ on day 14, and no significant change was observed depending on the number of passages (FIG. 6).

Example 2. Preparation of Functional Human Intestinal Epithelial Cells (Functional hIECs) from hIEC Progenitors To differentiate the hIEC progenitors in Example 1 into functional hIECs, the hIEC progenitor at 1.34×10$^5$ cells/cm$^2$ were re-dispensed in Transwell (Corning) coated with 1% Matrigel, and cultured for 2 days using the hIEC differentiation medium 1 supplemented with 10 µM Y-27632 (Tocris). Then, the medium was replaced with human intestinal epithelial cell differentiation medium 2 (hIEC differentiation medium 2) that contains DMEM/F12, 100 ng/ml of EGF, 2 µM Wnt-059 (Selleckchem, Huston, TX, USA), 1 mM valproic acid (Stemgent, Huston, TX, USA), 2% FBS, 2% B27 supplement, 1% N2 supplement, 2 mM L-glutamine, 1% NEAA, and 15 mM HEPES buffer (Thermo Fisher Scientific Inc.). Replacement of the hIEC differentiation medium 2 was performed every other day, and the functional hIECs were cultured for 10 to 14 days for further analysis.

Comparative Example 1. Differentiation of Immature Human Intestinal Epithelial Cells (Immature hIECs) from hIEC Progenitors To differentiate the hIEC progenitors in Example 1 into immature human intestinal epithelial cells (immature hIECs), the hIEC progenitors at 1.34×10$^5$ cells/cm$^2$ were re-dispensed in Transwell (Corning) coated with 1% Matrigel, and cultured for 2 days using the hIEC differentiation medium 1 supplemented with 10 µM Y-27632 (Tocris). Then, the medium was replaced with the hIEC differentiation medium 1. Replacement of the medium was performed every other day, and the immature hIECs were cultured for 10 to 14 days for further analysis.

The morphological differences between the immature hIECs and the functional hIECs in Example 1 were identified through a microscope. As a result, it was identified that the functional hIECs have a higher cell density than the immature hIECs, and the functional hIECs have a similar shape to the polygonal epithelium (FIG. 3).

Experimental Example 3. Identification of Effects of Components (Wnt-059 and Valproic Acid) in hIEC Differentiation Medium 2

To identify effects of Wnt-059 and valproic acid, which belong to the components of the hIEC differentiation medium 2 in Example 2, on the Wnt pathway and the Notch pathway during differentiation of hIEC progenitors into functional hIECs, expression levels of ATOH1, HES1, AXN2, and CTNNB1 genes in human small intestine (hSI) tissue, immature hIECs, and functional hIECs were checked through qPCR analysis. Here, inactivation of the Wnt pathway and activation of the Notch pathway inhibited differentiation of ISCs into secretory cells. qPCR was performed in the same manner as in Experimental Example 1, and the primers used are shown in Table 3 below.

TABLE 3

| Target gene | Primer (Forward) | SEQ ID NO | Primer (Reverse) | SEQ ID NO |
|---|---|---|---|---|
| ATOH1 | GTCCGAGCTGCTACAAACG | 33 | GTGGTGGTGGTCGCTTTT | 34 |
| HES1 | AGTGAAGCACCTCCGGAAC | 35 | CGTTCATGCACTCGCTGA | 36 |
| AXIN2 | GAGTGGACTTGTGCCGACTTCA | 37 | GGTGGCTGGTGCAAAGACATAG | 38 |
| CTNNB1 | TCTGAGGACAAGCCACAAGATTACA | 39 | TGGGCACCAATATCAAGTCCAA | 40 |

As a result, it was identified that the functional hIECs showed decreased expression levels of ATOH1 and Wnt target genes, such as AXIN2 and CTNNB1, as compared with the immature hIECs, whereas the functional hIECs showed an increased expression level of HES1, which is Notch target gene, as compared with the immature hIECs (FIG. 7). From these results, it was identified that Wnt-059 and valproic acid inhibited the Wnt pathway and activated the Notch pathway in the functional hIECs.

Experimental Example 4. Identification of Characteristics of Functional hIECs as Human Intestinal Epithelial Model Experimental Example 4.1. Identification I of Expression of Marker Genes Related to Intestinal and Secretory Cells in Functional hIECs The expression levels of marker genes related to intestinal and secretory cells in hPSCs, immature hIECs, functional hIECs, and Caco-2 cell line were checked through qPCR analysis. qPCR was performed in the same manner as in Experimental Example 1, and the primers used are shown in Table 4 below.

TABLE 4

| Target gene | Primer (Forward) | SEQ ID NO | Primer (Reverse) | SEQ ID NO |
|---|---|---|---|---|
| LGR5 | TGCTCTTCACCAACTGCATC | 1 | CTCAGGCTCACCAGATCCTC | 2 |
| ASCL2 | CGTGAAGCTGGTGAACTTGG | 3 | GGATGTACTCCACGGCTGAG | 4 |
| CD166 | TCAAGGTGTTCAAGCAACCA | 5 | CTGAAATGCAGTCACCCAAC | 6 |
| LRIG1 | GACCCTTTCTGACCGACAA | 7 | CGCTTTCCACGGCTCTTT | 8 |
| CDX2 | CTGGAGCTGGAGAAGGAGTTTC | 9 | ATTTTAACCTGCCTCTCAGAGAGC | 10 |
| SOX9 | GGAGAGCGAGGAGGACAAGTTC | 11 | TTGAAGATGGCGTTGGGGG | 12 |
| ISX | CAGGAAGGAAGGAAGAGCAA | 13 | TGGGTAGTGGGTAAAGTGGAA | 14 |
| VIL1 | AGCCAGATCACTGCTGAGGT | 15 | TGGACAGGTGTTCCTCCTTC | 16 |
| ANPEP | AAGCCTGTTTCCTCGTTGTC | 17 | AACCTCATCCAGGCAGTGAC | 18 |
| SI | GGTAAGGAGAAACCGGGAAG | 19 | GCACGTCGACCTATGGAAAT | 20 |
| LYZ | AAAACCCCAGGAGCAGTTAAT | 21 | CAACCCTCTTTGCACAAGCT | 22 |
| MUC2 | TGTAGGCATCGCTCTTCTCA | 23 | GACACCATCTACCTCACCCG | 24 |
| CHGA | TGACCTCAACGATGCATTTC | 25 | CTGTCCTGGCTCTTCTGCTC | 26 |
| MUC13 | CGGATGACTGCCTCAATGGT | 83 | AAAGACGCTCCCTTCTGCTC | 84 |

As a result, it was identified that as compared with the immature hIECs, the functional hIECs showed significantly increased mRNA expression levels of major intestinal cell-specific markers related to intestinal transcription factors (CDX2, SOX9, ISX, SI), intestinal cells (VIL1, ANPEP), and secretory lineage cells such as Paneth cells (LYZ), goblet cells (MUC2), and enteroendocrine cells (CHGA) (FIG. 8).

Experimental Example 4.2. Identification II of Expression of Marker Genes Related to Intestinal and Secretory Cells in Functional hIECs In the immature hIECs, the functional hIECs, and the Caco-2 cell line, the expression levels of CDX2, VILLIN (VIL1), LYZ, MUC2, and CHGA were checked through immunofluorescence staining.

For the immunofluorescence staining, the respective cells were washed, fixed with 4% paraformaldehyde, cryopreserved with 10% to 30% sucrose, and embedded in an OCT compound. For a vertical section, the frozen tissue block was cut to a thickness of 10 μm using a cryostat-microtome at −30° C. Then, the cells were treated with PBS containing 0.1% Triton-X 100, and a blocking process was performed with 4% BSA. Reaction with primary antibodies was carried out overnight at 4° C. The next day, the cells were washed with PBS containing 0.05% Tween 20 (Sigma-Aldrich), and incubated with secondary antibodies (Donkey anti-mouse IgG Alexa Fluor 594 (A21203), Chicken anti-rabbit IgG Alexa Fluor 594 (A21442), Chicken anti-goat IgG Alexa Fluor 488 (A21467), Chicken anti-rabbit IgG Alexa Fluor 488 (A21441), Thermo Fisher Scientific Inc.). Then, images were taken using a confocal microscope (LSM800, Carl Zeiss, Oberkochen, Germany) and a fluorescence microscope (IX51, Olympus, Japan). The nuclei in the cells were stained with DAPI (1 mg/ml, Thermo Fisher Scientific Inc.). The primary antibodies used are shown in Table 5 below.

TABLE 5

| Antibodies | Catalog No. | Company | Dilution |
|---|---|---|---|
| anti-CDX2 | ab15258 | abcam | 1:100 |
| anti-Villin1 | sc-7672 | Santa Cruz | 1:50 |
| anti-Mucin2 | sc-7314 | Santa Cruz | 1:50 |
| anti-Lysozyme | ab76784 | abcam | 1:200 |
| anti-Chromogranin A | MA5-14536 | Thermo Scientific | 1:100 |

Figure 9:
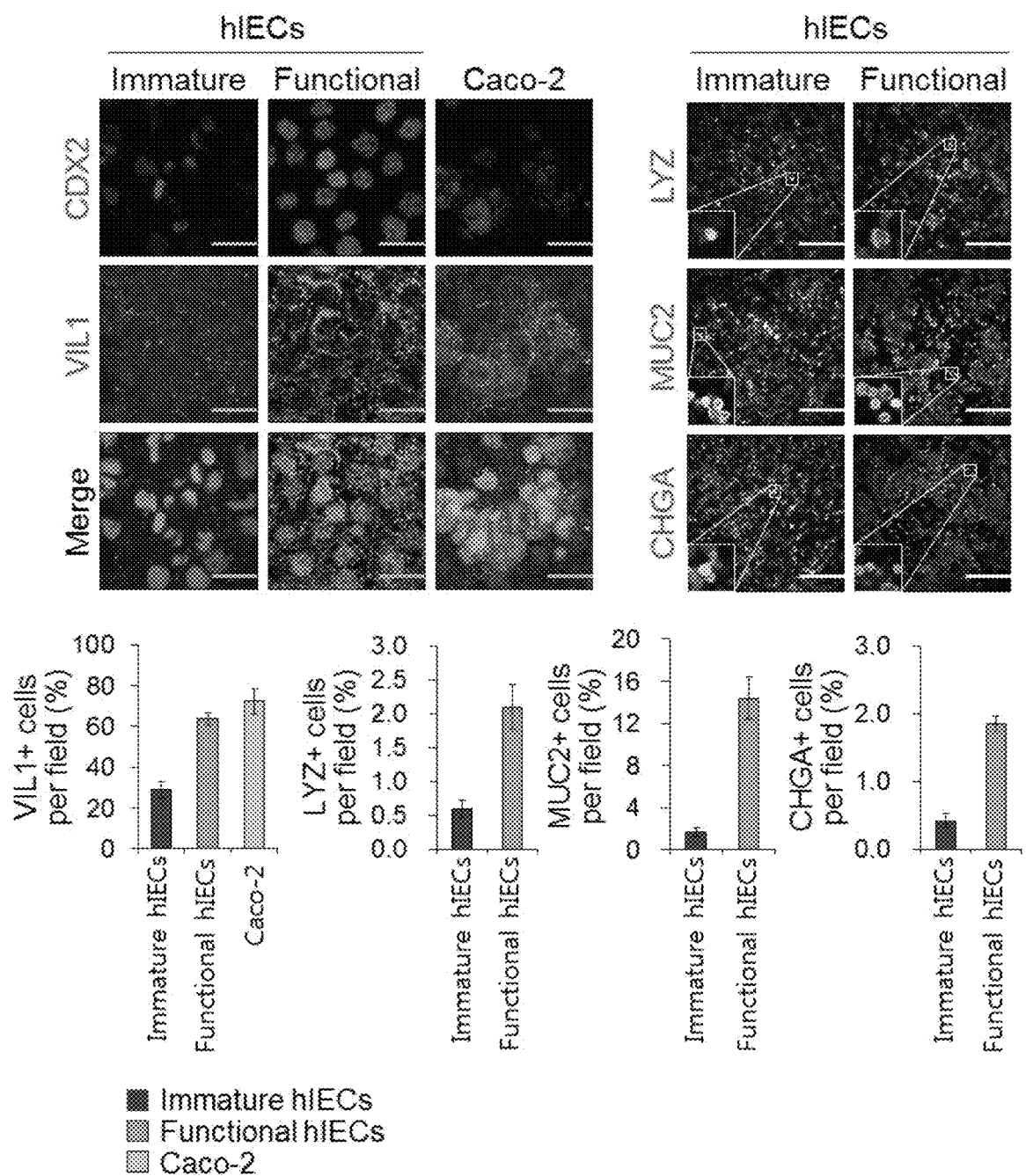
FIG. 9 illustrates results obtained by identifying, through immunofluorescence staining, expression levels of CDX2 and VILLIN (VIL1) in immature hIECs and functional hIECs.

As a result, it was identified that the functional hIECs showed increased expression of VIL1, as compared with the immature hIECs and the Caco-2 cell line (FIG. 9). It was found that the proportion of VIL1-positive cells in the immature hIECs was about 30%, whereas the proportion of VIL1-positive cells in the functional hIECs was about 60% similar to that in the Caco-2 cell line. In addition, it was identified that the functional hIECs showed significantly increased expression of CHGA, MUC2, and LYZ, as compared with the immature hIECs.

Experimental Example 4.3. Identification of Expression of Tight Junction Markers in Functional hIECs The expression levels of tight junction genes in hSI, hESCs, immature hIECs, and functional hIECs were checked through qPCR analysis. qPCR was performed in the same manner as in Experimental Example 1, and the primers used are shown in Table 6 below.

TABLE 6

| Target gene | Primer (Forward) | SEQ ID NO | Primer (Reverse) | SEQ ID NO |
|---|---|---|---|---|
| ZO-1 | CCCGACCATTTGAACGCAAG | 23 | ATGCCCATGAACTCAGCACG | 24 |
| OCLN | CATTGCCATCTTTGCCTGTG | 25 | AGCCATAACCATAGCCATAGC | 26 |
| CLDN1 | CCCAGTCAATGCCAGGTACG | 27 | GGGCCTTGGTGTTGGGTAAG | 28 |
| CLDN3 | CAGGCTACGACCGCAAGGAC | 29 | GGTGGTGGTGGTGGTGTTGG | 30 |
| CLDN5 | GCAGCCCCTGTGAAGATTGA | 31 | GTCTCTGGCAAAAGCGGTG | 32 |
| CLDN4 | GGCTGCTTTGCTGCAACTGTC | 85 | GAGCCGTGGCACCTTACACG | 86 |
| CLDN7 | CCATGACTGGAGGCATCATTT | 87 | GACAATCTGGTGGCCATACCA | 88 |
| CLDN15 | CATCACCACCAACACCATCTT | 89 | GCTGCTGTCGCCTTCTTGGTC | 90 |

As a result, the functional hIECs showed significantly high expression levels of OCLN, CLDN1, CLDN3, CLDN5, and ZO-1, which are tight junction genes, as compared with the immature hIECs (FIG. 10).

In addition, the expression level of the ZO-1 protein was checked through immunofluorescence staining in the same manner as in Experimental Example 4.2, and the primary antibodies used are shown in Table 7 below.

TABLE 7

| Antibodies | Catalog No. | Company | Dilution |
|---|---|---|---|
| anti-ZO-1 | 61-7300 | Thermo Fisher Scientific | 1:50 |

Figure 11:
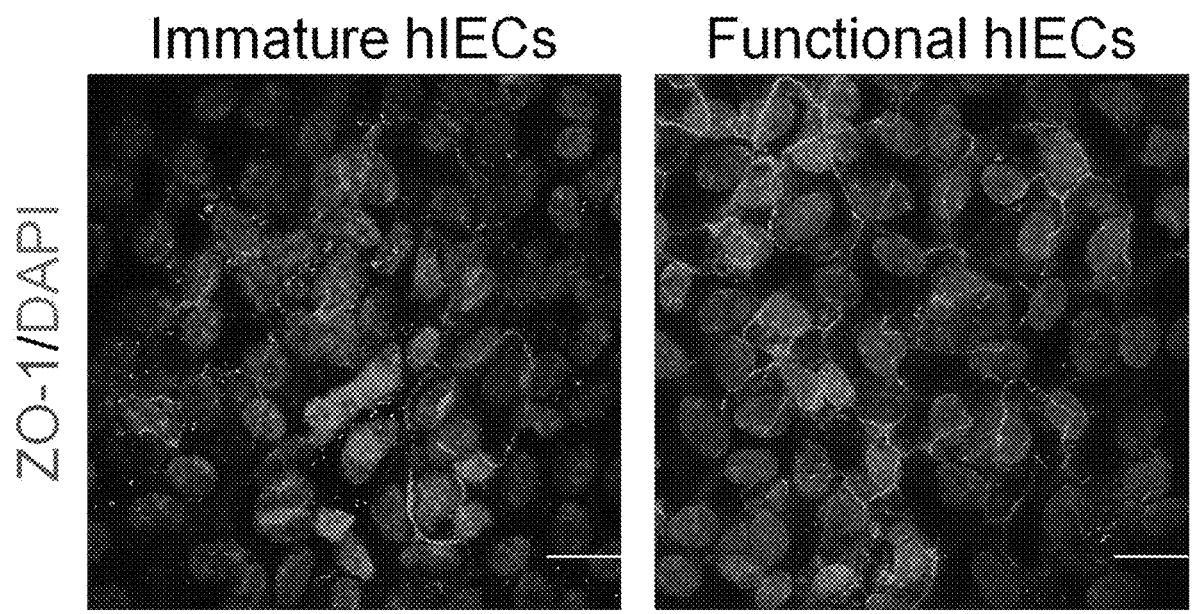
FIG. 11 illustrates results obtained by identifying, through immunofluorescence staining, expression of ZO-1 protein in immature hIECs and functional hIECs.

In addition, it was observed that the functional hIECs showed a high expression level of the ZO-1 protein as compared with the immature hIECs (FIG. 11).

Experimental Example 4.4. Identification of Barrier Function of Functional hIECs For the immature hIECs in Comparative Example 1, the functional hIECs in Example 2, and the Caco-2 cell line, their barrier function was identified by continuously measuring transepithelial electrical resistance (TEER) values during the passage period. Here, the measurement of TEER was performed using an epithelial tissue volt-ohm-meter (EVOM2, WPI, Sarasota, Fla., USA) according to the manufacturer's manual.

Figure 12:
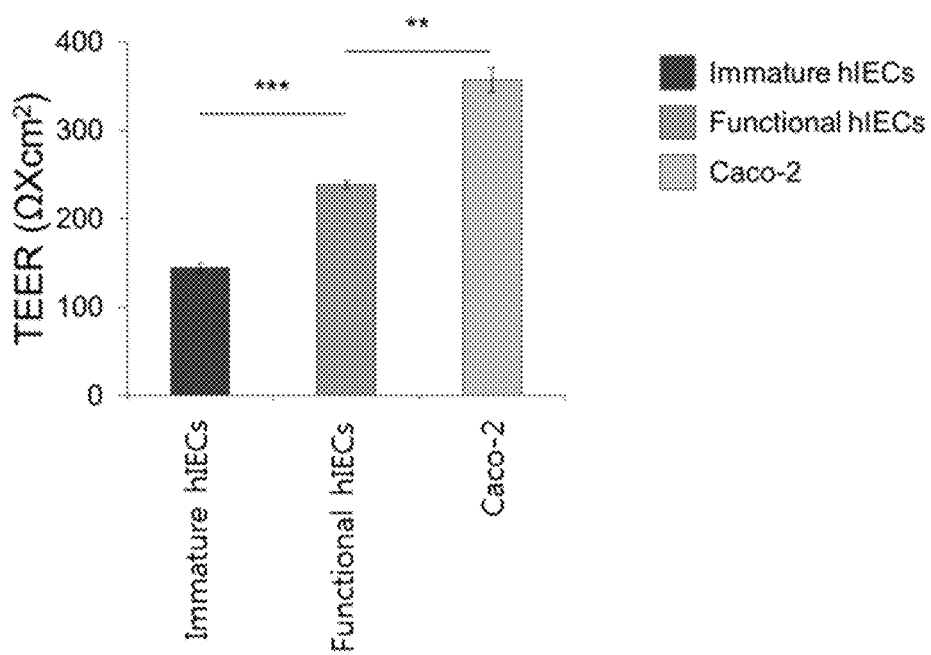
FIG. 12 illustrates a graph (a) which shows a transepithelial electric resistance (TEER) value of immature hIECs and functional hIECs, and a graph (b) which shows changes of TEER value, depending on days of culture for passages, in functional hIECs.
Figure 12:
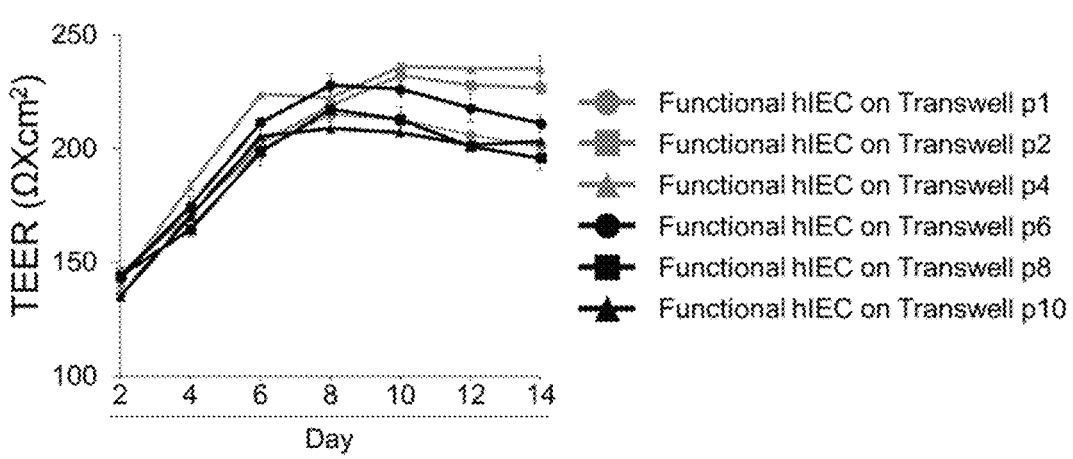

As a result, the TEER value of the Caco-2 cell line was measured as $357.28 \pm 13.76$ $\Omega^*cm^2$; the TEER value of the immature hIECs was measured as $137.76 \pm 4.77$ $\Omega^*cm^2$; and the TEER value of the functional hIECs was measured as $238.56 \pm 4.08$ $\Omega^*cm^2$. From these results, it was identified that the TEER value of the functional hIECs was higher than that of the immature hIECs (FIG. 12a). In addition, it was identified that the TEER value was kept constant within the range of $203.28 \pm 0.56$ $S2^*cm^2$ at minimum and $235.20 \pm 5.60$ $S2^*cm^2$ at maximum regardless of whether the passage was performed (FIG. 12b).

Experimental Example 4.5. Identification of Expression of Marker Genes Related to Apical Side and Basolateral Side of Cell Membrane in Functional hIECs For the immature hIECs in Comparative Example 1 and the functional hIECs in Example 2, the expression levels of VIL1, which is a marker gene related to the apical side of the cell membrane, and $Na^+$—$K^+$ ATPase, which is a marker gene related to the basolateral side of the cell membrane, were checked through immunofluorescence staining in the same manner as in Experimental Example 4.2, and the primary antibodies used are shown in Table 8 below.

TABLE 8

| Antibodies | Catalog No. | Company | Dilution |
|---|---|---|---|
| anti-Villin1 | sc-7672 | Santa Cruz | 1:50 |
| anti-Na+—K+ ATPase | GTX30202 | Genetex | 1:100 |

Figure 13:
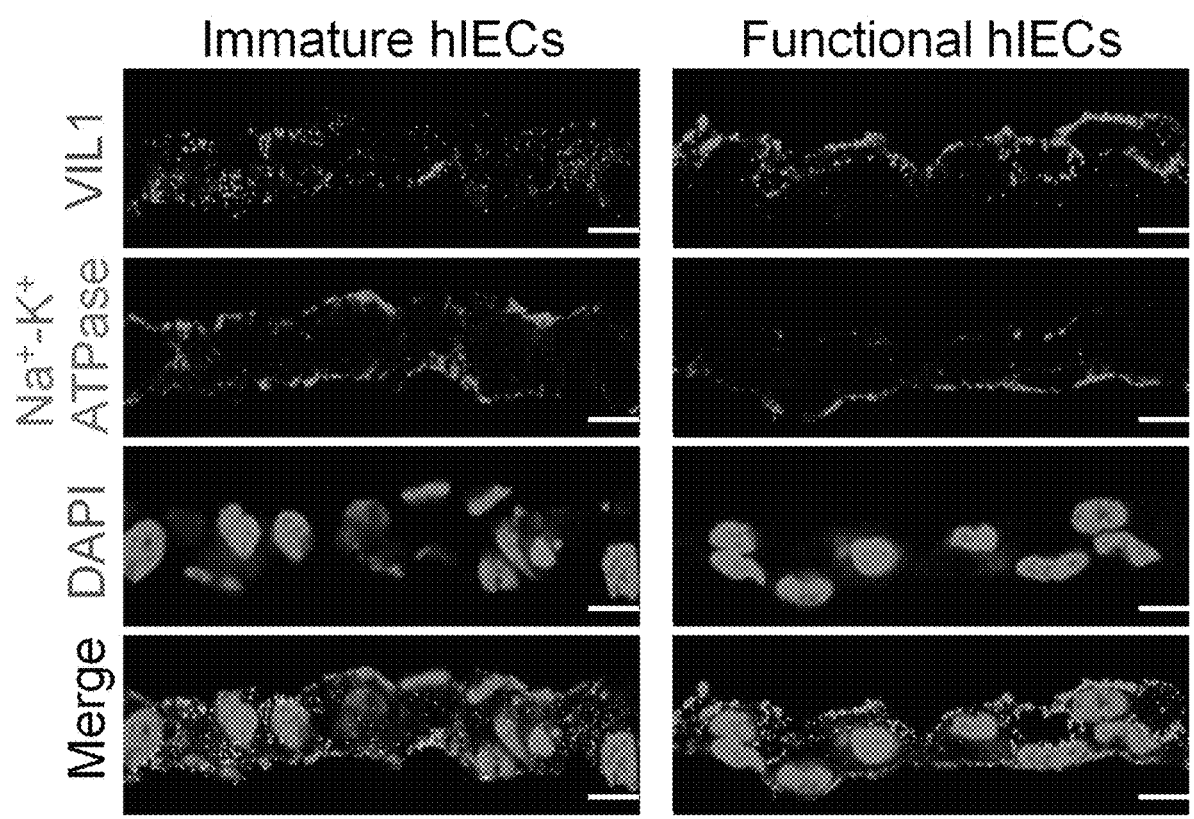
FIG. 13 illustrates results obtained by identifying, through immunofluorescence staining, expression levels of VIL1, which is a marker gene related to the apical side of the cell membrane, and $Na^+$—$K^+$ ATPase, which is a marker gene related to the basolateral side of the cell membrane, in immature hIECs and functional hIECs.

As a result, it was identified that as compared with the immature hIECs, the functional hIECs formed a structurally polarized monolayer in polarization distribution of the apical (VIL1) and basolateral ($Na^+$—$K^+$ ATPase) cell surface proteins (FIG. 13). From these results, it was identified that the functional hIECs had a superior barrier function to the immature hIECs.

Experimental Example 4.6. Identification of Enzyme Activity in Functional hIECs

An alkaline phosphatase, intestinal (ALPI) assay was performed on functional hIECs, to evaluate general functional characteristics observed in the functional hIECs. Specifically, in the hPSCs, the immature hIECs, the functional hIECs, and the Caco-2 cell line, the mRNA expression level of ALPI, which is a related enzyme, was evaluated through qPCR analysis. qPCR was performed in the same manner as in Experimental Example 1, and the primers used are shown in Table 9 below.

TABLE 9

| Target gene | Primer (Forward) | SEQ ID NO | Primer (Reverse) | SEQ ID NO |
|---|---|---|---|---|
| ALPI | CTCACTGAGGCGGTCATGTT | 81 | TAGGCTTTGCTGTCCTGAGC | 82 |

Figure 14:
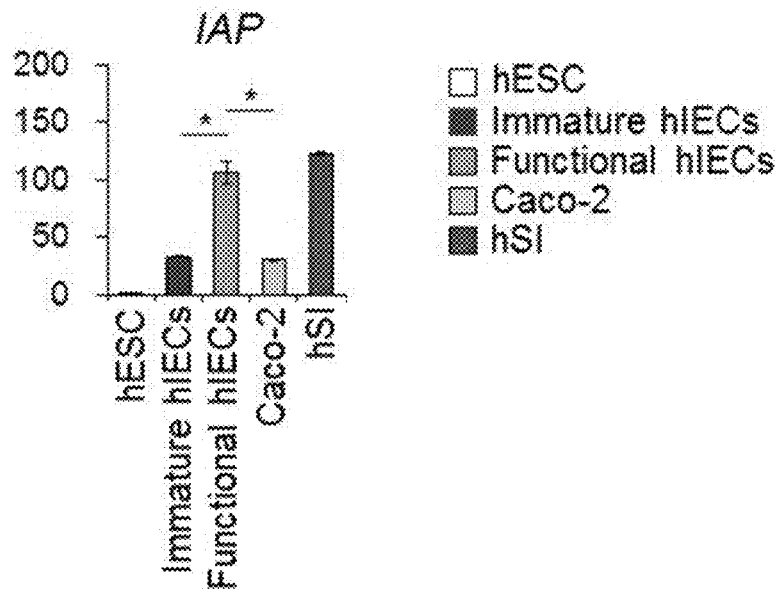
FIG. 14 illustrates a graph, showing an expression level of IAP gene in immature hIECs and functional hIECs.

As a result, the immature hIECs, the functional hIECs, and the Caco-2 cell line showed a significantly high mRNA expression level of ALPI as compared with the hPSCs; in particular, the functional hIECs showed a high mRNA expression level of ALPI as compared with the immature hIECs and the Caco-2 cell line (FIG. 14).

In addition, for the immature hIECs, the functional hIECs, and the Caco-2 cell line, the activity of ALPI was analyzed.

The activity of alkaline phosphatase was quantified using an alkaline phosphatase assay kit (ab83369, Abcam, Cambridge, UK) according to the manufacturer's manual. Here, each of the respective cell culture media was obtained from the corresponding cells on day 14, and diluted 1:10 with an assay buffer. 80 µl of sample and 50 µl of 5 mM para-nitrophenyl phosphate (pNPP) solution were well mixed and added to each well, and the plate was incubated at 25° C. for 60 minutes in the dark. Thereafter, 20 µl of stop solution was added to each well, and absorbance was measured at a wavelength of 405 nm using a Spectra Max M3 microplate reader (Molecular Devices, Sunnyvale, CA, USA).

Figure 15:
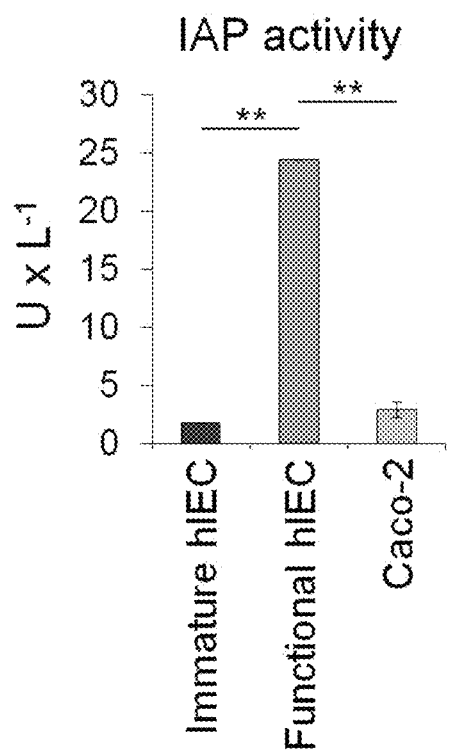
FIG. 15 illustrates a graph, showing activity of IAP enzyme in immature hIECs and functional hIECs.

As a result, it was identified that the functional hIECs showed significantly high activity of ALPI as compared with the immature hIECs and the Caco-2 cell line (FIG. 15).

Experimental Example 4.7. Identification of Expression of Intestinal Transporters and Metabolic Enzymes in Functional hIECs In the functional hIECs, the expression levels of various intestinal transporters and metabolic enzymes were evaluated. Specifically, in the hSI, the hPSCs, the immature hIECs, the functional hIECs and the Caco-2 cell line, the mRNA expression levels of intestinal transporter- and metabolic enzyme-related genes were evaluated through qPCR analysis. qPCR was performed in the same manner as in Experimental Example 1, and the primers used are shown in Table 10 below.

TABLE 10

| Target gene | Primer (Forward) | SEQ ID NO | Primer (Reverse) | SEQ ID NO |
|---|---|---|---|---|
| MDR1 | GCCAAAGCCAAAATATCAGC | 41 | TTCCAATGTGTTCGGCATTA | 42 |
| SGLT1 | GTGCAGTCAGCACAAAGTGG | 43 | ATGCACATCCGGAATGGGTT | 44 |
| GLUT2 | GGCCAGCAGGTTCATCATCAGCAT | 45 | CCTTGGGCTGAGGAAGAGACTGTG | 46 |
| GLUT5 | CGCCAAGAAAGCCCTACAGA | 47 | GCGCTCAGGTAGATCTGGTC | 48 |
| OSTPβ | TGATTGGCTATGGGGCTATC | 49 | CATATCCTCAGGGCTGGTGT | 50 |
| ASBT | TATAGGATGCTGCCCTGGAG | 51 | AGTGTGGAGCATGTGGTCAT | 52 |
| MCT1 | GCGATCCGCGCATATAAC | 53 | AACTGGACCTCCAACTGCTG | 54 |
| OCT1 | TAATGGACCACATCGCTCAA | 55 | AGCCCTGATAGAGCACAGA | 56 |
| OSTα | GAAGACCAATTACGGCATCC | 57 | AGTGAGGGCAAGTTCCACAG | 58 |
| OSTβ | GAGCTGCTGGAAGAGATGAT | 59 | TGCTTATAATGACCACCAGC | 60 |
| BCRP | TGCAACATGTACTGGCGAAGA | 61 | TCTTCCACAGCCCCAGG | 62 |
| MRP3 | GTCCGCAGAATGGACTTGAT | 63 | TCACCACTTGGGGATCATTT | 64 |
| GSTA | AGCCGGGCTGACATTCATCT | 65 | TGGCCTCCATGACTGCGTTA | 66 |
| SLC36A1 | TCTGCCGCAGGCTGAATAAA | 67 | GAGTCGCGAGTCCATGGTAG | 68 |
| SLC9A3 | CAGGATCCCTACGTCATCGC | 69 | GAAGTCCAGCAGCCCAATCT | 70 |
| SLC26A3 | GCACAGGAGGCAAAACACAG | 71 | TTGGGTCCTGAACACGATGG | 72 |
| CYP3A4 | CTGTGTGTTTCCAAGAGAAGTTAC | 73 | TGCATCAATTTCCTCCTGCAG | 74 |
| CYP3A5 | GCTCGCAGCCCAGTCAATA | 75 | AGGTGGTGCCTTATTGGGC | 76 |
| CYP2C9 | ATCAAGATTTTGAGCAGCCCC | 77 | AGGGTTGTGCTTGTCGTCTC | 78 |
| UGT1A1 | AACAAGGAGCTCATGGCCTCC | 79 | CCACAATTCCATGTTCTCCAG | 80 |
| ALPI | CTCACTGAGGCGGTCATGTT | 81 | TAGGCTTTGCTGTCCTGAGC | 82 |

Figure 16:
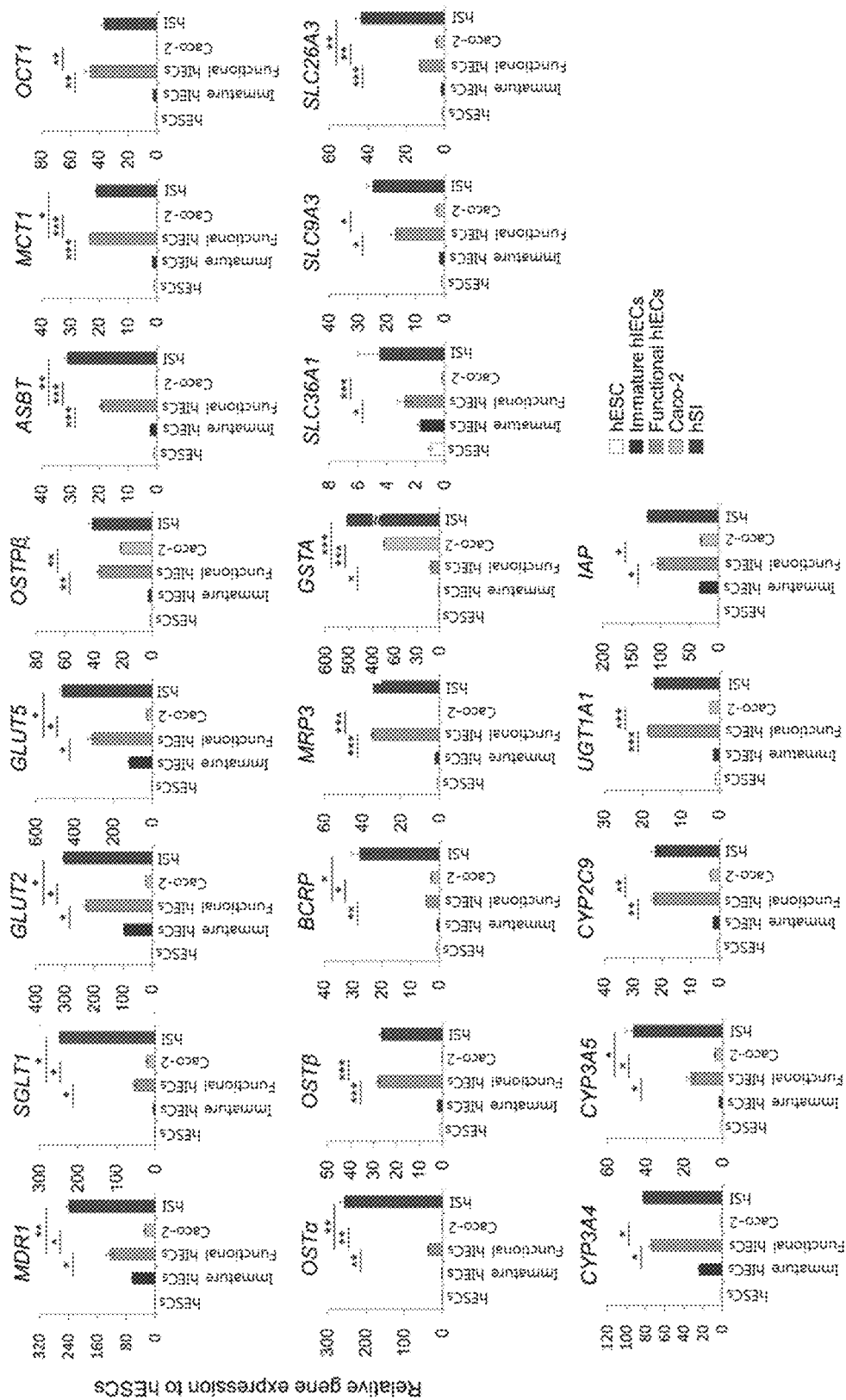
FIG. 16 illustrates a graph, showing expression levels of intestinal transporter- and metabolic enzyme-related genes in immature hIECs and functional hIECs.

As a result, it was identified that 21 genes were upregulated in the functional hIECs as compared with the immature hIECs (FIG. 16).

In addition, in line with high expression levels of SGLT, GLUT2, and GLUT5, which are genes encoding glucose transporters, it was evaluated whether in the immature hIECs, the Caco-2 cell line, and the functional hIECs, calcium ions are released from intracellular organelles including endoplasmic reticulum upon glucose stimulation.

Specifically, the functional hIECs, the immature hIECs, and the Caco-2 cell line were dispensed in a confocal glass-bottom dish, treatment with 5 µM Fluo-4 AM (Thermo Fisher Scientific Inc.) was performed, and reaction was allowed to proceed for 1 hour. Then, the respective cells were washed three times with a $Ca^{2+}$-free isotonic buffer (140 mM NaCl, 5 mM KCl, 10 mM HEPES, 5.5 mM D-glucose, and 2 mM $MgCl_2$). The washed respective cells were stimulated with 50 mM glucose (Sigma-Aldrich) in a $Ca^{2+}$-free isotonic buffer, excited at a wavelength of 488 nm, and the emitted wavelengths of 505 nm to 530 nm were recorded. Fluorescence intensity in the region of interest (ROI) was calculated using FV1000 software (Olympus).

Figure 17:
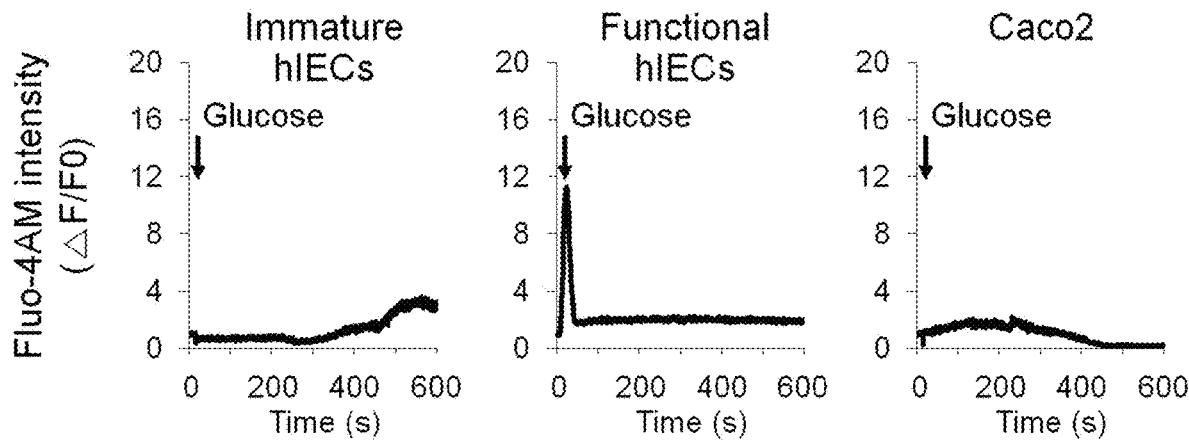
FIGS. 17 and 18 illustrate graphs, showing amounts of calcium ion released upon glucose stimulation in immature hIECs and functional hIECs.
Figure 18:
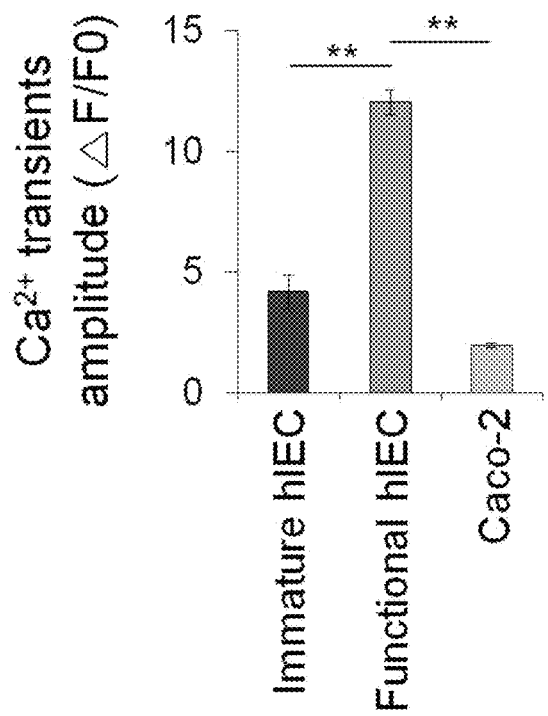

In line with high expression levels of SGLT, GLUT2, and GLUT5, which are genes encoding glucose transporters, more calcium ions were released from intracellular organelles including the endoplasmic reticulum upon glucose stimulation in the functional hIECs, than in the immature hIECs and the Caco-2 cell line (FIGS. 17 and 18). From these results, it was identified that the functional hIECs can absorb and deliver more nutrients such as glucose than the immature hIECs and the Caco-2 cell line.

Experimental Example 4.8. Identification of Expression and Activity of CYP3A4 in Functional hIECs Orally administered drugs are not only mainly metabolized in the liver, but also metabolized by cytochrome P450 in the small intestine. CYP3A4 plays an important role as a drug-metabolizing enzyme in the human intestinal epithelial cells; however, it is known that CYP3A4 is hardly expressed in hPSC-derived enterocytes and Caco-2 cell line. Accordingly, in the hESCs, the hSI, the immature hIECs, the functional hIECs, and the Caco-2 cell line, the expression level of CYP3A4 gene was checked through qPCR analysis. qPCR was performed in the same manner as in Experimental Example 1, and the primers used are shown in Table 11 below.

TABLE 11

| Target gene | Primer (Forward) | SEQ ID NO | Primer (Reverse) | SEQ ID NO |
|---|---|---|---|---|
| CYP3A4 | CTGTGTGTTTCCAAGA GAAGTTAC | 73 | TGCATCAATTTCCTCC TGCAG | 74 |

Figure 19:
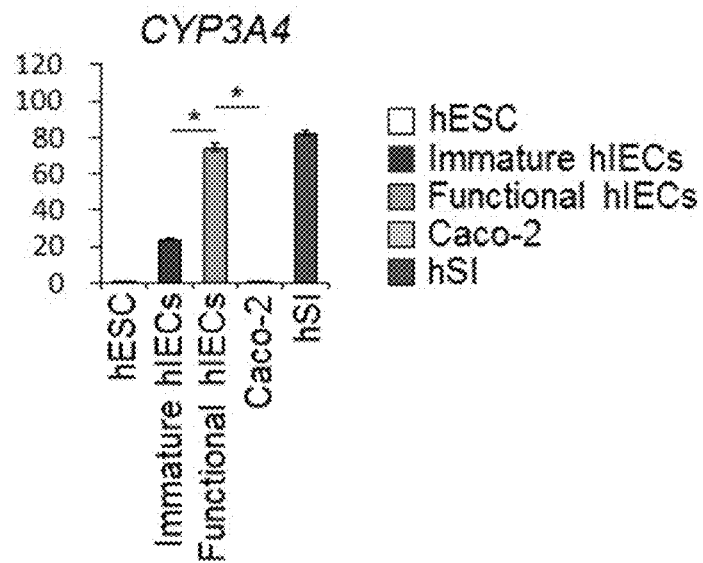
FIG. 19 illustrates a graph, showing an expression level of CYP3A4 gene in immature hIECs and functional hIECs.

As a result, it was identified that the functional hIECs showed an increased expression level of CYP3A4, as compared with the hESCs, the immature hIECs, and the Caco-2 cell line (FIG. 19). Specifically, the Caco-2 cell line showed an insignificant expression level of CYP3A4, and the immature hIECs showed a slightly higher expression level of CYP3A4. On the contrary, the functional hIECs showed a remarkably high expression level of CYP3A4, which was not significantly different from that in the hSI.

In addition, in the immature hIECs, the functional hIECs, and the Caco-2 cell line, the expression level of CYP3A4 protein and the proportion of CYP3A4-positive cells were analyzed through immunofluorescence staining. The immunofluorescence staining was performed in the same manner as in Experimental Example 4.2, and the primary antibodies used are shown in Table 12 below.

TABLE 12

| Antibodies | Catalog No. | Company | Dilution |
|---|---|---|---|
| anti-CYP3A4 | 13384S | Cell Signaling | 1:100 |

Figure 20:
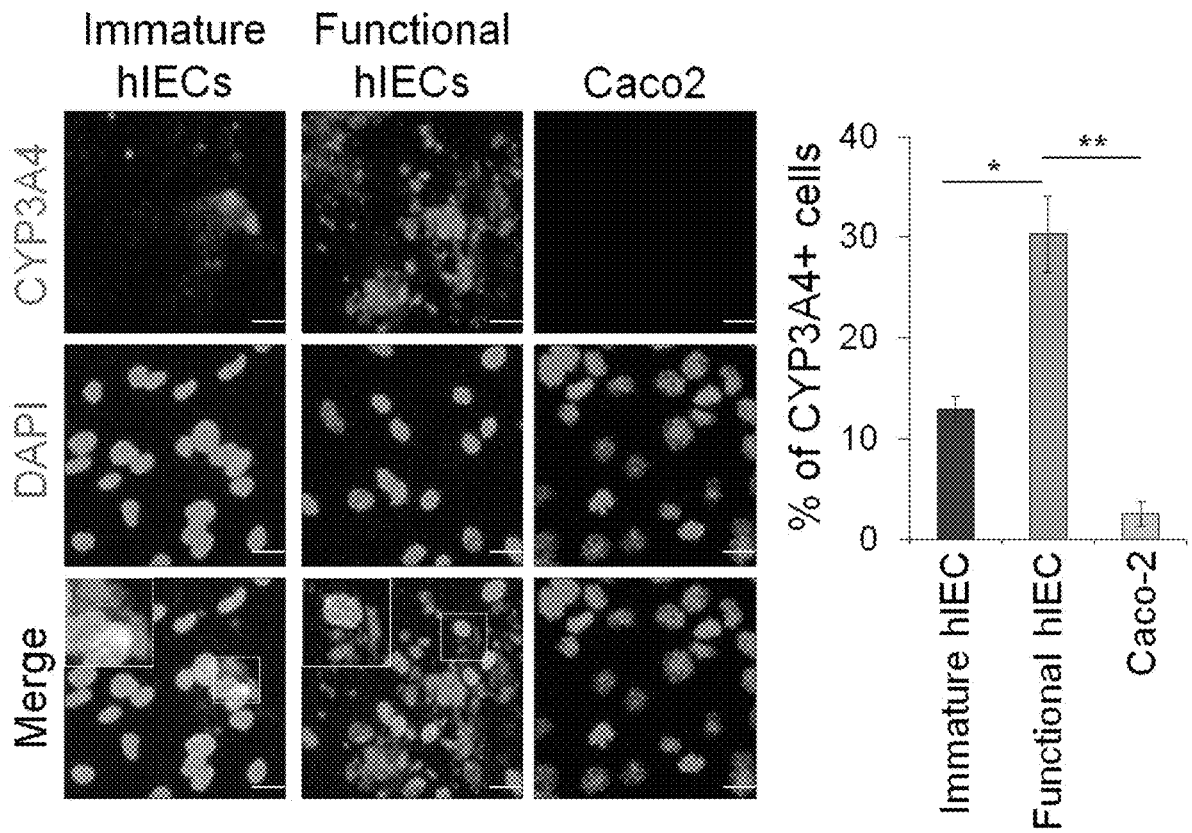
FIG. 20 illustrates results obtained by identifying, through immunofluorescence staining, an expression level of CYP3A4 in immature hIECs and functional hIECs.

As a result, the functional hIECs showed an increased expression level of CYP3A4 protein and an increased proportion of CYP3A4-positive cells, as compared with the immature hIECs and the Caco-2 cell line (FIG. 20).

Furthermore, in the immature hIECs, the functional hIECs, and the Caco-2 cell line, CYP3A4 enzyme activity was measured using a CYP3A4-Glo assay kit.

Specifically, the measurement was performed using a P450-Glo CYP3A4 assay kit (V9002; Promega, Madison, WI, USA) according to the manufacturer's manual. The immature hIECs, the functional hIECs, and the Caco-2 cell line, each of which had been cultured for 14 days, were treated with 3 µM Luciferin-IPA, and incubated at 37° C. for 60 minutes. The obtained supernatant was transferred to a 96-well plate. Then, the equal volume of luciferin detection reagent was added to each well and incubation was performed at room temperature for 20 minutes. Luminescence was measured using a Spectra Max M3 microplate reader.

Figure 21:
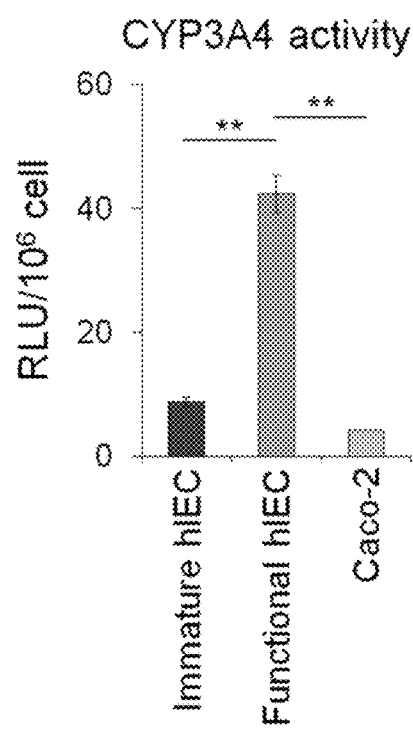
FIG. 21 illustrates a graph, showing activity of CYP3A4 enzyme in immature hIECs and functional hIECs.

As a result, it was identified that the functional hIECs showed significantly increased CYP3A4 enzyme activity as compared with the immature hIECs and the Caco-2 cell line (FIG. 21). From these results, it was identified that the functional hIECs showed excellent absorption of nutrients such as glucose and excellent drug biocompatibility.

Experimental Example 5. Transplantation Assay for Functional hIECs

Experimental Example 5.1. Identification of Active Histone Marks of Specific Genes in Functional hIECs Using Mouse Model Male BALB/c nude mice aged 6 to 7 weeks were purchased from Jackson Laboratory (Bar Harbor, ME, USA). All mice were kept in a standard animal housing facility under 12-hour light and 12-hour dark condition. For subcutaneous injection, the immature hIECs or functional hIECs at $5 \times 10^6$ to $1 \times 10^7$ cells were mixed with 200 µl of Matrigel and transplanted subcutaneously into the mice. The transplantation was monitored over 6 to 10 weeks. The resulting immature hIEC-Matrigel or functional hIEC-Matrigel plug was surgically removed from the mice and fixed with 10% formaldehyde. The hIEC-Matrigel plug was embedded in an OCT compound (optimal cutting temperature, Sakura® Finetek, Tokyo, Japan). Then, it was cut into a thickness of 10 µm using a cryostat-microtome at −30° C. All animal studies were approved by the Institutional Animal Care and Use Committee (IACUC) of the Korea Research Institute of Bioscience and Biotechnology (Approval No.: KRIBB-AEC-19110).

To characterize the functional hIECs at the epigenetic level, a chromatin immunoprecipitation (ChIP) assay was performed using antibodies against histone 3 lysine 4 trimethylation (H3K4me3) and histone 3 lysine 27 acetylation (H3K27ac), which are active histone marks related to active lineage-specific genes.

Specifically, the ChIP assay was performed with a Magna ChIP A/G kit (Magna0013 and Magna0014; Millipore, Billerica, MA, USA) according to the manufacturer's manual. The immature hIECs and the functional hIECs were allowed to react with 1% formaldehyde (Sigma-Aldrich) at room temperature for 10 minutes. Then, the reaction was stopped by treatment with 1× glycine (Millipore) at room temperature for 5 minutes. The respective cells were washed with cold 1×PBS containing 1× protease inhibitor cocktail II. Thereafter, a chromatin solution was subjected to ultrasonic treatment at 20 cycles, in which Bioruptor® Pico sonication device (B01060010, Diagenode, Belgium) was used and one cycle consisted of turning the device on for 30 seconds and turning the device off for 30 seconds, to obtain chromatin fragments of 200 bp to 1000 bp. The obtained chromatin fragments were treated with 2 μg of anti-H3K4me3 (ab8580; Abcam, Cambridge, MA, USA) antibody, 2 μg of anti-H3K27ac (ab4729; Abcam) antibody, or 2 μg of normal rabbit IgG (2729S; Cell Signaling Technology, Inc., Danvers, MA, USA), and 20 μl of Magna ChIP A/G magnetic beads (Millipore), and reaction was allowed to proceed overnight at 4° C. Washing was performed using a magnetic separation device and a washing buffer, and incubation was performed at 37° C. for 30 minutes with a mixture of ChIP elution buffer and RNase A. Then, incubation was performed with proteinase K at 62° C. for 120 minutes. DNA was purified using a spin column, and then each sample was analyzed using qPCR. qPCR was performed in the same manner as in Experimental Example 1, and the primers used are shown in Table 13 below.

TABLE 13

| Target gene | Primer (Forward) | SEQ ID NO | Primer (Reverse) | SEQ ID NO |
|---|---|---|---|---|
| CDX2 | CTGGAGCTGGAGAAGGAGTTTC | 9 | ATTTTAACCTGCCTCTCAGAGAGC | 10 |
| ANPEP | AAGCCTGTTTCCTCGTTGTC | 13 | AACCTCATCCAGGCAGTGAC | 14 |
| CYP3A4 | CTGTGTGTTTCCAAGAGAAGTTAC | 73 | TGCATCAATTTCCTCCTGCAG | 74 |
| GLUT2 | GGCCAGCAGGTTCATCATCAGCAT | 45 | CCTTGGGCTGAGGAAGAGACTGTG | 46 |
| GLUT5 | CGCCAAGAAAGCCCTACAGA | 47 | GCGCTCAGGTAGATCTGGTC | 48 |

Figure 23:
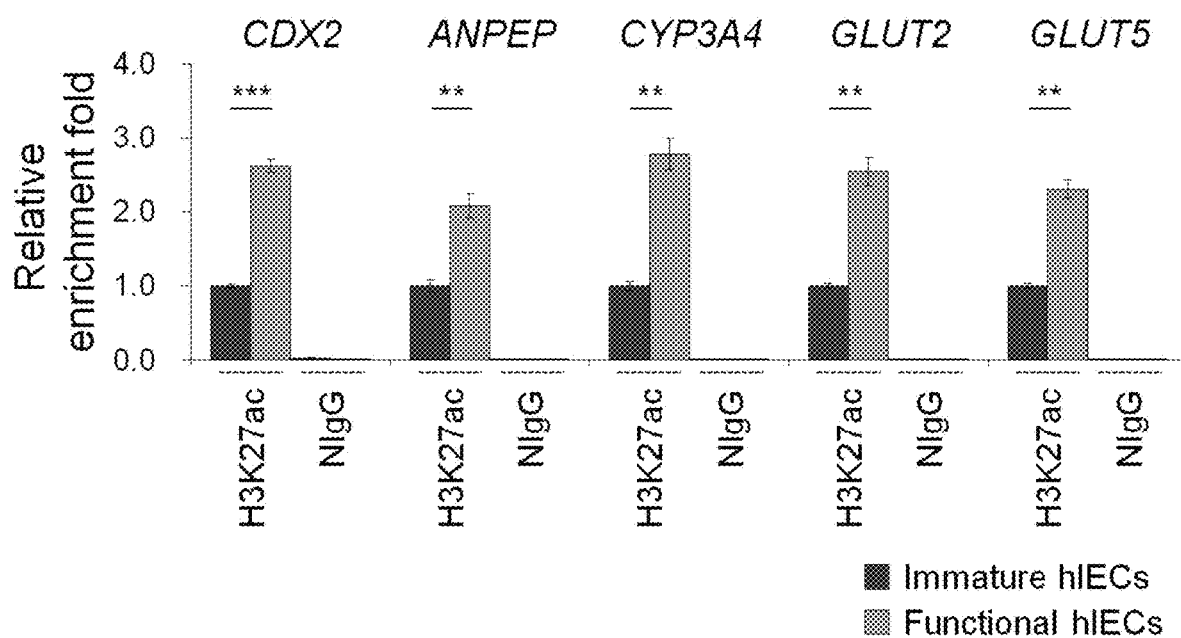
FIG. 23 illustrates a graph, showing enrichment amounts of H3K27ac, which is an active histone mark, in the promoter/enhancer region of CDX2, ANPEP, CYP3A4, GLUT2, and GLUT5 genes in immature hIECs and functional hIECs.
Figure 24:
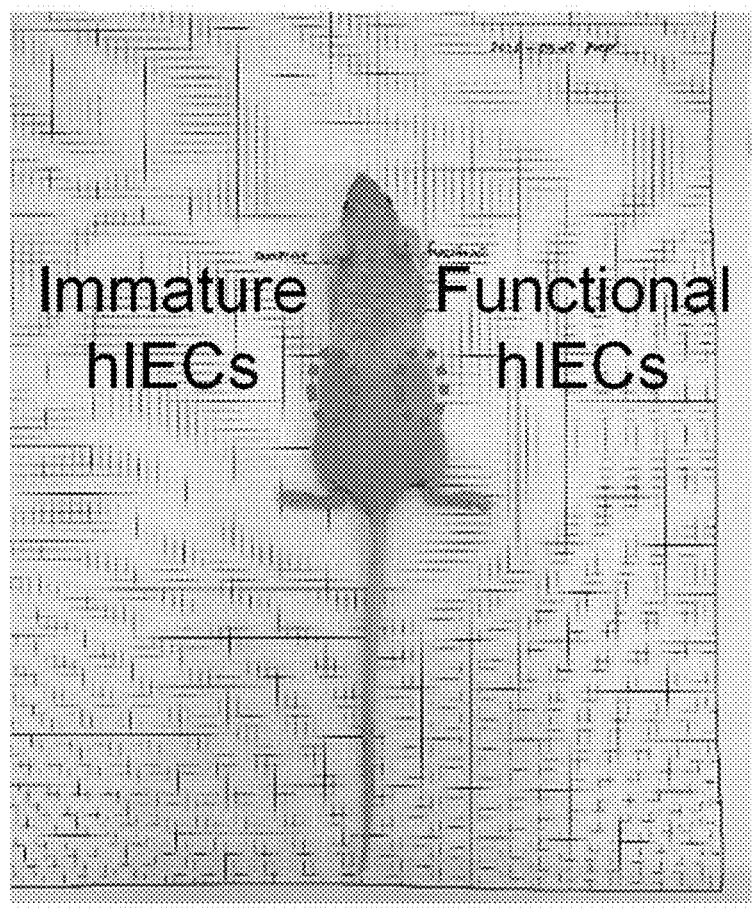
FIG. 24 illustrates a photograph, showing a mouse in which immature hIECs and functional hIECs have been subcutaneously transplanted on the right and left flanks, respectively.
Figure 26:
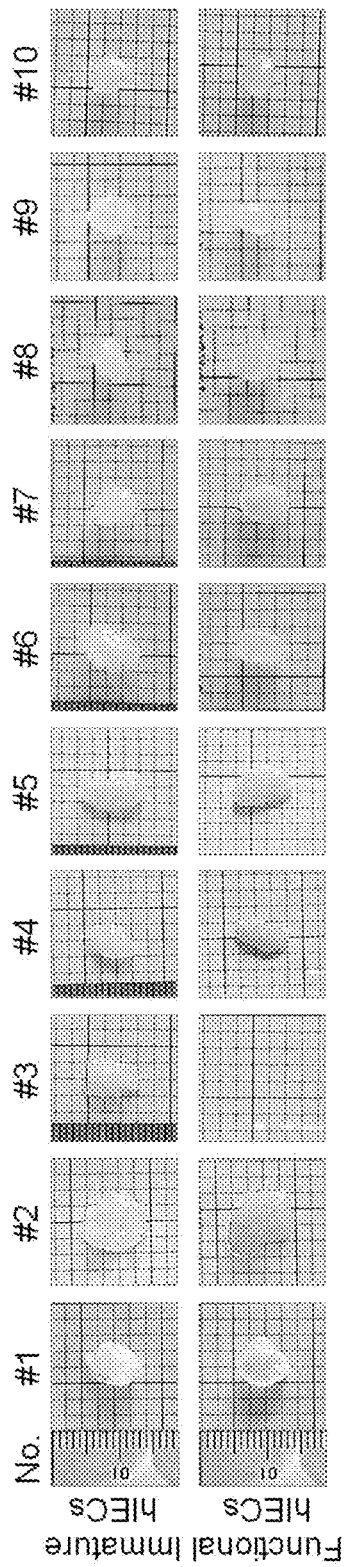
FIG. 26 illustrates photographs of masses that have been generated in a mouse after subcutaneous transplantation of immature hIECs and functional hIECs on the right and left flanks of the mouse, respectively.
Figure 27:
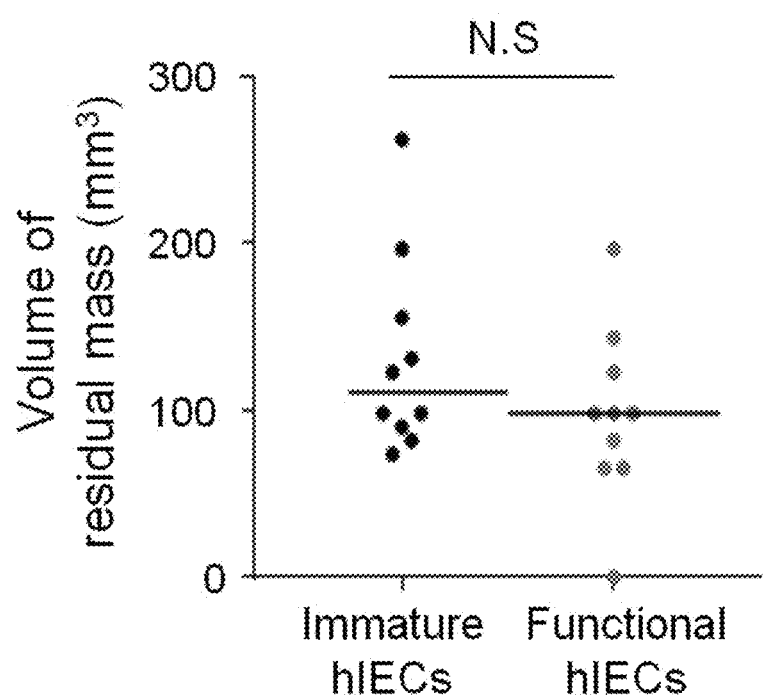
FIG. 27 illustrates a graph, showing volumes of masses that have been generated in a mouse after subcutaneous transplantation of immature hIECs and functional hIECs on the right and left flanks of the mouse, respectively.

As a result, the functional hIECs showed remarkably high enrichment of H3K4me3 and H3K27ac in the promoter and enhancer region of CDX2, ANPEP, CYP3A4, GLUT2, and GLUT5, as compared with the immature hIECs (FIGS. 22 and 23).

Experimental Example 5.2. Identification of Cell Maintenance Capacity In Vivo of Functional hIECs Using Mouse Model To identify whether immature hIECs and functional hIECs maintain cell residual capacity in vivo, the immature hIECs and the functional hIECs, each at $5 \times 10^6$ to $1 \times 10^7$ cells, were transplanted subcutaneously to the right and left flanks, respectively, of nude mice (n=10). For transplantation assay, paraffin sections were deparaffinized and then stained in a manner similar to that used for antigen detection in frozen samples. The transplanted samples were observed using an EVOS microscope (FL Auto 2, Thermo Fisher Scientific, Inc.).

As a result, after 6 to 10 weeks, all mice transplanted with the immature hIECs developed distinct masses, whereas 9 out of 10 mice transplanted with the functional hIECs developed subcutaneous masses having no significant mass difference (FIGS. 24 to 27).

Experimental Example 5.3. Identification of Further Differentiation of Functional hIECs Using Mouse Model After transplantation of the functional hIECs, the presence of residual cells or further cell differentiation was identified using human-specific antibodies and immunohistochemistry. The mice transplanted with only the immature hIECs were prepared in the same manner as in Experimental Example 3.2, and subjected to immunofluorescence staining for human specific nuclear antigen (hNu), intestinal transcription factor (CDX2), intestinal protein (VIL1), and proliferation marker (Ki). The immunofluorescence staining was performed in the same manner as in Experimental Example 4.2, and the primary antibodies used are shown in Table 14 below.

TABLE 14

| Antibodies | Catalog No. | Company | Dilution |
|---|---|---|---|
| anti-hNu | MAB1281 | Millipore | 1:50 |
| anti-CDX2 | ab15258 | abcam | 1:100 |

TABLE 14-continued

| Antibodies | Catalog No. | Company | Dilution |
|---|---|---|---|
| anti-Villin1 | sc-7672 | Santa Cruz | 1:50 |
| anti-ki67 | MAB9260 | Millipore | 1:100 |

As a result, it was identified that in 2 out of 10 mice, hIEC-derived endoderm cells were included in the immature hIEC-Matrigel plug, and the human specific nuclear antigen (hNu), the intestinal transcription factor (CDX2), the intestinal protein (VIL1), and the proliferation marker (Ki67) were expressed. On the other hand, it was identified that in the mice transplanted with the functional hIECs, human cells were not included in the functional hIEC-Matrigel plug even after long-term in vivo culture, and the functional hIECs were finally differentiated into mature intestinal epithelium (FIG. 28).

II. Preparation of Functional hIECs Using Induced Pluripotent Stem Cells (iPSCs)

Figure 29:
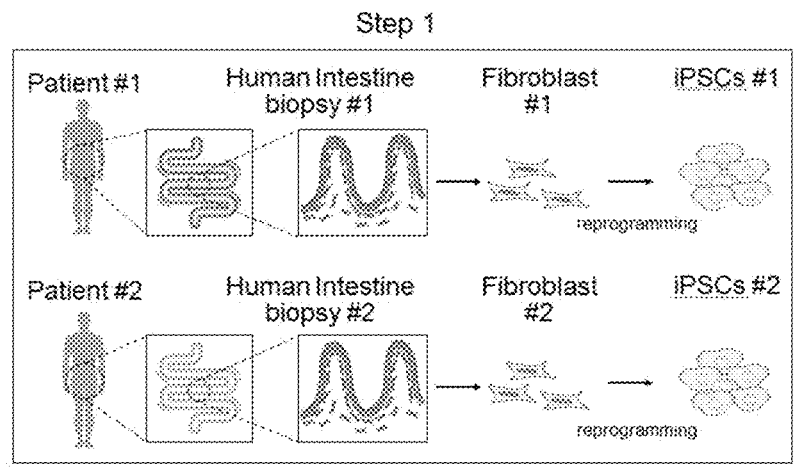
FIG. 29 illustrates schematic diagrams, showing processes of differentiation of induced pluripotent stem cells (iPSCs) and a 3D expanded intestinal spheroid ($InS^{exp}$) into human intestinal epithelial cells (hIECs).
Figure 29:
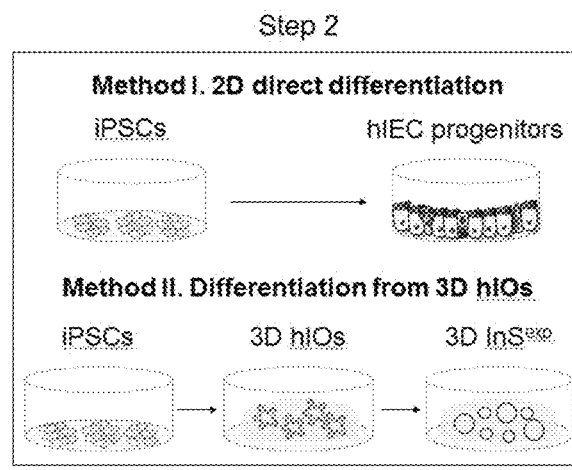
Figure 29:
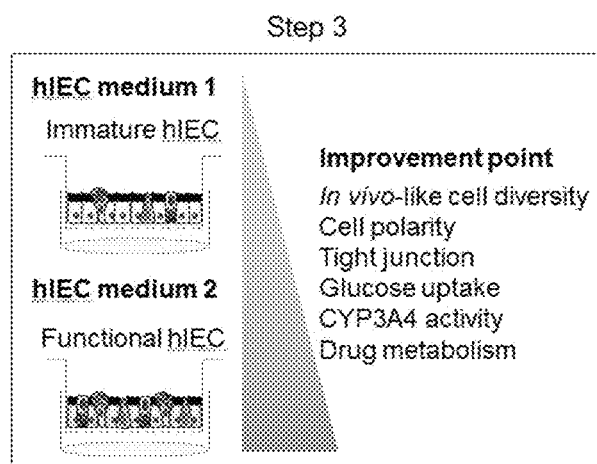

To prepare a human intestinal epithelial cell (hIEC) model differentiated from induced pluripotent stem cells (iPSCs), a new differentiation method that mimics development of the small intestine in vivo was established. The human intestinal epithelial cell model prepared by the above-mentioned method is referred to as functional human intestinal epithelial cells (functional hIECs). A schematic diagram of a method for differentiating iPSCs into hIECs is illustrated in FIG. 29.

Example 3. Preparation of iPSCs

Human small intestine (hSI) tissue was collected from 2 adults in a routine endoscopy approved by the Institutional Review Board of Chungnam National University Hospital (IRB File No. CNUH 2016-03-018), in which prior informed consent was obtained from both patients. Each tissue sample was digested with collagenase type I (Thermo Fisher Scientific Inc.) for 3 hours in a shaking incubator at 37° C., and pipetted up and down. Then, centrifugation was performed. After centrifugation, the pellet was washed and dispensed into a plate coated with 0.2% gelatin. Then, culture was performed in minimal essential medium (MEM, Thermo Fisher Scientific Inc.) containing 10% FBS (Thermo Fisher Scientific Inc.), 1% penicillin and streptomycin (P/S, Thermo Fisher Scientific Inc.), and 1 mM non-essential amino acids (NEAA, Thermo Fisher Scientific Inc.). Isolated fibroblasts were made into iPSCs to have induced pluripotency, using a CytoTune-iPS 2.0 Sendai reprogramming kit. H9 hESC line (WiCell Research Institute, Madison, Wis., USA) and the iPSCs were cultured in the same manner as in Example 1. Caco-2 cell line (ATCC, Manassas, Virginia, USA) was cultured according to a standard culture protocol using minimal essential medium containing 10% FBS, 1% penicillin and streptomycin, and 1 mM non-essential amino acids. For the monolayer experiment, the Caco-2 cell line was dispensed, at a density of $1.34 \times 10^5$ cells/cm$^2$, into a Transwell insert coated with 5% Matrigel (Corning, NY, USA). Here, replacement of the medium was performed every other day.

Figure 30:
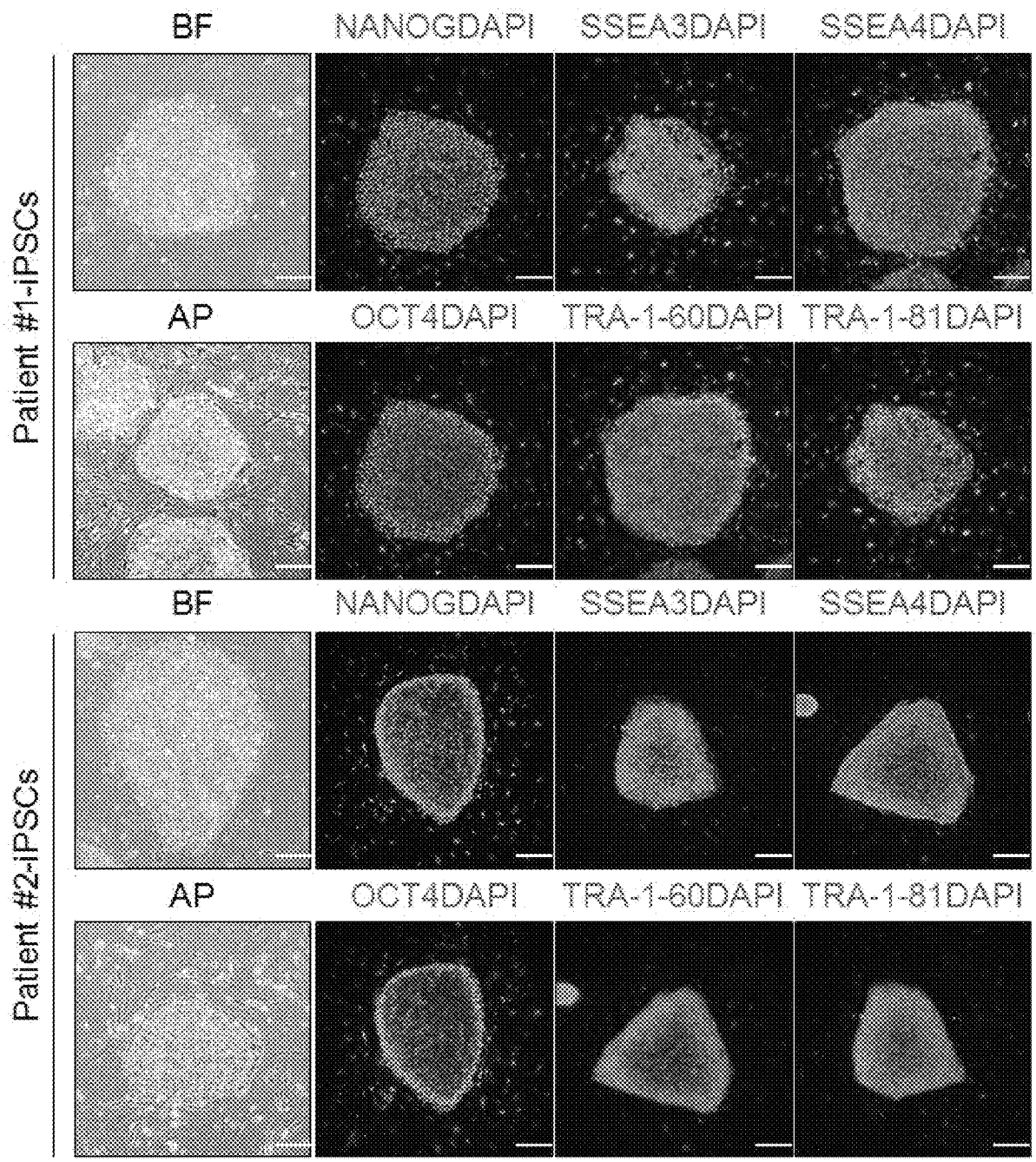
FIG. 30 illustrates photographs taken after subjecting fibroblast-derived iPSCs to immunofluorescence staining, to identify representative morphologies thereof and expression levels therein of OCT4, NANOG, TRA-1-60, TRA-1-81, SSEA-3 and SSEA-4 genes, which are pluripotency markers.
Figure 31:
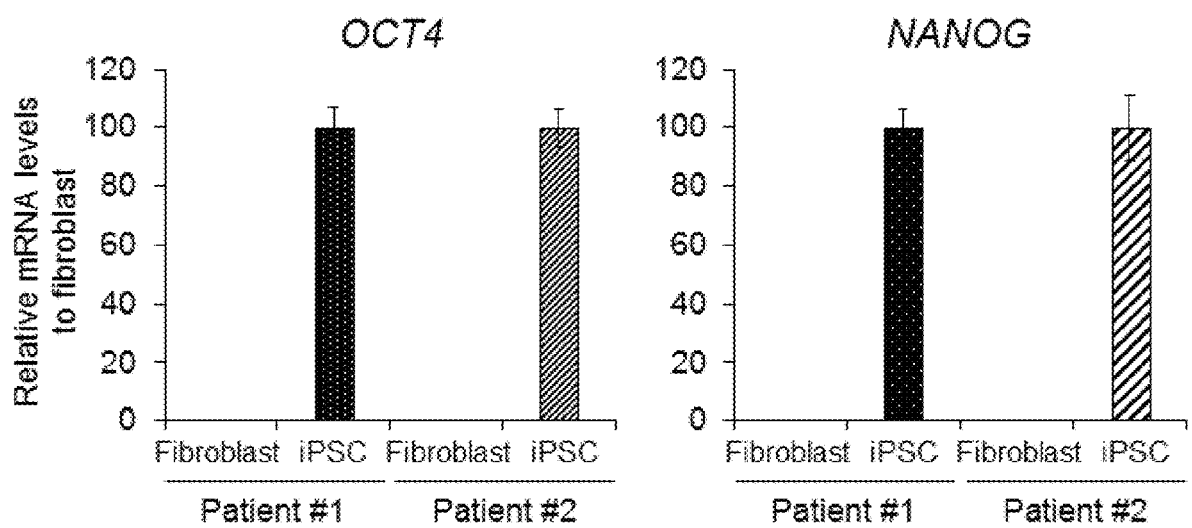
FIG. 31 illustrates graphs, showing expression levels of OCT4 and NANOG, which are pluripotency markers, in fibroblast-derived iPSCs.

In the iPSCs (KRIBB-hiPSC #1, #2) prepared in Example 3, the expression levels of NANOG, SSEA3, SSEA4, OCT4, TRA-1-60, and TRA-1-81, which are iPSC-related markers, were checked through immunofluorescence staining (FIGS. 30 and 31). The immunofluorescence staining was performed in the same manner as in Experimental Example 4.2, and the primary antibodies used are shown in Table 15 below.

TABLE 15

| Antibodies | Catalog No. | Company | Dilution |
|---|---|---|---|
| anti-NANOG | AF1997 | R&D | 1:40 |
| anti-SSEA-3 | MAB4303 | Millipore | 1:500 |
| anti-SSEA-4 | MAB4304 | Millipore | 1:500 |
| anti-OCT4 | sc-9081 | Santa Cruz Biotechnology | 1:500 |
| anti-TRA-1-60 | MAB4360 | Millipore | 1:500 |
| anti-TRA-1-81 | MAB4381 | Millipore | 1:500 |

Figure 32:
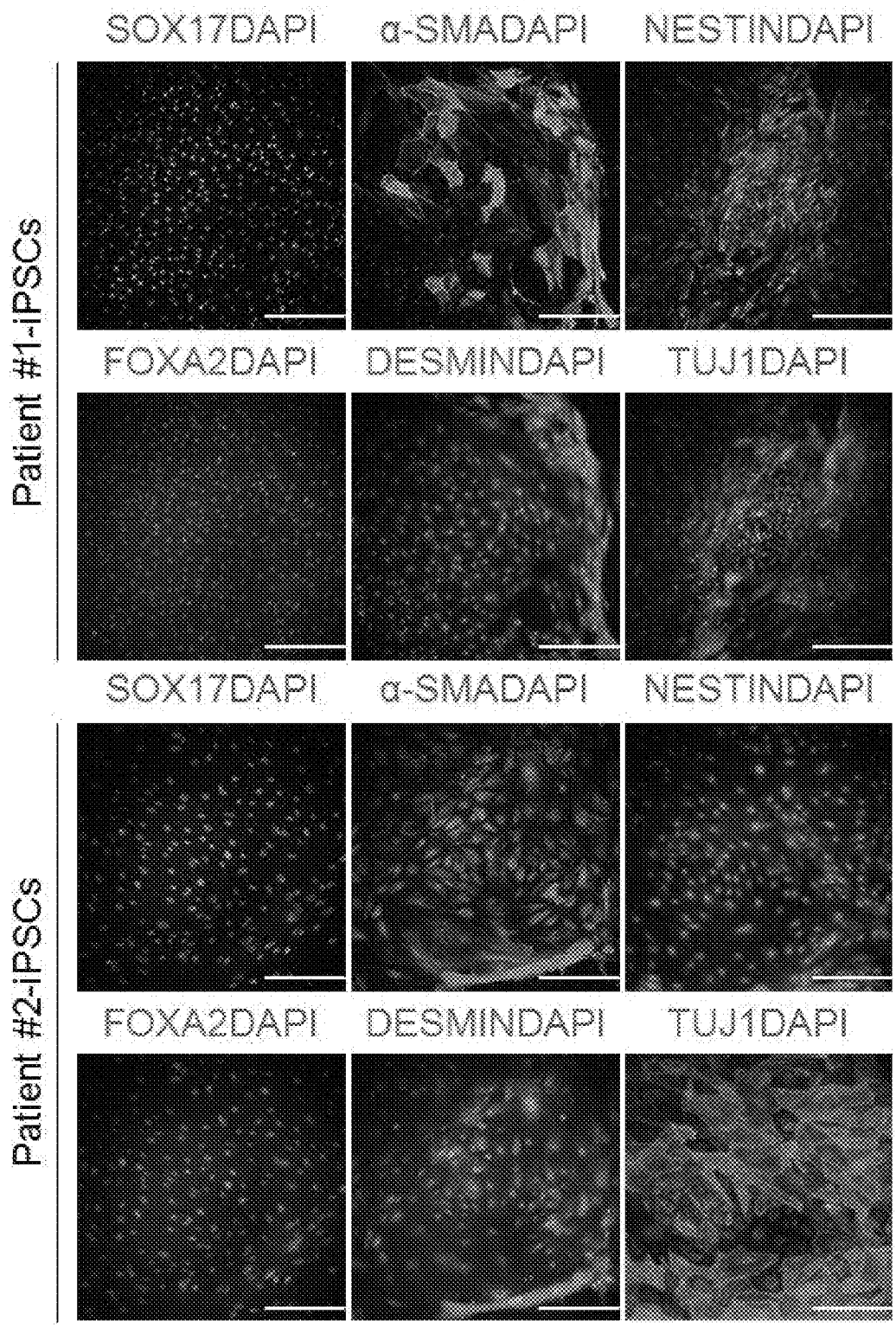
FIG. 32 illustrates photographs taken after subjecting fibroblast-derived iPSCs to immunofluorescence staining, to identify expression levels therein of FOXA2 and SOX17, which are endoderm markers, DESMIN and α-SMA, which are mesoderm markers, and TUJ1 and NESTIN, which are ectoderm markers.

In addition, in the iPSCs prepared in Example 3, the expression levels of SOX17, alpha-SMA, NESTIN, FOXA2, DESMIN, and TUJ1, which are iPSC-related markers, were checked through immunofluorescence staining (FIG. 32). The immunofluorescence staining was performed in the same manner as in Experimental Example 4.2, and the primary antibodies used are shown in Table 16 below.

TABLE 16

| Antibodies | Catalog No. | Company | Dilution |
|---|---|---|---|
| anti-SOX17 | MAB1924 | R&D | 1:50 |
| anti-α-SMA | A5228 | Sigma | 1:200 |
| anti-NESTIN | MAB5326 | Millipore | 1:100 |
| anti-FOXA2 | 07-633 | Millipore | 1:100 |
| anti-DESMIN | AB907 | Chemicon | 1:50 |
| anti-TUJ1 | PRB-435P | Covance | 1:500 |

A short tandem repeat (STR) assay was performed to identify that the iPSCs were derived from human tissue. For this experiment, genomic DNA was extracted from the fibroblasts of each patient, which are parental cells, and the iPSCs derived therefrom, and a request was made to HPBio for analysis thereof. Whether or not they came from the same person could be identified by analyzing the number of repetitions of the STR site in the DNA sequence. As a result, it was identified that the iPSCs were derived from the fibroblasts of each patient (FIG. 33).

Figure 34:
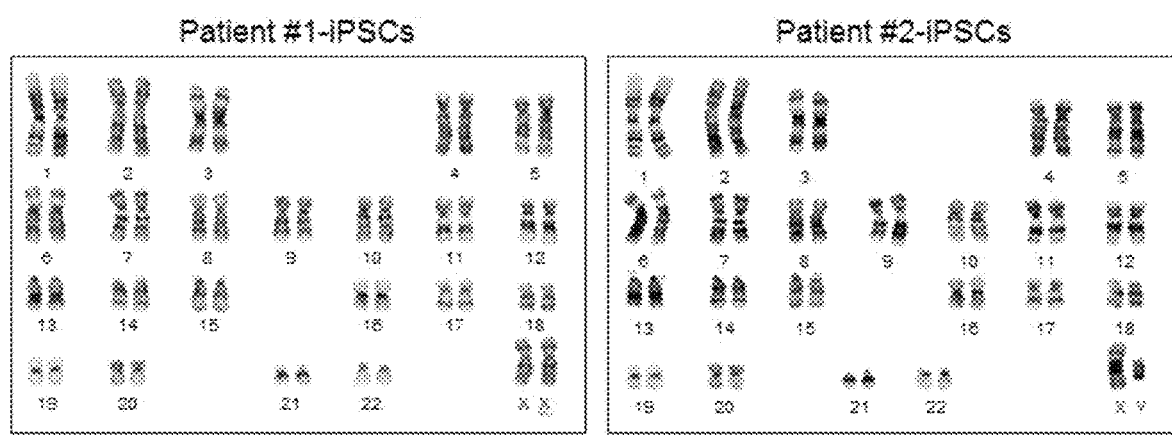
FIG. 34 illustrates results obtained by analyzing karyotypes of fibroblast-derived iPSCs.

For karyotyping to identify whether the iPSCs maintain a normal karyotype, naturally differentiated iPSCs were prepared and a request was made to GenDix for analysis thereof. It was intended to determine the presence or absence of chromosomal abnormalities by performing staining of chromosomes with Giemsa (G)-banding. As a result, it was identified that the iPSCs (KRIBB-hiPSC #1, #2) prepared in Example 3 showed a normal karyotype (FIG. 34).

Example 4. Differentiation of iPSCs into Immature hIECs and Functional hIECs

The iPSCs prepared in Example 3 were differentiated into hIEC progenitors in the same manner as in Example 1. Then, the differentiated hIEC progenitors were differentiated into immature hIECs and functional human intestinal epithelial cells in the same manner as in Example 2 and Comparative Example 1.

Figure 35:
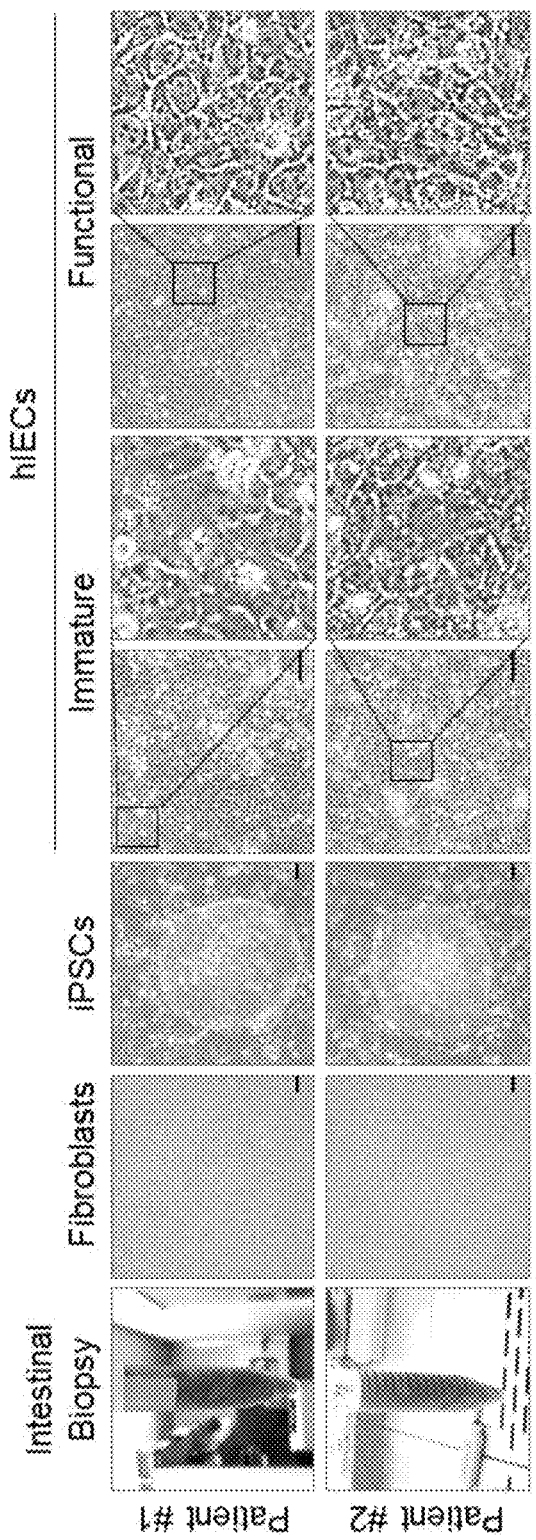
FIG. 35 illustrates diagrams, identifying morphological differences between iPSC-derived immature hIECs and iPSC-derived functional hIECs.

The morphological differences between the iPSC-derived immature hIECs and functional hIECs, which were differentiated in Example 4, were identified through a microscope. As a result, it was identified that the functional hIECs had a higher cell density than the immature hIECs, and the functional hIECs had a similar shape to the polygonal epithelium (FIG. 35).

Experimental Example 7. Identification of Characteristics of iPSC-Derived Functional hIECs as Human Intestinal Epithelial Model Experimental Example 7.1. Identification I of Expression of Marker Genes Related to Intestinal and Secretory Cells in iPS C-Derived Functional hIECs The expression levels of marker genes related to intestinal and secretory cells in hSI, iPSCs, iPSC-derived immature hIECs, iPSC-derived functional hIECs, and Caco-2 cell line were checked through qPCR analysis. qPCR was performed in the same manner as in Experimental Example 1, and the primers used are shown in Table 17 below.

TABLE 17

| Target gene | Primer (Forward) | SEQ ID NO | Primer (Reverse) | SEQ ID NO |
|---|---|---|---|---|
| LGR5 | TGCTCTTCACCAACTGCATC | 1 | CTCAGGCTCACCAGATCCTC | 2 |
| ASCL2 | CGTGAAGCTGGTGAACTTGG | 3 | GGATGTACTCCACGGCTGAG | 4 |
| CD166 | TCAAGGTGTTCAAGCAACCA | 5 | CTGAAATGCAGTCACCCAAC | 6 |
| LRIG1 | GACCCTTTCTGACCGACAA | 7 | CGCTTTCCACGGCTCTTT | 8 |
| CDX2 | CTGGAGCTGGAGAAGGAGTTTC | 9 | ATTTTAACCTGCCTCTCAGAGAGC | 10 |
| VIL1 | AGCCAGATCACTGCTGAGGT | 11 | TGGACAGGTGTTCCTCCTTC | 12 |
| ANPEP | AAGCCTGTTTCCTCGTTGTC | 13 | AACCTCATCCAGGCAGTGAC | 14 |
| SI | GGTAAGGAGAAACCGGGAAG | 15 | GCACGTCGACCTATGGAAAT | 16 |
| LYZ | AAAACCCCAGGAGCAGTTAAT | 17 | CAACCCTCTTTGCACAAGCT | 18 |
| MUC2 | TGTAGGCATCGCTCTTCTCA | 19 | GACACCATCTACCTCACCCG | 20 |
| CHGA | TGACCTCAACGATGCATTTC | 21 | CTGTCCTGGCTCTTCTGCTC | 22 |
| MDR1 | GCCAAAGCCAAAATATCAGC | 41 | TTCCAATGTGTTCGGCATTA | 42 |
| SGLT1 | GTGCAGTCAGCACAAAGTGG | 43 | ATGCACATCCGGAATGGGTT | 44 |
| GLUT2 | GGCCAGCAGGTTCATCATCAGCAT | 45 | CCTTGGGCTGAGGAAGAGACTGTG | 46 |
| GLUT5 | CGCCAAGAAAGCCCTACAGA | 47 | GCGCTCAGGTAGATCTGGTC | 48 |
| CYP3A4 | CTGTGTGTTTCCAAGAGAAGTTAC | 73 | TGCATCAATTTCCTCCTGCAG | 74 |
| MUC13 | CGGATGACTGCCTCAATGGT | 83 | AAAGACGCTCCCTTCTGCTC | 84 |
| ZO-1 | CCCGACCATTTGAACGCAAG | 23 | ATGCCCATGAACTCAGCACG | 24 |
| OCLN | CATTGCCATCTTTGCCTGTG | 25 | AGCCATAACCATAGCCATAGC | 26 |
| CLDN1 | CCCAGTCAATGCCAGGTACG | 27 | GGGCCTTGGTGTTGGGTAAG | 28 |
| CLDN3 | CAGGCTACGACCGCAAGGAC | 29 | GGTGGTGGTGGTGGTGTTGG | 30 |
| CLDN5 | GGCTGCTTTGCTGCAACTGTC | 31 | GAGCCGTGGCACCTTACACG | 32 |
| CLDN4 | GCAGCCCCTGTGAAGATTGA | 85 | GTCTCTGGCAAAAGCGGTG | 86 |
| CLDN7 | CCATGACTGGAGGCATCATTT | 87 | GACAATCTGGTGGCCATACCA | 88 |
| CLDN15 | CATCACCACCAACACCATCTT | 89 | GCTGCTGTCGCCTTCTTGGTC | 90 |

Figure 36A:
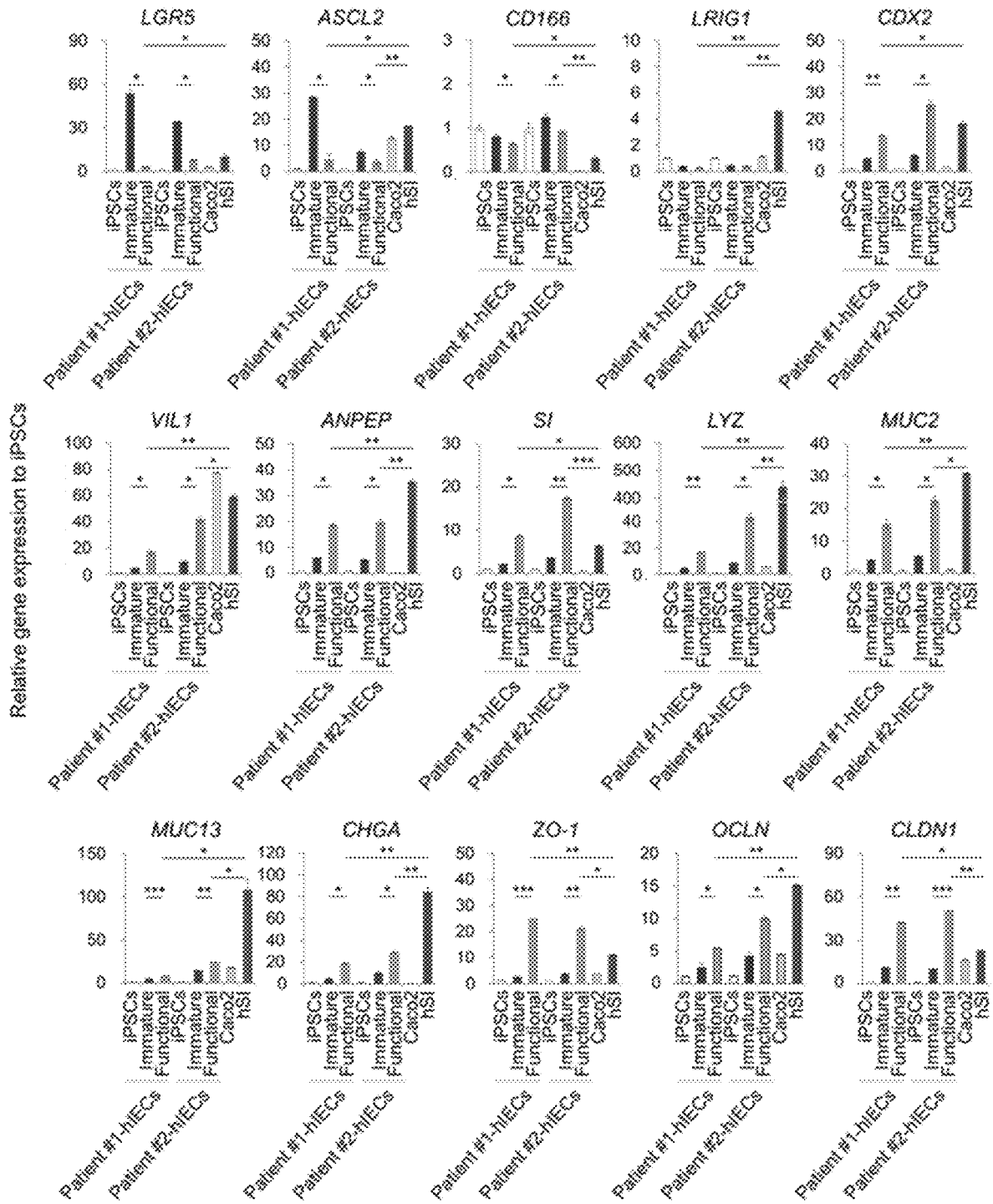
FIG. 36A illustrates graphs, showing expression levels of LGR5, ASCL2, CD166, LRIG1, CDX2, VIL1, ANPEP, SI, LYZ, MUC2, MUC13, CHGA, ZO-1, OCLN, and CLDN1 genes in iPSC-derived immature hIECs and iPSC-derived functional hIECs.
Figure 36B:
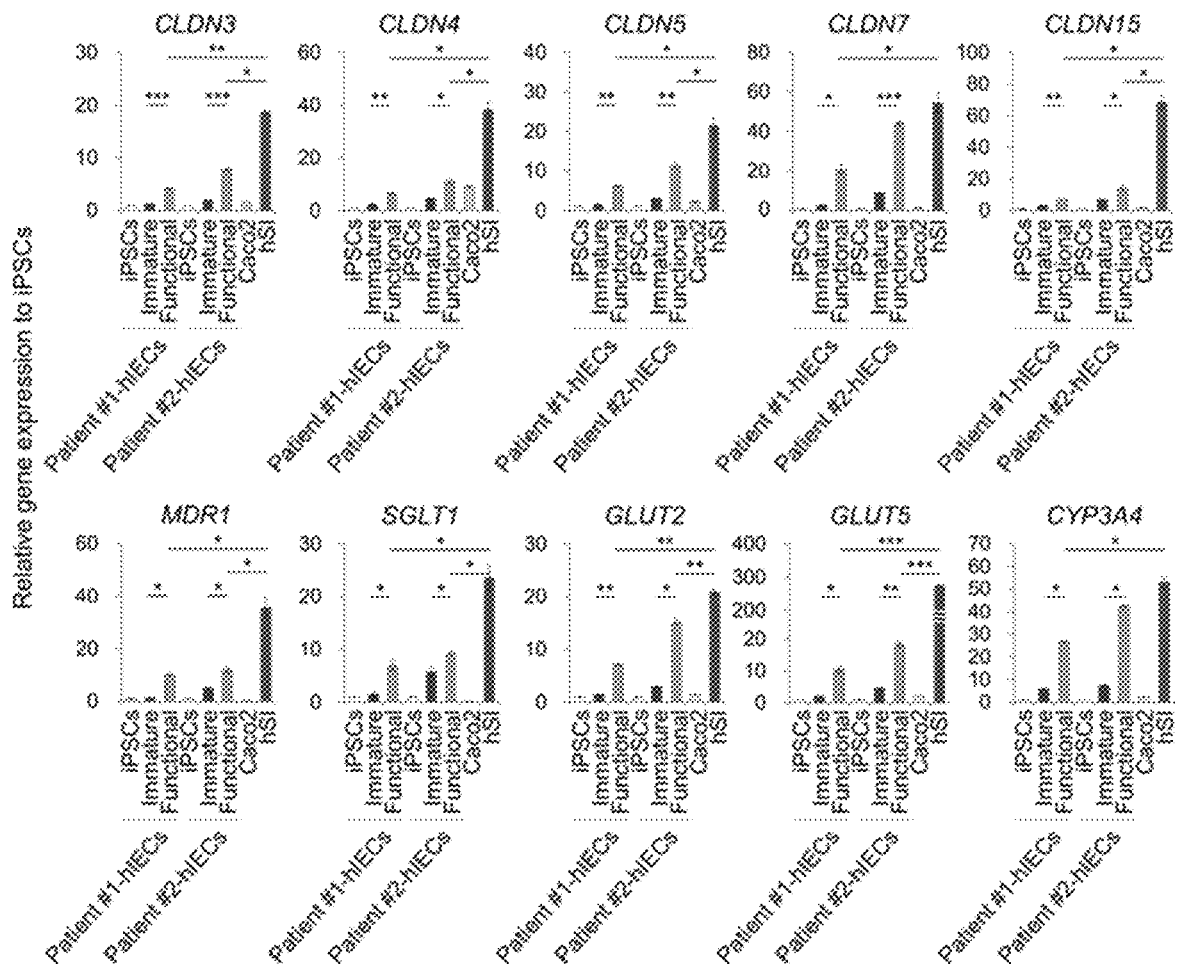
FIG. 36B illustrates graphs, showing expression levels of CLDN3, CLDN4, CLDN5, CLDN7, CLDN15, MDR1, SGLT1, GLUT2, GLUTS, and CYP3A4 genes in iPSC-derived immature hIECs and iPSC-derived functional hIECs.

As a result, the expression of LGR5, ASCL2, and CD166 genes increased in the immature hIECs, whereas the expression thereof decreased in the functional hIECs. In addition, it was identified that as compared with the immature hIECs, the functional hIECs showed significantly increased expression levels of major intestinal cell-specific markers such as CDX2, VIL1, ANPEP, SI, LYZ, MUC2, MUC13, CHGA, ZO-1, OCLN, CLDN1, CLDN3, CLDN4, CLDN5, CLDN7, CLDN15, MDR1, SGLT1, GLUT2, GLUT5, and CYP3A4 (FIGS. 36A and 36B).

Experimental Example 7.2. Identification II of Expression of Marker Genes Related to Intestinal and Secretory Cells in iPS C-Derived Functional hIECs The expression levels of CDX2 and VILLIN (VIL1), LYZ, MUC2, and CHGA in the iPSC-derived immature hIECs and the iPSC-derived functional hIECs were checked through immunofluorescence staining in the same manner as in Experimental Example 4.2.

Figure 37:
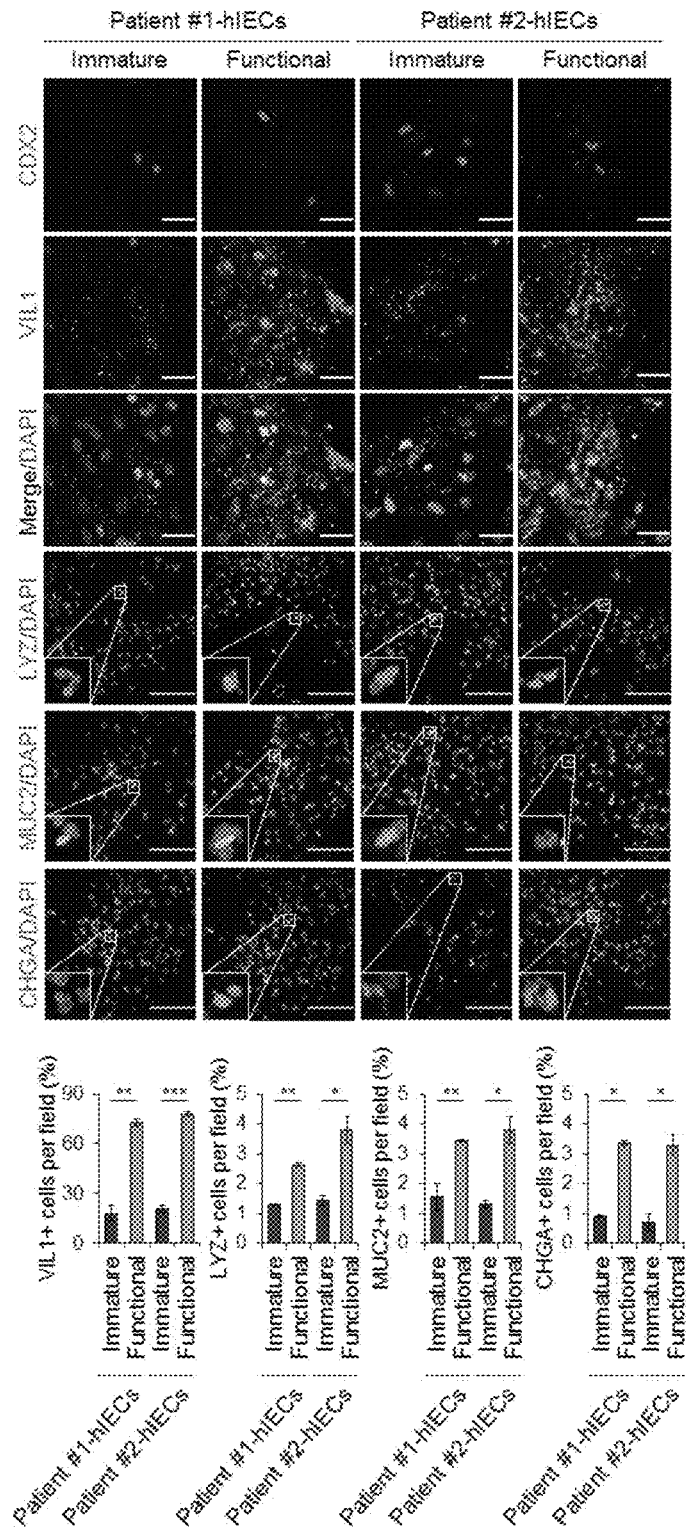
FIG. 37 illustrates results obtained by identifying, through immunofluorescence staining, expression levels of VIL1, LYZ, MUC2, and CHGA in iPSC-derived immature hIECs and iPSC-derived functional hIECs.

As a result, it was identified that the functional hIECs showed an increased expression level of VIL1 as compared with the immature hIECs. In addition, it was identified that the functional hIECs showed significantly increased expression levels of CHGA, MUC2, and LYZ as compared with the immature hIECs (FIG. 37).

Experimental Example 7.3. Identification of Expression of Marker Genes Related to Apical Side and Basolateral Side of Cell Membrane in iPS C-Derived Functional hIECs For the iPSC-derived immature hIECs and functional hIECs obtained in Example 4, the expression levels of VIL1, which is a marker gene related to the apical side of the cell membrane, and $Na^+$—$K^+$ ATPase, which is a marker gene related to the basolateral side of the cell membrane, were checked through immunofluorescence staining in the same manner as in Experimental Example 4.5.

Figure 38:
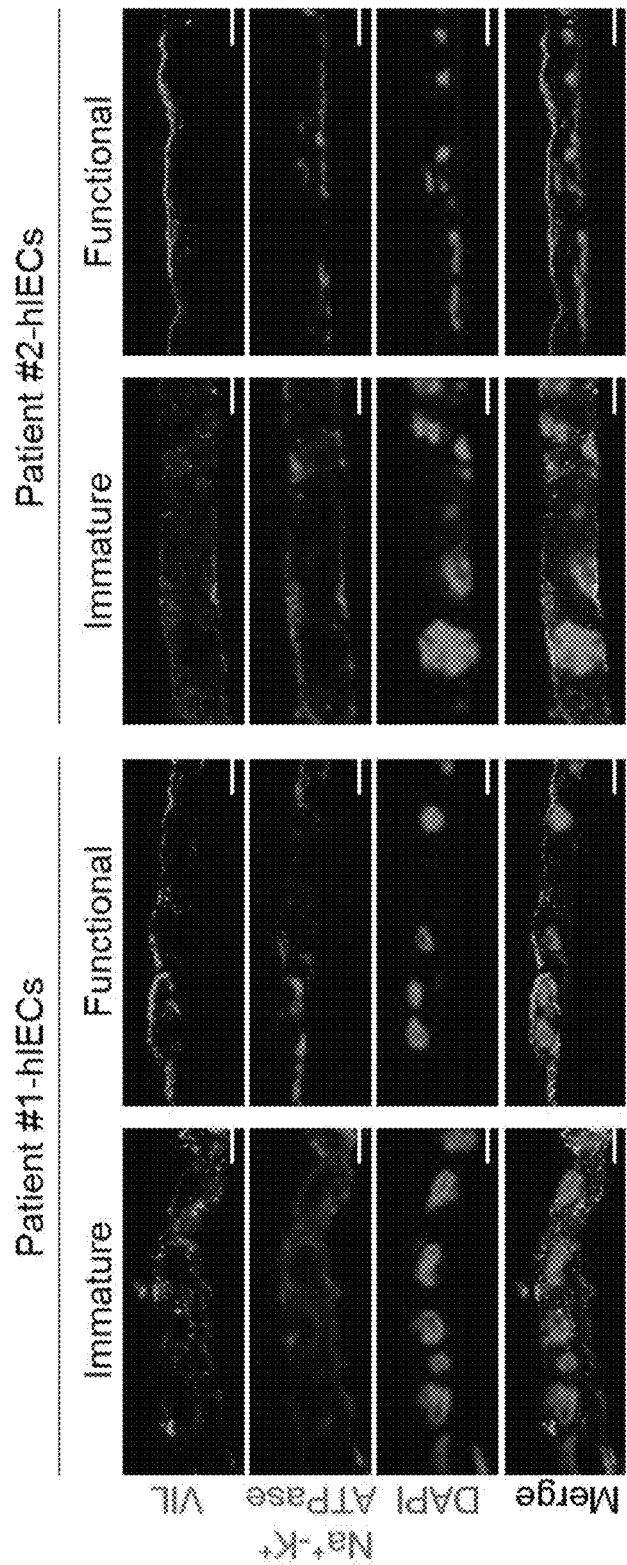
FIG. 38 illustrates results obtained by identifying, through immunofluorescence staining, expression levels of VIL1, which is a marker gene related to the apical side of the cell membrane, and Na$^+$—K$^+$ ATPase, which is a marker gene related to the basolateral side of the cell membrane, in iPSC-derived immature hIECs and iPSC-derived functional hIECs.

As a result, it was identified that as compared with the immature hIECs, the functional hIECs formed a structurally polarized monolayer in polarization distribution of the apical (VIL1) and basolateral ($Na^+$—$K^+$ ATPase) cell surface proteins (FIG. 38). From these results, it was identified that the functional hIECs had an improved barrier function as compared with the immature hIECs.

Experimental Example 7.4. Identification of Barrier Function of iPSC-Derived Functional hIECs For the iPSC-derived immature hIECs and functional hIECs in Example 4, their barrier function was identified by continuously measuring the transepithelial electrical resistance (TEER) values during the culture period. Here, the measurement of TEER was performed using an epithelial tissue volt-ohm-meter (EVOM2, WPI, Sarasota, FL, USA) according to the manufacturer's manual.

Figure 39:
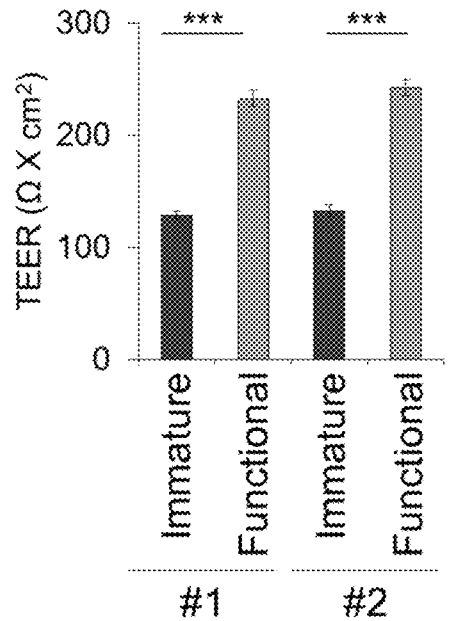
FIG. 39 illustrates a graph, showing transepithelial electric resistance (TEER) values of iPSC-derived immature hIECs and iPSC-derived functional hIECs.

As a result, the TEER value of the immature hIECs was measured as $128.52 \pm 4.07$ $S^{2}*cm^{2}$ and $132.16 \pm 5.3152 * cm^{2}$, and the TEER value of the functional hIECs was measured as $232.68 \pm 7.11$ $S^{2}*cm^{2}$ and $242.48 \pm 7.12$ $52*cm^{2}$. From these results, it was identified that the TEER value of the functional hIECs was higher than that of the immature hIECs (FIG. 39).

Experimental Example 7.5. Identification of Expression and Activity of CYP3A4 in iPS C-Derived Functional hIECs For the iPSC-derived immature hIECs and functional hIECs in Example 4, CYP3A4 gene expression and CYP3A4 enzyme activity therein were analyzed in the same manner as in Experimental Example 4.8. Here, the CYP3A4 gene expression and the CYP3A4 enzyme activity were analyzed in the same manner as in Experimental Example 4.8.

Figure 40:
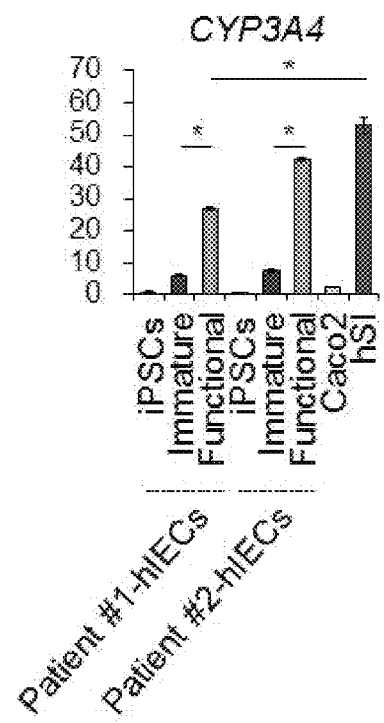
FIG. 40 illustrates a graph, showing expression levels of CYP3A4 gene in iPSC-derived immature hIECs and iPSC-derived functional hIECs.
Figure 41:
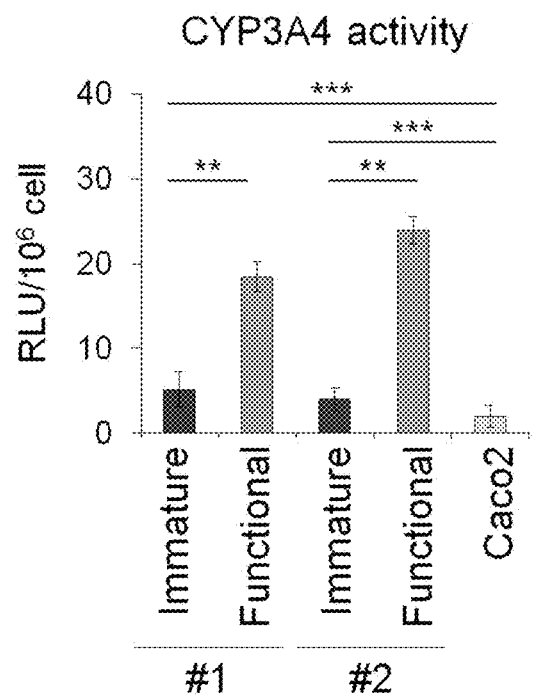
FIG. 41 illustrates a graph, showing activity of CYP3A4 enzyme in iPSC-derived immature hIECs and iPSC-derived functional hIECs.

As a result, it was identified that the functional hIECs showed an increased expression level of CYP3A4 as compared with the immature hIECs (FIG. 40). In addition, it was identified that the functional hIECs showed remarkably increased CYP3A4 enzyme activity as compared with the immature hIECs (FIG. 41).

III. Preparation of Functional hIECs Using 3D-Expanded Intestinal Spheroid ($InS^{exp}$)

To prepare a human intestinal epithelial cell (hIEC) model differentiated from a 3D-expanded intestinal spheroid ($InS^{exp}$)), a new differentiation method that mimics development of the small intestine in vivo was established. The human intestinal epithelial cell model prepared by the above-mentioned method is referred to as functional human intestinal epithelial cells (functional hIECs). A schematic diagram of a method for differentiating $InS^{exp}$ into hIECs is illustrated in FIG. 29.

Example 5. Differentiation of $InS^{exp}$ into Immature hIECs and Functional hIECs A 3D human intestinal organoid (hIO) is widely used as an in vivo model system of human small intestinal epithelium. However, since the 3D human intestinal organoid has an apical surface that faces the 3D structure's interior, it is not suitable for existing analysis systems. Therefore, studies are attempted to convert the 3D human intestinal organoid into a 2D human intestinal epithelial cell monolayer. To start culture, a human intestinal organoid was prepared using the iPSCs prepared in Example 3, and the iPSC-derived human intestinal organoid thus prepared was separated into single cells or single crypts. Then, the resultant was embedded in a Matrigel dome to prepare a 3D-expanded intestinal spheroid ($InS^{exp}$). A hPSC-derived human intestinal organoid was prepared with reference to Jung et al.

The human intestinal organoid was incubated in trypsin-EDTA for 5 minutes, and then physically dissociated by performing pipetting 10 times. The dissociated human intestinal organoid was placed in 10 ml of medium and resuspended by performing centrifugation with 1,500 rpm for 5 minutes at 4° C. The supernatant was removed and the pellet was resuspended in Matrigel. The human intestinal organoid-Matrigel mixture was re-dispensed into a 4-well-plate and incubated at 37° C. for 10 minutes in a $CO_2$ incubator. Then, the Matrigel was solidified, and an $InS^{exp}$ culture medium was added thereto. The medium was replaced with a medium for isolated intestinal crypts. Here, the medium for intestinal crypts contained DMEM/F12, 2 mM L-glutamine, 15 mM HEPES buffer, 2% B27 supplement, 10 nM [Leu-15]-gastrin I (Sigma-Aldrich, St. Louis, MO, USA), 100 ng/ml of human recombinant WNT3A (R&D Systems), 100 ng/ml of EGF, 100 ng/ml of Noggin (R&D Systems), 100 ng/ml of R-spondin 1, 500 nM A-83-01 (Tocris), 500 µM SB202190 (Sigma-Aldrich), 10 nM prostaglandin E2 (Sigma-Aldrich), 1 mM N-acetylcysteine (Sigma-Aldrich), 10 mM nicotinamide (Sigma-Aldrich), 10 µL of Y-27632 (Tocris), and 1 µM Jagged-1 (AnaSpec, Fremont, CA, USA).

For the first 2 days, the culture was performed by treatment with the medium for intestinal crypts. The medium was replaced with an $InS^{exp}$ culture medium every 3 days.

Figure 42:
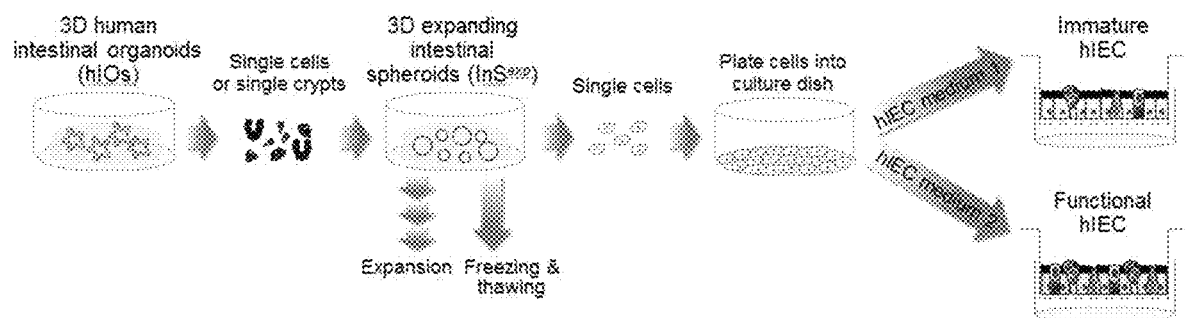
FIG. 42 illustrates a schematic diagram, showing a process of differentiation of a 3D expanded intestinal spheroid (InS$^{exp}$) into human intestinal epithelial cells.

To differentiate the prepared 3D-expanded intestinal spheroid ($InS^{exp}$) into immature hIECs and functional hIECs, the 3D-expanded intestinal spheroid was removed by treatment with trypsin-EDTA, and re-dispensed into a plate coated with 1% Matrigel or a Transwell insert using an $InS^{exp}$ culture medium, supplemented with 10 µl of Y-27632 and 1 µM Jagged-1. Replacement of the $InS^{exp}$ culture medium was performed every 2 days until the cells were almost fully grown. Then, the medium was replaced with hIEC differentiation medium 1 or hIEC differentiation medium 2. Here, replacement of the medium was performed every other day (FIG. 42).

Figure 43:
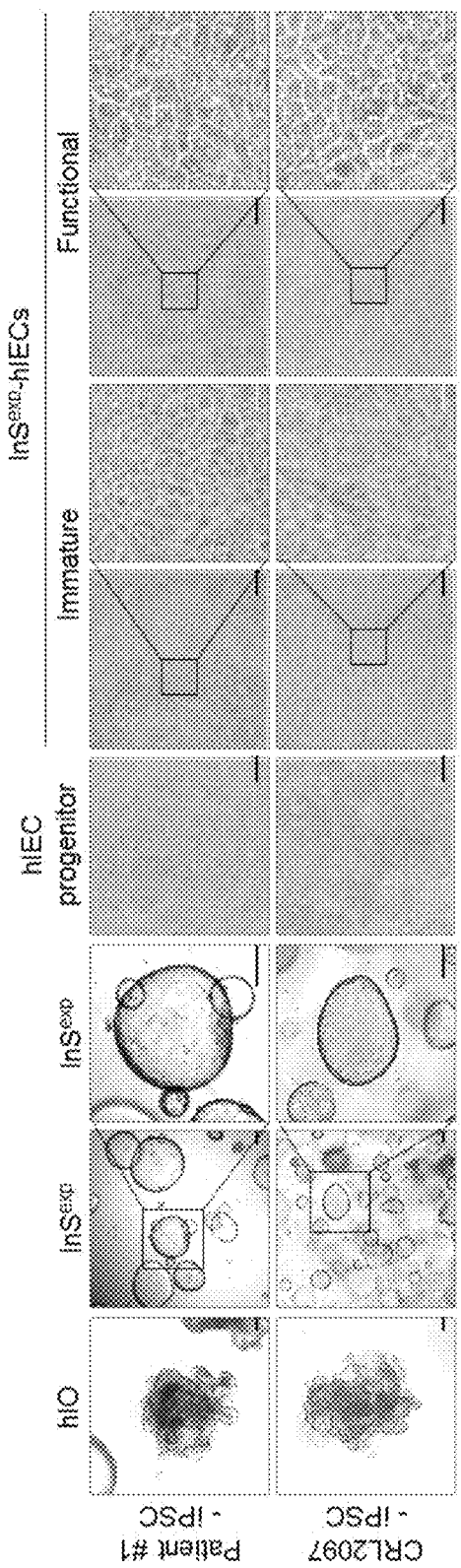
FIG. 43 illustrates diagrams, identifying morphological differences between human intestinal organoid (hIO), InS$^{exp}$, InS$^{exp}$-derived immature hIECs, and InS$^{exp}$-derived functional hIECs.

The morphological differences between the hIO, the $InS^{exp}$, the $InS^{exp}$-derived immature hIECs, and the $InS^{exp}$-derived functional hIECs were identified through a microscope. As a result, it was identified that the functional hIECs had a higher cell density than the immature hIECs, and the functional hIECs had a similar shape to the polygonal epithelium, rather than the immature hIECs (FIG. 43).

Figure 44:
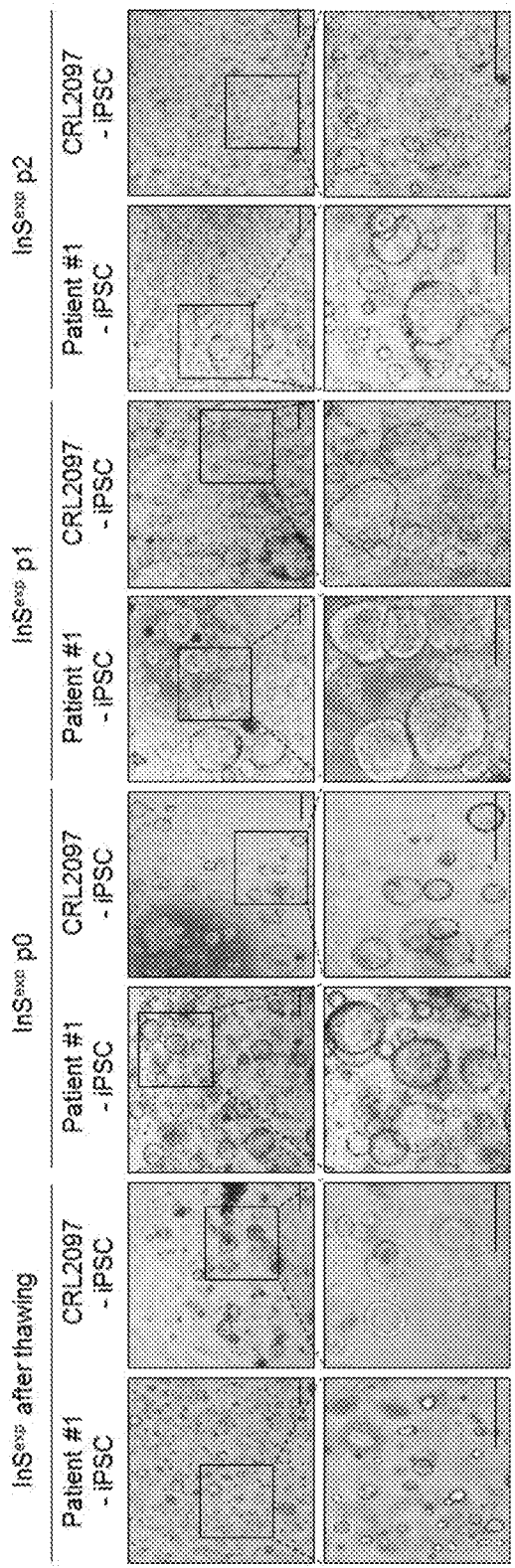
FIG. 44 illustrates diagrams, identifying a morphological difference of InS$^{exp}$'s, depending on freezing/thawing and the number of passages.

In addition, for the $InS^{exp}$, it was identified through a microscope whether a morphological difference is observed in a case of being subjected to freezing and thawing or depending on the number of passages. As a result, no morphological difference was observed for the $InS^{exp}$) in a case of being subjected to freezing and thawing or depending on the number of passages (FIG. 44).

Experimental Example 8. Identification of Characteristics of $InS^{exp}$-Derived Functional hIECs as Human Intestinal Epithelial Model Experimental Example 8.1. Identification of Expression of Marker Genes Related to Apical Side and Basolateral Side of Cell Membrane in $InS^{exp}$ For the $InS^{exp}$-derived immature hIECs and functional hIECs obtained in Example 5, the expression levels of VIL1, which is a marker gene related to the apical side of the cell membrane, and Na$^+$—K$^+$ ATPase, which is a marker gene related to the basolateral side of the cell membrane, were checked through immunofluorescence staining in the same manner as in Experimental Example 4.5.

Figure 45:
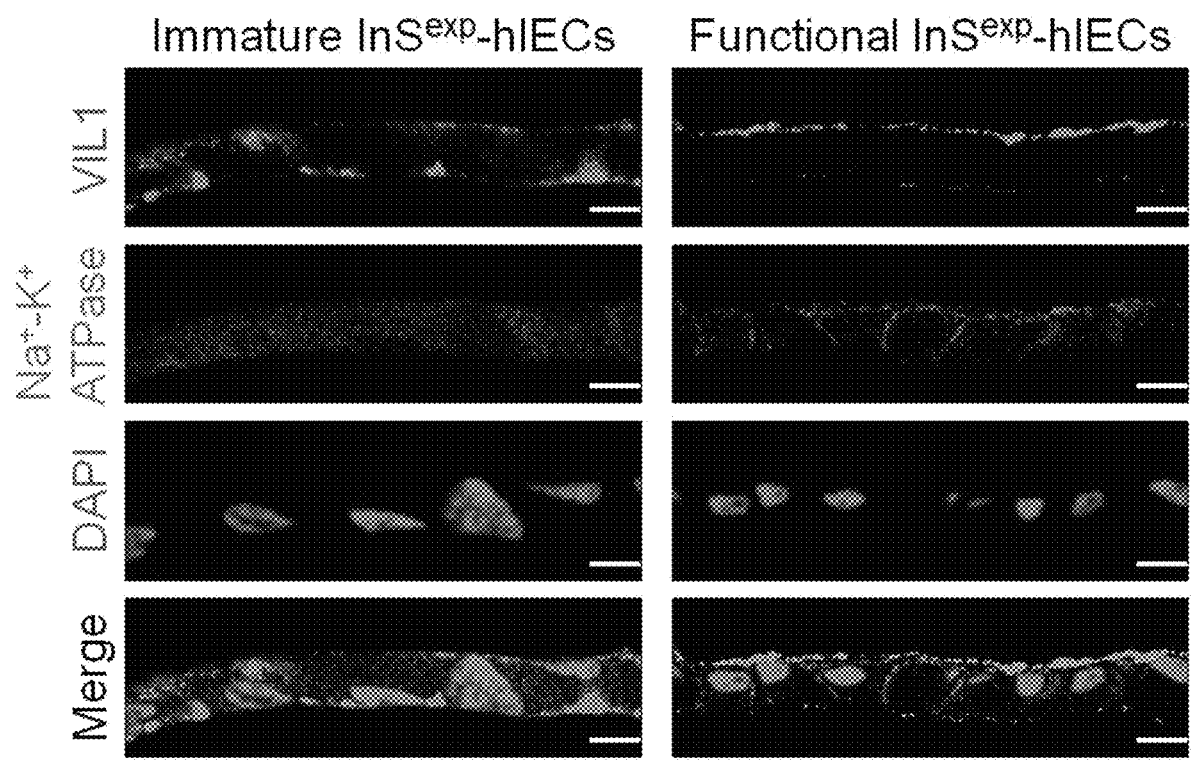
FIG. 45 illustrates results obtained by identifying, through immunofluorescence staining, expression levels of VIL1, which is a marker gene related to the apical side of the cell membrane, and Na$^+$—K$^+$ ATPase, which is a marker gene related to the basolateral side of the cell membrane, in InS$^{exp}$-derived immature hIECs and InS$^{exp}$-derived functional hIECs.

As a result, it was identified that as compared with the immature hIECs, the functional hIECs formed a structurally polarized monolayer in polarization distribution of the apical (VIL1) and basolateral (Na$^+$—K$^+$ ATPase) cell surface proteins (FIG. 45). From these results, it was identified that the functional hIECs had a superior barrier function to the immature hIECs.

Experimental Example 8.2. Identification I of Expression of Marker Genes Related to Intestinal and Secretory Cells in InS$^{exp}$-Derived Functional hIECs The expression levels of marker genes related to intestinal and secretory cells in hSI, hIO, InS$^{exp}$, InS$^{exp}$-derived immature hIECs, InS$^{exp}$-derived functional hIECs, and Caco-2 cell line were checked through qPCR analysis. qPCR was performed in the same manner as in Experimental Example 4.2.

Figure 46:
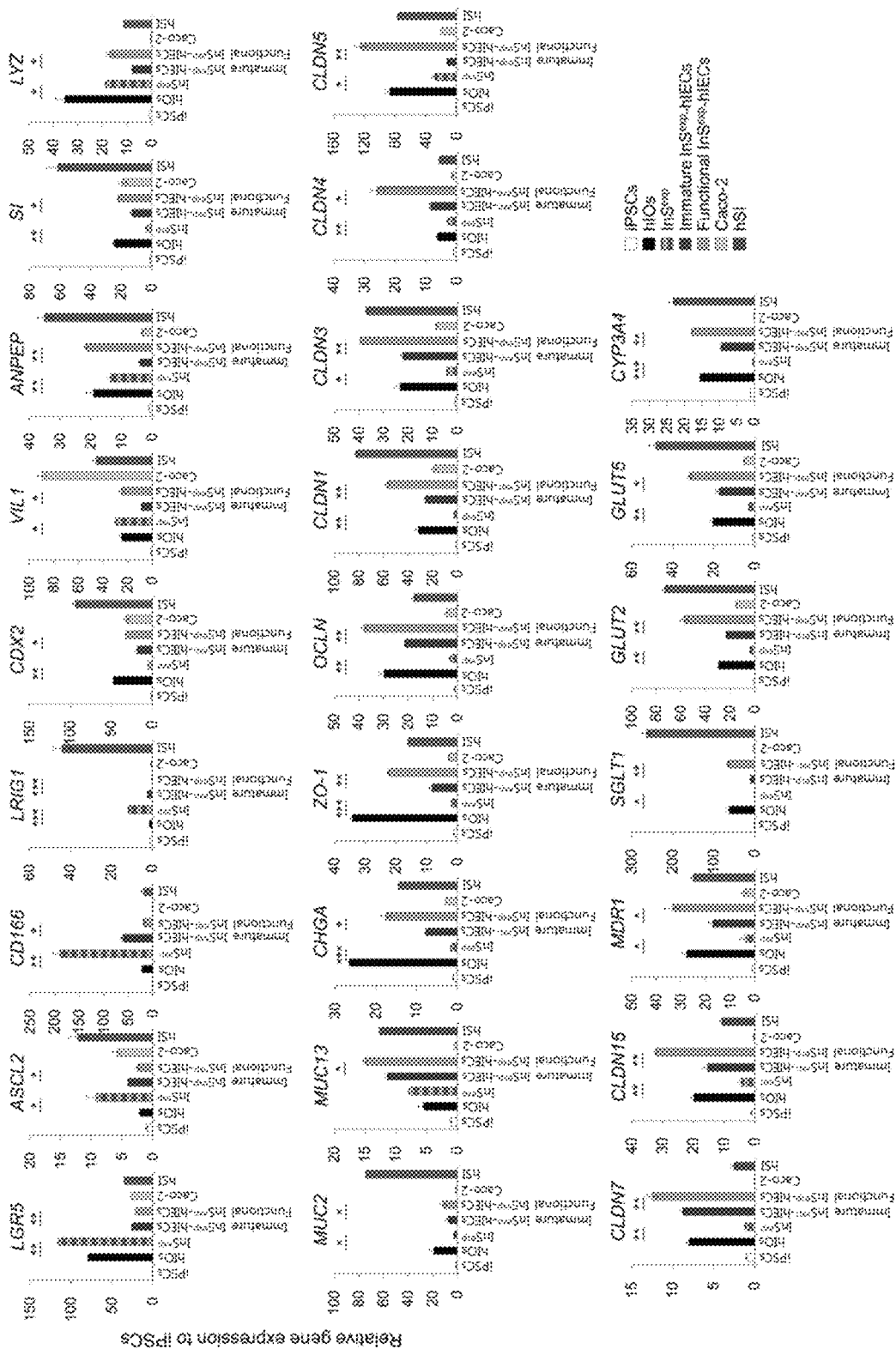
FIG. 46 illustrates graphs, showing expression levels of LGR5, ASCL2, CD166, LRIG1, CDX2, VIL1, ANPEP, SI, LYZ, MUC2, MUC13, CHGA, ZO-1, OCLN, CLDN1, CLDN3, CLDN4, CLDN5, CLDN7, CLDN15, MDR1, SGLT1, GLUT2, GLUTS, and CYP3A4 genes in InS$^{exp}$-derived immature hIECs and InS$^{exp}$-derived functional hIECs.

As a result, the functional hIECs showed significantly decreased expression levels of LGR5, ASCL2, and CD166 genes. In addition, it was identified that as compared with the immature hIECs, the functional hIECs showed significantly increased expression levels of CDX2, VIL1, ANPEP, SI, LYZ, MUC2, MUC13, CHGA, ZO-1, OCLN, CLDN1, CLDN3, CLDN4, CLDN5, CLDN7, CLDN15, MDR1, SGLT1, GLUT2, GLUT5, and CYP3A4, which are major intestinal cell-specific markers (FIG. 46).

Experimental Example 8.3. Identification of Barrier Function of InS$^{exp}$-Derived Functional hIECs For the InS$^{exp}$-derived immature hIECs and functional hIECs in Example 5, their barrier function was identified by continuously measuring the transepithelial electrical resistance (TEER) values during the culture period. Here, the measurement of TEER was performed using an epithelial tissue volt-ohm-meter (EVOM2, WPI, Sarasota, FL, USA) according to the manufacturer's manual.

Figure 47:
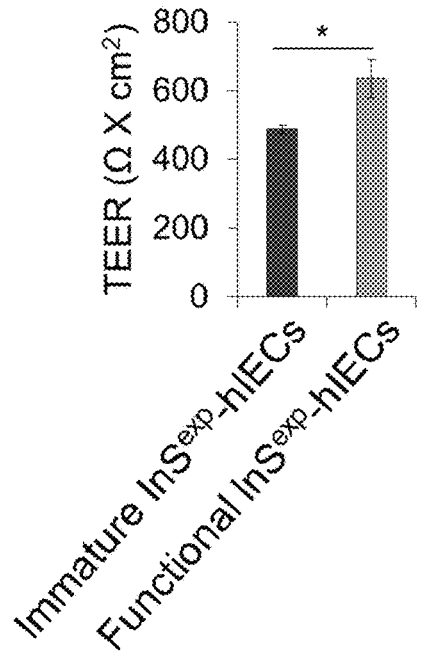
FIG. 47 illustrates a graph, showing a transepithelial electric resistance (TEER) value of InS$^{exp}$-derived immature hIECs and InS$^{exp}$-derived functional hIECs.

As a result, the TEER value of the immature hIECs was measured as 487.20±13.86 Ω*cm$^2$, and the TEER value of the functional hIECs was measured as 635.41±43.29 Ω*cm$^2$. From these results, it was identified that the TEER value of the functional hIECs was higher than that of the immature hIECs (FIG. 47).

Experimental Example 8.4. Identification of Expression and Activity of CYP3A4 in InS$^{exp}$-Derived Functional hIECs For the InS$^{exp}$-derived immature hIECs and functional hIECs in Example 5, CYP3A4 gene expression and CYP3A4 enzyme activity therein were analyzed in the same manner as in Experimental Example 4.8. Here, the CYP3A4 gene expression and the CYP3A4 enzyme activity were analyzed in the same manner as in Experimental Example 4.8.

Figure 48:
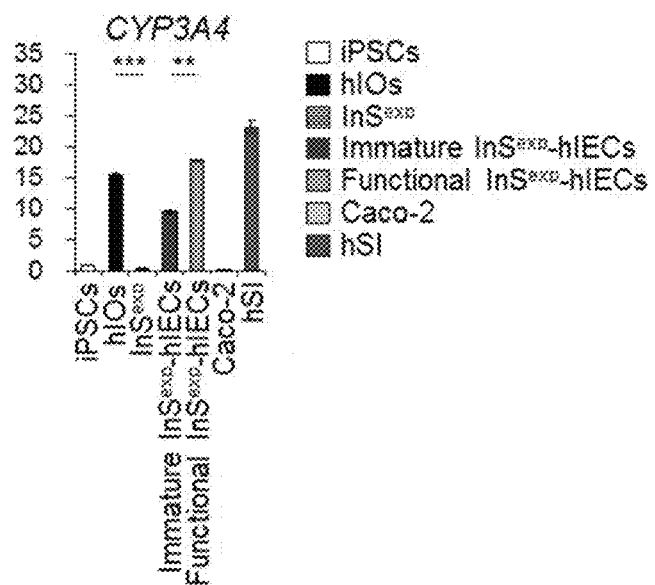
FIG. 48 illustrates a graph, showing an expression level of CYP3A4 gene in InS$^{exp}$-derived immature hIECs and InS$^{exp}$-derived functional hIECs.
Figure 49:
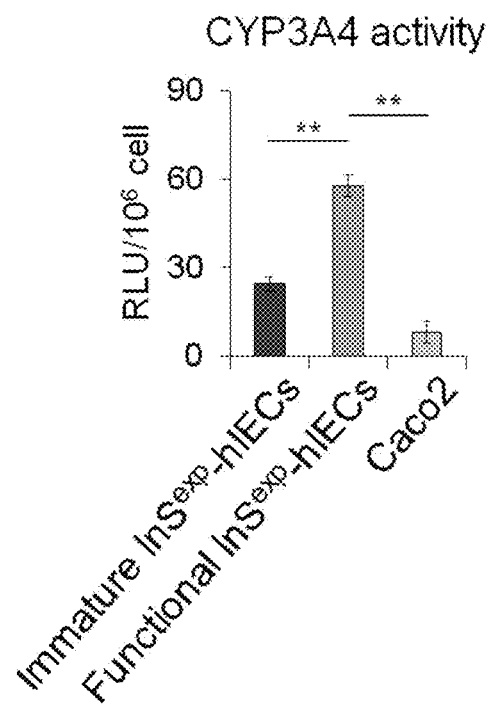
FIG. 49 illustrates a graph, showing activity of CYP3A4 enzyme in InS$^{exp}$-derived immature hIECs and InS$^{exp}$-derived functional hIECs.

As a result, it was identified that the functional hIECs showed an increased expression level of CYP3A4 as compared with the immature hIECs (FIG. 48). In addition, it was identified that the functional hIECs showed remarkably increased CYP3A4 enzyme activity as compared with the immature hIECs (FIG. 49).

IV. Utilization of Functional hIECs as Human Intestinal Epithelium Model

Experimental Example 9. Prediction of Drug Availability Using Human Intestinal Epithelial Model To identify an effect of the metabolic activity of CYP3A4 on first-pass availability of nifedipine in the intestine, analysis of CYP3A4-mediated metabolism of nifedipine was performed. The analysis was performed using LC-MS/MS, where dihydro-nifedipine, which is a major active metabolite of nifedipine, was checked.

The immature hIECs prepared in Comparative Example 1, the functional hIECs prepared in Example 2, and the Caco-2 cell line (each at 1.34×10$^5$ cells/cm$^2$) were re-dispensed into a Transwell insert coated with 1% Matrigel, together with a culture medium, and culture was performed for 14 days. Before drug treatment, the TEER value was measured to evaluate the cell status, and only the cells with a TEER value of 200 Ω*cm$^2$ or higher were used. For inhibition of CYP3A4, the respective cells were treated with 1 µM ketoconazole before performing analysis of CYP3A4-mediated metabolism, and incubated at 37° C. for 2 hours. Thereafter, washing was performed 3 times with a transport buffer containing 1× Hank's balanced salt solution (HBSS; Thermo Fisher Scientific Inc.), 0.35 g/L of sodium bicarbonate (Sigma-Aldrich), and 10 mM HEPES (Thermo Fisher Scientific Inc.). 500 µl of transport buffer containing 5 µM nifedipine (Sigma-Aldrich) was added to the apical side of Transwell, and 1.5 ml of transport buffer was added to the basolateral side of Transwell. After incubation for 2 hours, the supernatant at each of the apical side and the basolateral side was separately obtained in a new tube. Liquid chromatography-electrospray ionization/mass spectrometry (LC-ESI/MS) MS analysis was performed using 4000 QTRAP LCMS/MS system (Applied Biosystems) equipped with Turbo VTM ion source and Agilent 1200 series high performance liquid chromatography (HPLC; Agilent Technologies, Palo Alto, CA, USA). The concentrations of nifedipine and dihydro-nifedipine in each supernatant were quantified.

Figure 50:
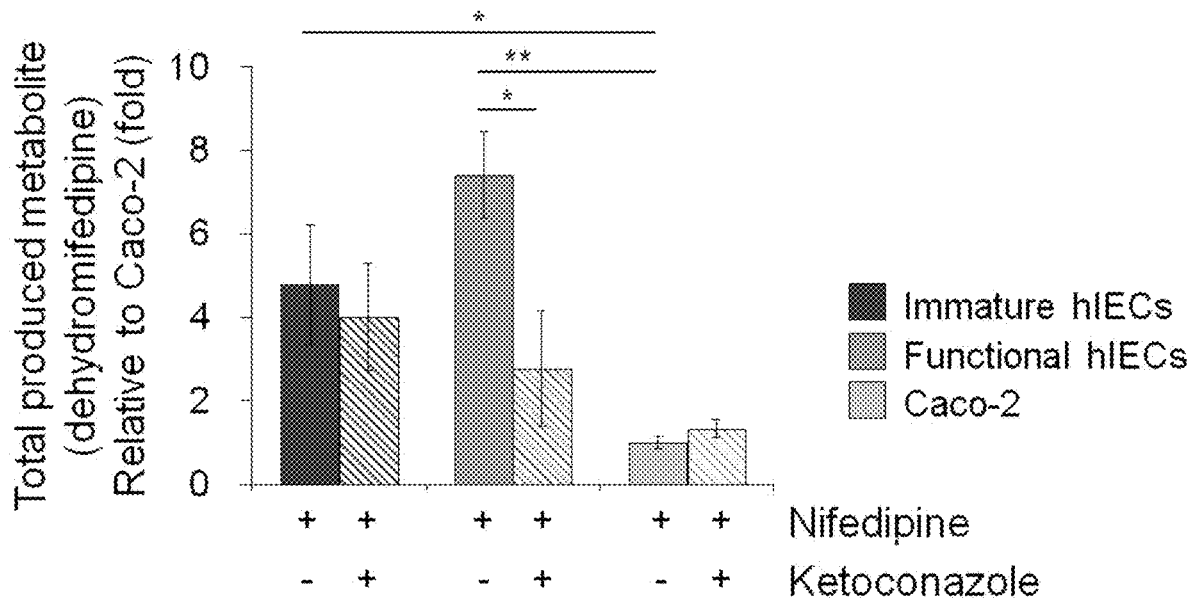
FIG. 50 illustrates a graph, showing results obtained by analyzing CYP3A4-mediated metabolism in immature hIECs and functional hIECs.

As a result, regarding the concentration of dihydro-nifedipine, as compared with the Caco-2 cell line, the immature hIECs showed an about 4.5-fold increase (p<0.05) and the functional hIECs showed a 7.4-fold increase (p<0.01). In a case of being treated with ketoconazole, which is a CYP3A4 inhibitor, the functional hIECs showed a concentration of dihydro-nifedipine which was decreased by 62.5% or higher (p<0.01). On the other hand, the immature hIECs and the Caco-2 cell line showed a concentration of dihydro-nifedipine which was not significantly changed (FIG. 50).

Experimental Example 10. Measurement of Drug Bioavailability in Human Body Using Human Intestinal Epithelial Model As a model for predicting drug bioavailability in a human body, which is intended to perform ex vivo drug absorption analysis using a test drug, the functional hIECs were evaluated for their utility.

The cells were prepared in the same manner as in Experimental Example 6.1. The functional hIECs and the Caco-2 cell line were washed 3 times with a transport buffer. For permeability analysis, 500 µl of transport buffer was added to the apical side of Transwell, together with 10 µM of metoprolol (Sigma-Aldrich), propranolol (Sigma-Aldrich), or diclofenac (Sigma-Aldrich), or 20 µM of ranitidine (Sigma-Aldrich), and 1.5 ml of transport buffer was added to the basolateral side of Transwell. After incubation for 2 hours, the supernatant at each of the apical side and the basolateral side was separately obtained in a new tube. The concentration of each compound in the sample was analyzed using LC-MS/MS. The apparent permeability coefficient was calculated according to the following equation.

$$P_{app} = \frac{dQ/dt}{A \times C_0}$$

In the equation, dQ/dt, A, and $C_0$ represent a transport rate, a surface area of the insert, and an initial concentration of the compound in the donor compartment, respectively. Chromatographic quantification of each compound was performed using an LC-tandem mass spectrometry system equipped with Shimadzu Prominence UPLC system (Shimadzu, Kyoto, Japan) and API 2000 QTRAP mass spectrometer (Applied Biosystems, Foster City, CA, USA).

An aliquot (50 µl) of the sample was mixed with an acetonitrile solution containing an internal standard (50 ng/ml of carbamazepine for metoprolol, ranitidine, and propranolol, and 500 ng/ml of 4-methylumbelliferone for diclofenac), and centrifugation was performed with 3,000×g for 10 minutes at 4° C. Then, an aliquot (10 µl) of the supernatant was injected directly into the LC-MS/MS system. Separation was performed using a Waters XTerra MS C18 column (2.1×50 mm, 5 µm, Milford, MA, USA) with a concentration gradient of 0.1% formic acid in acetonitrile and 0.1% formic acid in water at a flow rate of 0.4 ml/min. Transitions were made as follows to detect the analyte: m/z 268.0→116.2 (metoprolol), m/z 294.00→250.10 (diclofenac), m/z 314.90→176.10 (ranitidine), m/z 260.00→56.00 (propranolol), m/z 237.0→194.0 for carbamazepine, m/z 175.0→119.0 for 4-methylumbelliferone.

As a result, $P_{app}$ values for propranolol and diclofenac were 32.29±2.61 and 36.23±1.49 (×10$^{-6}$ cm/sec), respectively, in the Caco-2 cell line, whereas such $P_{app}$ values were 11.02±1.28 and 9.82±0.04 (×10$^{-6}$ cm/sec), respectively, in the functional hIECs. In addition, it was identified that $P_{app}$ values for metoprolol, which is a highly permeable and soluble drug, and ranitidine, which is a low permeable drug, were 36.54±1.09 and 0.98±0.02 (×10$^{-6}$ cm/sec), respectively, in the Caco-2 cell line, and such $P_{app}$ values were 11.10±1.15 and 6.98±0.66 (×10$^{-6}$ cm/sec), respectively, in the functional hIECs (FIG. 51).

$P_{app}$ values for the compounds were used to predict the fraction ($F_{intestine}$) absorbed in the human intestine, which can be expressed as Fa (absorbed fraction) or Fg (intestinal availability related to metabolism). Specifically, according to the values reported by Michaelis and Menten, the $F_{intestine}$ values for metoprolol and ranitidine are 0.82 and 0.66, respectively, and $F_{intestine}=F_{intestine, max}*P_{app}$ (×10$^{-6}$ cm/sec)/[Km+$P_{app}$ (×10$^{-6}$ cm/sec)], where Km represents a $P_{app}$ value in a case where the $F_{intestine}$ is 50% of $F_{intestine, max}$, $F_{intestine, max}=1$ (that is, theoretical maximum $F_{intestine}$ value), and $F_{intestine, 0}=0$ (theoretical minimum $F_{intestine}$ value). Km was estimated to be 0.53 [coefficient of variance (CV), 32.58%] and 3.09 (CV, 8.97%) in the Caco-2 cell and the hIECs, respectively.

Figures 51, 52:
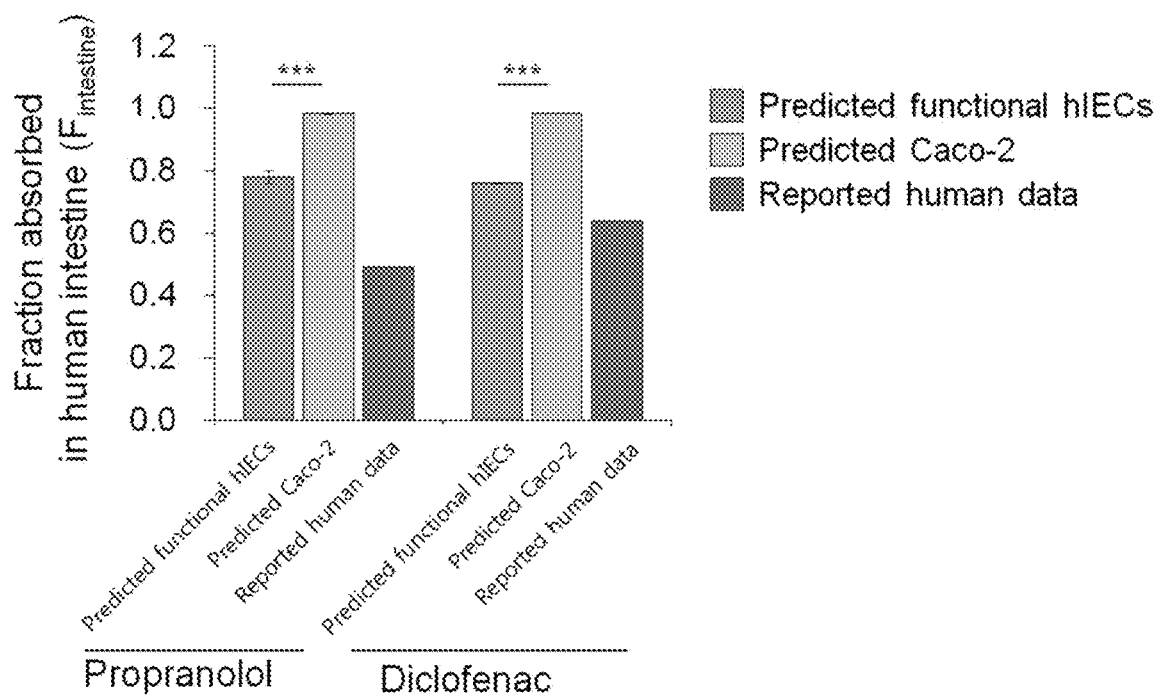
FIG. 51 illustrates a diagram, summarizing $P_{app}$ analysis values of metoprolol, propranolol, diclofenac, and ranitidine using functional hIECs and Caco-2 cell line, and prediction values for fraction absorbed in human intestine ($F_{intestine}$), absorbed fraction ($F_a$), and intestinal availability related to metabolism ($F_g$), which are obtained by using the $P_{app}$ analysis values.
FIG. 52 illustrates a graph obtained by comparing $F_{intestine}$ values of propranolol and diclofenac using functional hIECs and Caco-2 cell line with $F_{intestine}$ values from known human absorption data for propranolol and diclofenac.

Using the above-established equation, the $F_{intestine}$ values for propranolol and diclofenac, each of which has a low Fg value after intestinal metabolism, were estimated to be 0.98 and 0.99, respectively, in the Caco-2 cell line, and 0.78 and 0.76, respectively, in the functional hIECs (FIG. 52). According to the published human absorption data, the $F_{intestine}$ values for propranolol and diclofenac were 0.49 and 0.64, respectively; and it was identified that these values were similar to the $F_{intestine}$ values for propranolol and diclofenac in the functional hIECs. From these results, it was identified that the functional hIECs can better predict the absorption and range for human oral drug bioavailability.

Experimental Example 11. Identification of Engraftment and Clustering of Intestinal Microorganism Using Human Intestinal Epithelial Model To identify the difference in engraftment and clustering of an intestinal microorganism depending on the functionality of a human intestinal epithelial model, a colony forming unit assay was performed. The immature hIECs, the functional hIECs, and the Caco-2 cells (each at 1.34×10$^5$ cells/cm$^2$) were cultured in Transwell for 14 days to differentiate. Then, washing was performed 3 times to remove residual antibiotics. Subsequently, the cells were treated with 1×10$^9$ intestinal microorganism (*Lactobacillus plantarum*—RFP), and co-culture was performed for 2 hours. Treatment with trypsin-EDTA was performed for 10 minutes. Then, serial dilution was performed with PBS, and smearing was performed on a nutrient medium (de Man, Rogosa and Sharpe, MRS) selective for lactic acid bacteria. Incubation was performed in an incubator at 37° C. for 2 days, and then the number of colonies formed was counted.

Figure 53:
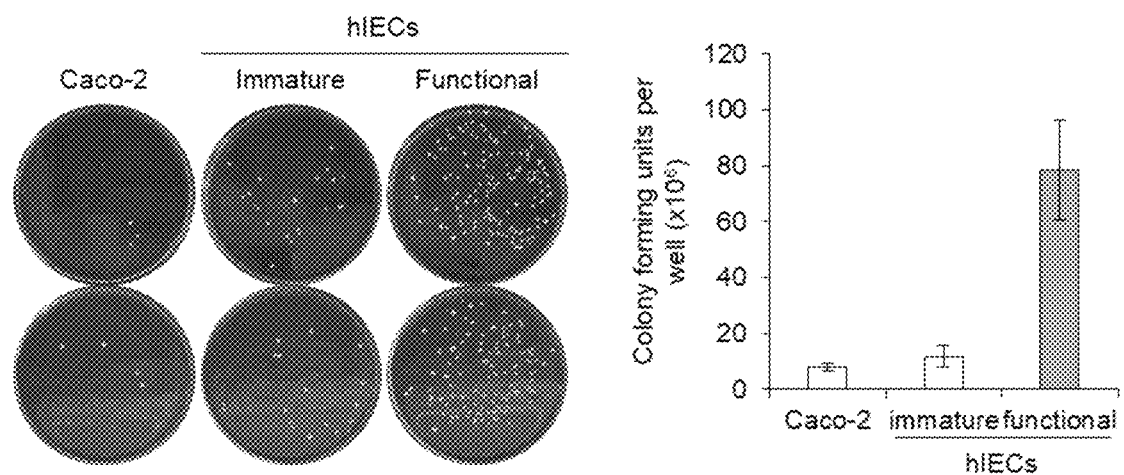
FIG. 53 illustrates a diagram and a graph, identifying engraftment and proliferation capacity of an intestinal microorganism (*Lactobacillus plantarum*—RFP) in immature hIECs, functional hIECs, and Caco-2 cell line.

As a result, as compared with the Caco-2 cell line, the immature hIECs showed an about 1.46-fold increase and the functional hIECs showed a 9.83-fold increase (FIG. 53).

Statistical Analysis

All experiments were repeated three or more times, and the results are expressed as mean±standard error (SEM). Statistic significance of the data was determined using a two-sided student's t-test.

The invention claimed is:

1. A method for differentiating human intestinal epithelial cell (hIEC) progenitors from definitive endoderm cells, comprising:
culturing the definitive endoderm cells in a medium comprising epidermal growth factor (EGF), R-spondin 1, and insulin,
wherein the medium does not comprise any additive selected from the group consisting of Wnt-3A, Noggin, and SB202190, and
wherein the definitive endoderm cells are cultured for a sufficient amount of time to establish hIEC progenitors.

2. The method of claim 1, wherein the definitive endoderm cells are differentiated from human pluripotent stem cells (hPSCs).

3. The method according to claim 1, wherein the medium further comprises DMEM/F12, FBS, N2 supplement, L-glutamine, non-essential amino acids (NEAA), and HEPES buffer.

4. The method according to claim 3, wherein the medium comprises 2% FBS, 1% N2 supplement, 2 mM L-glutamine, 1% NNEA, and 15 nM HEPES buffer.

5. The method according to claim 1, wherein the medium further comprises 100 ng/mL EGF, 100 ng/mL R-spondin 1, and 5 µg/mL insulin.

* * * * *

SEQUENCE LISTING

<160> NUMBER OF SEQ ID NOS: 90

<210> SEQ ID NO 1
<211> LENGTH: 20
<212> TYPE: DNA
<213> ORGANISM: Artificial Sequence
<220> FEATURE:
<223> OTHER INFORMATION: forward primer for LGR5

```
<400> SEQUENCE: 1
tgctcttcac caactgcatc                                                   20

<210> SEQ ID NO 2
<211> LENGTH: 20
<212> TYPE: DNA
<213> ORGANISM: Artificial Sequence
<220> FEATURE:
<223> OTHER INFORMATION: reverse primer for LGR5

<400> SEQUENCE: 2
ctcaggctca ccagatcctc                                                   20

<210> SEQ ID NO 3
<211> LENGTH: 20
<212> TYPE: DNA
<213> ORGANISM: Artificial Sequence
<220> FEATURE:
<223> OTHER INFORMATION: forward primer for ASCL2

<400> SEQUENCE: 3
cgtgaagctg gtgaacttgg                                                   20

<210> SEQ ID NO 4
<211> LENGTH: 20
<212> TYPE: DNA
<213> ORGANISM: Artificial Sequence
<220> FEATURE:
<223> OTHER INFORMATION: reverse primer for ASCL2

<400> SEQUENCE: 4
ggatgtactc cacggctgag                                                   20

<210> SEQ ID NO 5
<211> LENGTH: 20
<212> TYPE: DNA
<213> ORGANISM: Artificial Sequence
<220> FEATURE:
<223> OTHER INFORMATION: forward primer for CD166

<400> SEQUENCE: 5
tcaaggtgtt caagcaacca                                                   20

<210> SEQ ID NO 6
<211> LENGTH: 20
<212> TYPE: DNA
<213> ORGANISM: Artificial Sequence
<220> FEATURE:
<223> OTHER INFORMATION: reverse primer for CD166

<400> SEQUENCE: 6
ctgaaatgca gtcacccaac                                                   20

<210> SEQ ID NO 7
<211> LENGTH: 19
<212> TYPE: DNA
<213> ORGANISM: Artificial Sequence
<220> FEATURE:
<223> OTHER INFORMATION: forward primer for LRIG1

<400> SEQUENCE: 7
gaccctttct gaccgacaa                                                    19

<210> SEQ ID NO 8
```

-continued

```
<211> LENGTH: 18
<212> TYPE: DNA
<213> ORGANISM: Artificial Sequence
<220> FEATURE:
<223> OTHER INFORMATION: reverse primer for LRIG1

<400> SEQUENCE: 8
cgctttccac ggctcttt                                                   18

<210> SEQ ID NO 9
<211> LENGTH: 22
<212> TYPE: DNA
<213> ORGANISM: Artificial Sequence
<220> FEATURE:
<223> OTHER INFORMATION: forward primer for CDX2

<400> SEQUENCE: 9
ctggagctgg agaaggagtt tc                                              22

<210> SEQ ID NO 10
<211> LENGTH: 24
<212> TYPE: DNA
<213> ORGANISM: Artificial Sequence
<220> FEATURE:
<223> OTHER INFORMATION: reverse primer for CDX2

<400> SEQUENCE: 10
attttaacct gcctctcaga gagc                                            24

<210> SEQ ID NO 11
<211> LENGTH: 20
<212> TYPE: DNA
<213> ORGANISM: Artificial Sequence
<220> FEATURE:
<223> OTHER INFORMATION: forward primer for VIL1

<400> SEQUENCE: 11
agccagatca ctgctgaggt                                                 20

<210> SEQ ID NO 12
<211> LENGTH: 20
<212> TYPE: DNA
<213> ORGANISM: Artificial Sequence
<220> FEATURE:
<223> OTHER INFORMATION: reverse primer for VIL1

<400> SEQUENCE: 12
tggacaggtg ttcctccttc                                                 20

<210> SEQ ID NO 13
<211> LENGTH: 20
<212> TYPE: DNA
<213> ORGANISM: Artificial Sequence
<220> FEATURE:
<223> OTHER INFORMATION: forward primer for ANPEP

<400> SEQUENCE: 13
aagcctgttt cctcgttgtc                                                 20

<210> SEQ ID NO 14
<211> LENGTH: 20
<212> TYPE: DNA
<213> ORGANISM: Artificial Sequence
<220> FEATURE:
<223> OTHER INFORMATION: reverse primer for ANPEP

<400> SEQUENCE: 14
```

```
aacctcatcc aggcagtgac                                              20

<210> SEQ ID NO 15
<211> LENGTH: 20
<212> TYPE: DNA
<213> ORGANISM: Artificial Sequence
<220> FEATURE:
<223> OTHER INFORMATION: forward primer for SI

<400> SEQUENCE: 15
ggtaaggaga aaccgggaag                                              20

<210> SEQ ID NO 16
<211> LENGTH: 20
<212> TYPE: DNA
<213> ORGANISM: Artificial Sequence
<220> FEATURE:
<223> OTHER INFORMATION: reverse primer for SI

<400> SEQUENCE: 16
gcacgtcgac ctatggaaat                                              20

<210> SEQ ID NO 17
<211> LENGTH: 21
<212> TYPE: DNA
<213> ORGANISM: Artificial Sequence
<220> FEATURE:
<223> OTHER INFORMATION: forward primer for LYZ

<400> SEQUENCE: 17
aaaaccccag gagcagttaa t                                            21

<210> SEQ ID NO 18
<211> LENGTH: 20
<212> TYPE: DNA
<213> ORGANISM: Artificial Sequence
<220> FEATURE:
<223> OTHER INFORMATION: reverse primer for LYZ

<400> SEQUENCE: 18
caaccctctt tgcacaagct                                              20

<210> SEQ ID NO 19
<211> LENGTH: 20
<212> TYPE: DNA
<213> ORGANISM: Artificial Sequence
<220> FEATURE:
<223> OTHER INFORMATION: forward primer for MUC2

<400> SEQUENCE: 19
tgtaggcatc gctcttctca                                              20

<210> SEQ ID NO 20
<211> LENGTH: 20
<212> TYPE: DNA
<213> ORGANISM: Artificial Sequence
<220> FEATURE:
<223> OTHER INFORMATION: reverse primer for MUC2

<400> SEQUENCE: 20
gacaccatct acctcacccg                                              20

<210> SEQ ID NO 21
<211> LENGTH: 20
<212> TYPE: DNA
```

```
<213> ORGANISM: Artificial Sequence
<220> FEATURE:
<223> OTHER INFORMATION: forward primer for CHGA

<400> SEQUENCE: 21
tgacctcaac gatgcatttc                                                 20

<210> SEQ ID NO 22
<211> LENGTH: 20
<212> TYPE: DNA
<213> ORGANISM: Artificial Sequence
<220> FEATURE:
<223> OTHER INFORMATION: reverse primer for CHGA

<400> SEQUENCE: 22
ctgtcctggc tcttctgctc                                                 20

<210> SEQ ID NO 23
<211> LENGTH: 20
<212> TYPE: DNA
<213> ORGANISM: Artificial Sequence
<220> FEATURE:
<223> OTHER INFORMATION: forward primer for ZO-1

<400> SEQUENCE: 23
cccgaccatt tgaacgcaag                                                 20

<210> SEQ ID NO 24
<211> LENGTH: 20
<212> TYPE: DNA
<213> ORGANISM: Artificial Sequence
<220> FEATURE:
<223> OTHER INFORMATION: reverse primer for ZO-1

<400> SEQUENCE: 24
atgcccatga actcagcacg                                                 20

<210> SEQ ID NO 25
<211> LENGTH: 20
<212> TYPE: DNA
<213> ORGANISM: Artificial Sequence
<220> FEATURE:
<223> OTHER INFORMATION: forward primer for OCLN

<400> SEQUENCE: 25
cattgccatc tttgcctgtg                                                 20

<210> SEQ ID NO 26
<211> LENGTH: 21
<212> TYPE: DNA
<213> ORGANISM: Artificial Sequence
<220> FEATURE:
<223> OTHER INFORMATION: reverse primer for OCLN

<400> SEQUENCE: 26
agccataacc atagccatag c                                               21

<210> SEQ ID NO 27
<211> LENGTH: 20
<212> TYPE: DNA
<213> ORGANISM: Artificial Sequence
<220> FEATURE:
<223> OTHER INFORMATION: forward primer for CLDN1

<400> SEQUENCE: 27
cccagtcaat gccaggtacg                                                 20
```

```
<210> SEQ ID NO 28
<211> LENGTH: 20
<212> TYPE: DNA
<213> ORGANISM: Artificial Sequence
<220> FEATURE:
<223> OTHER INFORMATION: reverse primer for CLDN1

<400> SEQUENCE: 28
gggccttggt gttgggtaag                                          20

<210> SEQ ID NO 29
<211> LENGTH: 20
<212> TYPE: DNA
<213> ORGANISM: Artificial Sequence
<220> FEATURE:
<223> OTHER INFORMATION: forward primer for CLDN3

<400> SEQUENCE: 29
caggctacga ccgcaaggac                                          20

<210> SEQ ID NO 30
<211> LENGTH: 20
<212> TYPE: DNA
<213> ORGANISM: Artificial Sequence
<220> FEATURE:
<223> OTHER INFORMATION: reverse primer for CLDN3

<400> SEQUENCE: 30
ggtggtggtg gtggtgttgg                                          20

<210> SEQ ID NO 31
<211> LENGTH: 20
<212> TYPE: DNA
<213> ORGANISM: Artificial Sequence
<220> FEATURE:
<223> OTHER INFORMATION: forward primer for CLDN5

<400> SEQUENCE: 31
gcagcccctg tgaagattga                                          20

<210> SEQ ID NO 32
<211> LENGTH: 20
<212> TYPE: DNA
<213> ORGANISM: Artificial Sequence
<220> FEATURE:
<223> OTHER INFORMATION: reverse primer for CLDN5

<400> SEQUENCE: 32
gtctctggca aaagcggtg                                           20

<210> SEQ ID NO 33
<211> LENGTH: 19
<212> TYPE: DNA
<213> ORGANISM: Artificial Sequence
<220> FEATURE:
<223> OTHER INFORMATION: forward primer for ATOH11

<400> SEQUENCE: 33
gtccgagctg ctacaaacg                                           19

<210> SEQ ID NO 34
<211> LENGTH: 18
<212> TYPE: DNA
<213> ORGANISM: Artificial Sequence
<220> FEATURE:
```

<223> OTHER INFORMATION: reverse primer for ATOH11

<400> SEQUENCE: 34
gtggtggtgg tcgctttt                                        18

<210> SEQ ID NO 35
<211> LENGTH: 19
<212> TYPE: DNA
<213> ORGANISM: Artificial Sequence
<220> FEATURE:
<223> OTHER INFORMATION: forward primer for HES1

<400> SEQUENCE: 35
agtgaagcac ctccggaac                                       19

<210> SEQ ID NO 36
<211> LENGTH: 18
<212> TYPE: DNA
<213> ORGANISM: Artificial Sequence
<220> FEATURE:
<223> OTHER INFORMATION: reverse primer for HES1

<400> SEQUENCE: 36
cgttcatgca ctcgctga                                        18

<210> SEQ ID NO 37
<211> LENGTH: 22
<212> TYPE: DNA
<213> ORGANISM: Artificial Sequence
<220> FEATURE:
<223> OTHER INFORMATION: forward primer for AXIN2

<400> SEQUENCE: 37
gagtggactt gtgccgactt ca                                   22

<210> SEQ ID NO 38
<211> LENGTH: 22
<212> TYPE: DNA
<213> ORGANISM: Artificial Sequence
<220> FEATURE:
<223> OTHER INFORMATION: reverse primer for AXIN2

<400> SEQUENCE: 38
ggtggctggt gcaaagacat ag                                   22

<210> SEQ ID NO 39
<211> LENGTH: 25
<212> TYPE: DNA
<213> ORGANISM: Artificial Sequence
<220> FEATURE:
<223> OTHER INFORMATION: forward primer for CTNNB1

<400> SEQUENCE: 39
tctgaggaca agccacaaga ttaca                                25

<210> SEQ ID NO 40
<211> LENGTH: 22
<212> TYPE: DNA
<213> ORGANISM: Artificial Sequence
<220> FEATURE:
<223> OTHER INFORMATION: reverse primer for CTNNB1

<400> SEQUENCE: 40
tgggcaccaa tatcaagtcc aa                                   22

```
<210> SEQ ID NO 41
<211> LENGTH: 20
<212> TYPE: DNA
<213> ORGANISM: Artificial Sequence
<220> FEATURE:
<223> OTHER INFORMATION: forward primer for MDR1

<400> SEQUENCE: 41
gccaaagcca aaatatcagc                                               20

<210> SEQ ID NO 42
<211> LENGTH: 20
<212> TYPE: DNA
<213> ORGANISM: Artificial Sequence
<220> FEATURE:
<223> OTHER INFORMATION: reverse primer for MDR1

<400> SEQUENCE: 42
ttccaatgtg ttcggcatta                                               20

<210> SEQ ID NO 43
<211> LENGTH: 20
<212> TYPE: DNA
<213> ORGANISM: Artificial Sequence
<220> FEATURE:
<223> OTHER INFORMATION: forward primer for SGLT1

<400> SEQUENCE: 43
gtgcagtcag cacaaagtgg                                               20

<210> SEQ ID NO 44
<211> LENGTH: 20
<212> TYPE: DNA
<213> ORGANISM: Artificial Sequence
<220> FEATURE:
<223> OTHER INFORMATION: reverse primer for SGLT1

<400> SEQUENCE: 44
atgcacatcc ggaatgggtt                                               20

<210> SEQ ID NO 45
<211> LENGTH: 24
<212> TYPE: DNA
<213> ORGANISM: Artificial Sequence
<220> FEATURE:
<223> OTHER INFORMATION: forward primer for GLUT2

<400> SEQUENCE: 45
ggccagcagg ttcatcatca gcat                                          24

<210> SEQ ID NO 46
<211> LENGTH: 24
<212> TYPE: DNA
<213> ORGANISM: Artificial Sequence
<220> FEATURE:
<223> OTHER INFORMATION: reverse primer for GLUT2

<400> SEQUENCE: 46
ccttgggctg aggaagagac tgtg                                          24

<210> SEQ ID NO 47
<211> LENGTH: 20
<212> TYPE: DNA
<213> ORGANISM: Artificial Sequence
<220> FEATURE:
<223> OTHER INFORMATION: forward primer for GLUT5
```

```
<400> SEQUENCE: 47
cgccaagaaa gccctacaga                                                    20

<210> SEQ ID NO 48
<211> LENGTH: 20
<212> TYPE: DNA
<213> ORGANISM: Artificial Sequence
<220> FEATURE:
<223> OTHER INFORMATION: reverse primer for GLUT5

<400> SEQUENCE: 48
gcgctcaggt agatctggtc                                                    20

<210> SEQ ID NO 49
<211> LENGTH: 20
<212> TYPE: DNA
<213> ORGANISM: Artificial Sequence
<220> FEATURE:
<223> OTHER INFORMATION: forward primer for OSTP-beta

<400> SEQUENCE: 49
tgattggcta tggggctatc                                                    20

<210> SEQ ID NO 50
<211> LENGTH: 20
<212> TYPE: DNA
<213> ORGANISM: Artificial Sequence
<220> FEATURE:
<223> OTHER INFORMATION: reverse primer for OSTP-beta

<400> SEQUENCE: 50
catatcctca gggctggtgt                                                    20

<210> SEQ ID NO 51
<211> LENGTH: 20
<212> TYPE: DNA
<213> ORGANISM: Artificial Sequence
<220> FEATURE:
<223> OTHER INFORMATION: forward primer for ASBT

<400> SEQUENCE: 51
tataggatgc tgccctggag                                                    20

<210> SEQ ID NO 52
<211> LENGTH: 20
<212> TYPE: DNA
<213> ORGANISM: Artificial Sequence
<220> FEATURE:
<223> OTHER INFORMATION: reverse primer for ASBT

<400> SEQUENCE: 52
agtgtggagc atgtggtcat                                                    20

<210> SEQ ID NO 53
<211> LENGTH: 18
<212> TYPE: DNA
<213> ORGANISM: Artificial Sequence
<220> FEATURE:
<223> OTHER INFORMATION: forward primer for MCT1

<400> SEQUENCE: 53
gcgatccgcg catataac                                                      18

<210> SEQ ID NO 54
<211> LENGTH: 20
```

```
<212> TYPE: DNA
<213> ORGANISM: Artificial Sequence
<220> FEATURE:
<223> OTHER INFORMATION: reverse primer for MCT1

<400> SEQUENCE: 54
aactggacct ccaactgctg                                               20

<210> SEQ ID NO 55
<211> LENGTH: 20
<212> TYPE: DNA
<213> ORGANISM: Artificial Sequence
<220> FEATURE:
<223> OTHER INFORMATION: forward primer for OCT1

<400> SEQUENCE: 55
taatggacca catcgctcaa                                               20

<210> SEQ ID NO 56
<211> LENGTH: 20
<212> TYPE: DNA
<213> ORGANISM: Artificial Sequence
<220> FEATURE:
<223> OTHER INFORMATION: reverse primer for OCT1

<400> SEQUENCE: 56
agcccctgat agagcacaga                                               20

<210> SEQ ID NO 57
<211> LENGTH: 20
<212> TYPE: DNA
<213> ORGANISM: Artificial Sequence
<220> FEATURE:
<223> OTHER INFORMATION: forward primer for OST-alpha

<400> SEQUENCE: 57
gaagaccaat tacggcatcc                                               20

<210> SEQ ID NO 58
<211> LENGTH: 20
<212> TYPE: DNA
<213> ORGANISM: Artificial Sequence
<220> FEATURE:
<223> OTHER INFORMATION: reverse primer for OST-alpha

<400> SEQUENCE: 58
agtgagggca agttccacag                                               20

<210> SEQ ID NO 59
<211> LENGTH: 20
<212> TYPE: DNA
<213> ORGANISM: Artificial Sequence
<220> FEATURE:
<223> OTHER INFORMATION: forward primer for OST-beta

<400> SEQUENCE: 59
gagctgctgg aagagatgat                                               20

<210> SEQ ID NO 60
<211> LENGTH: 22
<212> TYPE: DNA
<213> ORGANISM: Artificial Sequence
<220> FEATURE:
<223> OTHER INFORMATION: reverse primer for OST-beta

<400> SEQUENCE: 60
```
tgcttataat gaccaccaca gc                                             22

<210> SEQ ID NO 61
<211> LENGTH: 21
<212> TYPE: DNA
<213> ORGANISM: Artificial Sequence
<220> FEATURE:
<223> OTHER INFORMATION: forward primer for BCRP

<400> SEQUENCE: 61
tgcaacatgt actggcgaag a                                              21

<210> SEQ ID NO 62
<211> LENGTH: 17
<212> TYPE: DNA
<213> ORGANISM: Artificial Sequence
<220> FEATURE:
<223> OTHER INFORMATION: reverse primer for BCRP

<400> SEQUENCE: 62
tcttccacag ccccagg                                                   17

<210> SEQ ID NO 63
<211> LENGTH: 20
<212> TYPE: DNA
<213> ORGANISM: Artificial Sequence
<220> FEATURE:
<223> OTHER INFORMATION: forward primer for MRP3

<400> SEQUENCE: 63
gtccgcagaa tggacttgat                                                20

<210> SEQ ID NO 64
<211> LENGTH: 20
<212> TYPE: DNA
<213> ORGANISM: Artificial Sequence
<220> FEATURE:
<223> OTHER INFORMATION: reverse primer for MRP3

<400> SEQUENCE: 64
tcaccacttg gggatcattt                                                20

<210> SEQ ID NO 65
<211> LENGTH: 20
<212> TYPE: DNA
<213> ORGANISM: Artificial Sequence
<220> FEATURE:
<223> OTHER INFORMATION: forward primer for GSTA

<400> SEQUENCE: 65
agccgggctg acattcatct                                                20

<210> SEQ ID NO 66
<211> LENGTH: 20
<212> TYPE: DNA
<213> ORGANISM: Artificial Sequence
<220> FEATURE:
<223> OTHER INFORMATION: reverse primer for GSTA

<400> SEQUENCE: 66
tggcctccat gactgcgtta                                                20

<210> SEQ ID NO 67
<211> LENGTH: 20
<212> TYPE: DNA
<213> ORGANISM: Artificial Sequence

```
<220> FEATURE:
<223> OTHER INFORMATION: forward primer for SLC36A1

<400> SEQUENCE: 67
tctgccgcag gctgaataaa                                               20

<210> SEQ ID NO 68
<211> LENGTH: 20
<212> TYPE: DNA
<213> ORGANISM: Artificial Sequence
<220> FEATURE:
<223> OTHER INFORMATION: reverse primer for SLC36A1

<400> SEQUENCE: 68
gagtcgcgag tccatggtag                                               20

<210> SEQ ID NO 69
<211> LENGTH: 20
<212> TYPE: DNA
<213> ORGANISM: Artificial Sequence
<220> FEATURE:
<223> OTHER INFORMATION: forward primer for SLC9A3

<400> SEQUENCE: 69
caggatccct acgtcatcgc                                               20

<210> SEQ ID NO 70
<211> LENGTH: 20
<212> TYPE: DNA
<213> ORGANISM: Artificial Sequence
<220> FEATURE:
<223> OTHER INFORMATION: reverse primer for SLC9A3

<400> SEQUENCE: 70
gaagtccagc agcccaatct                                               20

<210> SEQ ID NO 71
<211> LENGTH: 20
<212> TYPE: DNA
<213> ORGANISM: Artificial Sequence
<220> FEATURE:
<223> OTHER INFORMATION: forward primer for SLC26A3

<400> SEQUENCE: 71
gcacaggagg caaaacacag                                               20

<210> SEQ ID NO 72
<211> LENGTH: 20
<212> TYPE: DNA
<213> ORGANISM: Artificial Sequence
<220> FEATURE:
<223> OTHER INFORMATION: reverse primer for SLC26A3

<400> SEQUENCE: 72
ttgggtcctg aacacgatgg                                               20

<210> SEQ ID NO 73
<211> LENGTH: 24
<212> TYPE: DNA
<213> ORGANISM: Artificial Sequence
<220> FEATURE:
<223> OTHER INFORMATION: forward primer for CYP3A4

<400> SEQUENCE: 73
ctgtgtgttt ccaagagaag ttac                                          24
```

```
<210> SEQ ID NO 74
<211> LENGTH: 21
<212> TYPE: DNA
<213> ORGANISM: Artificial Sequence
<220> FEATURE:
<223> OTHER INFORMATION: reverse primer for CYP3A4

<400> SEQUENCE: 74
tgcatcaatt tcctcctgca g                                              21

<210> SEQ ID NO 75
<211> LENGTH: 19
<212> TYPE: DNA
<213> ORGANISM: Artificial Sequence
<220> FEATURE:
<223> OTHER INFORMATION: forward primer for CYP3A5

<400> SEQUENCE: 75
gctcgcagcc cagtcaata                                                 19

<210> SEQ ID NO 76
<211> LENGTH: 19
<212> TYPE: DNA
<213> ORGANISM: Artificial Sequence
<220> FEATURE:
<223> OTHER INFORMATION: reverse primer for CYP3A5

<400> SEQUENCE: 76
aggtggtgcc ttattgggc                                                 19

<210> SEQ ID NO 77
<211> LENGTH: 21
<212> TYPE: DNA
<213> ORGANISM: Artificial Sequence
<220> FEATURE:
<223> OTHER INFORMATION: forward primer for CYP2C9

<400> SEQUENCE: 77
atcaagattt tgagcagccc c                                              21

<210> SEQ ID NO 78
<211> LENGTH: 20
<212> TYPE: DNA
<213> ORGANISM: Artificial Sequence
<220> FEATURE:
<223> OTHER INFORMATION: reverse primer for CYP2C9

<400> SEQUENCE: 78
agggttgtgc ttgtcgtctc                                                20

<210> SEQ ID NO 79
<211> LENGTH: 21
<212> TYPE: DNA
<213> ORGANISM: Artificial Sequence
<220> FEATURE:
<223> OTHER INFORMATION: forward primer for UGT1A1

<400> SEQUENCE: 79
aacaaggagc tcatggcctc c                                              21

<210> SEQ ID NO 80
<211> LENGTH: 21
<212> TYPE: DNA
<213> ORGANISM: Artificial Sequence
<220> FEATURE:
<223> OTHER INFORMATION: reverse primer for UGT1A1
```

<400> SEQUENCE: 80
ccacaattcc atgttctcca g					21

<210> SEQ ID NO 81
<211> LENGTH: 20
<212> TYPE: DNA
<213> ORGANISM: Artificial Sequence
<220> FEATURE:
<223> OTHER INFORMATION: forward primer for ALPI

<400> SEQUENCE: 81
ctcactgagg cggtcatgtt					20

<210> SEQ ID NO 82
<211> LENGTH: 20
<212> TYPE: DNA
<213> ORGANISM: Artificial Sequence
<220> FEATURE:
<223> OTHER INFORMATION: reverse primer for ALPI

<400> SEQUENCE: 82
taggctttgc tgtcctgagc					20

<210> SEQ ID NO 83
<211> LENGTH: 20
<212> TYPE: DNA
<213> ORGANISM: Artificial Sequence
<220> FEATURE:
<223> OTHER INFORMATION: forward primer for MUC13

<400> SEQUENCE: 83
cggatgactg cctcaatggt					20

<210> SEQ ID NO 84
<211> LENGTH: 20
<212> TYPE: DNA
<213> ORGANISM: Artificial Sequence
<220> FEATURE:
<223> OTHER INFORMATION: reverse primer for MUC13

<400> SEQUENCE: 84
aaagacgctc ccttctgctc					20

<210> SEQ ID NO 85
<211> LENGTH: 21
<212> TYPE: DNA
<213> ORGANISM: Artificial Sequence
<220> FEATURE:
<223> OTHER INFORMATION: forward primer for CLDN4

<400> SEQUENCE: 85
ggctgctttg ctgcaactgt c					21

<210> SEQ ID NO 86
<211> LENGTH: 20
<212> TYPE: DNA
<213> ORGANISM: Artificial Sequence
<220> FEATURE:
<223> OTHER INFORMATION: reverse primer for CLDN4

<400> SEQUENCE: 86
gagccgtggc accttacacg					20

<210> SEQ ID NO 87

```
<211> LENGTH: 21
<212> TYPE: DNA
<213> ORGANISM: Artificial Sequence
<220> FEATURE:
<223> OTHER INFORMATION: forward primer for CLDN7

<400> SEQUENCE: 87
ccatgactgg aggcatcatt t                                         21

<210> SEQ ID NO 88
<211> LENGTH: 21
<212> TYPE: DNA
<213> ORGANISM: Artificial Sequence
<220> FEATURE:
<223> OTHER INFORMATION: reverse primer for CLDN7

<400> SEQUENCE: 88
gacaatctgg tggccatacc a                                         21

<210> SEQ ID NO 89
<211> LENGTH: 21
<212> TYPE: DNA
<213> ORGANISM: Artificial Sequence
<220> FEATURE:
<223> OTHER INFORMATION: forward primer for CLDN15

<400> SEQUENCE: 89
catcaccacc aacaccatct t                                         21

<210> SEQ ID NO 90
<211> LENGTH: 21
<212> TYPE: DNA
<213> ORGANISM: Artificial Sequence
<220> FEATURE:
<223> OTHER INFORMATION: reverse primer for CLDN15

<400> SEQUENCE: 90
gctgctgtcg ccttcttggt c                                         21
```